(12) United States Patent
Solinger et al.

(10) Patent No.: US 7,695,718 B2
(45) Date of Patent: Apr. 13, 2010

(54) METHODS FOR THE TREATMENT OF IL-1β RELATED DISEASES

(75) Inventors: Alan M. Solinger, Oakland, CA (US); Patrick J. Scannon, San Francisco, CA (US); Robert J. Bauer, Pleasant Hill, CA (US)

(73) Assignee: Xoma Technology Ltd., Berkeley, CA (US)

( * ) Notice: Subject to any disclaimer, the term of this patent is extended or adjusted under 35 U.S.C. 154(b) by 0 days.

(21) Appl. No.: 11/961,764

(22) Filed: Dec. 20, 2007

(65) Prior Publication Data

US 2008/0292640 A1 Nov. 27, 2008

Related U.S. Application Data

(60) Provisional application No. 60/911,033, filed on Apr. 10, 2007, provisional application No. 60/908,389, filed on Mar. 27, 2007, provisional application No. 60/871,046, filed on Dec. 20, 2006.

(51) Int. Cl.
  *A61K 39/395* (2006.01)
  *A61K 38/20* (2006.01)
  *C07K 14/545* (2006.01)

(52) U.S. Cl. .................. 424/145.1; 424/85.2; 530/351; 530/387.1; 514/12; 514/866

(58) Field of Classification Search ........................ None
See application file for complete search history.

(56) References Cited

U.S. PATENT DOCUMENTS

| | | | |
|---|---|---|---|
| 4,762,914 A | 8/1988 | Auron et al. |
| 4,766,069 A | 8/1988 | Auron et al. |
| 4,772,685 A | 9/1988 | Schmidt et al. |
| 4,935,343 A | 6/1990 | Allison et al. |
| 5,001,057 A | 3/1991 | Auron et al. |
| 5,077,219 A | 12/1991 | Auron et al. |
| 5,122,459 A | 6/1992 | Conlon et al. |
| 5,286,847 A | 2/1994 | Gehrke et al. |
| 5,348,858 A | 9/1994 | Uetsuki et al. |
| 5,474,899 A | 12/1995 | Lsi |
| 5,484,887 A | 1/1996 | Kronheim et al. |
| 5,510,462 A | 4/1996 | Auron et al. |
| 5,658,570 A | 8/1997 | Newman et al. |
| 5,681,933 A | 10/1997 | Auron et al. |
| 5,766,886 A | 6/1998 | Studnicka et al. |
| 5,789,185 A | 8/1998 | Lisi |
| 5,869,619 A | 2/1999 | Studnicka |
| 5,885,793 A | 3/1999 | Griffiths |
| 5,959,085 A | 9/1999 | Garrone et al. |
| 6,899,878 B2 | 5/2005 | Graham et al. |
| 7,531,166 B2 | 5/2009 | Masat et al. |
| 2003/0022869 A1 | 1/2003 | Wiemer et al. |
| 2003/0026806 A1 | 2/2003 | Witte et al. |
| 2003/0124617 A1 | 7/2003 | Gram et al. |
| 2003/0166069 A1 | 9/2003 | Welcher et al. |
| 2004/0023869 A1 | 2/2004 | Sims et al. |
| 2004/0063913 A1 | 4/2004 | Gram et al. |
| 2005/0084493 A1 | 4/2005 | Witte et al. |
| 2005/0152850 A1 | 7/2005 | Engebretson |
| 2005/0186615 A1 | 8/2005 | Lin et al. |
| 2005/0256197 A1 | 11/2005 | Engebretson |
| 2006/0094663 A1 | 5/2006 | Chemtob |
| 2008/0044414 A1 | 2/2008 | Masat et al. |
| 2009/0060918 A1 | 3/2009 | Masat et al. |
| 2009/0060923 A1 | 3/2009 | Masat et al. |

FOREIGN PATENT DOCUMENTS

| | | | |
|---|---|---|---|
| EP | 0267611 B1 | | 5/1993 |
| EP | 0161901 B1 | | 12/1993 |
| EP | 0364778 B1 | | 3/1996 |
| EP | 0 569 687 B1 | | 8/2002 |
| WO | 95/01997 A1 | | 1/1995 |
| WO | 02/16436 A2 | | 2/2002 |
| WO | 03/010282 A2 | | 2/2003 |
| WO | 03/034984 A2 | | 5/2003 |
| WO | 03/073982 A2 | | 9/2003 |
| WO | 2004/002515 A1 | | 1/2004 |
| WO | 2004002512 | * | 1/2004 |
| WO | 2004/067568 A2 | | 8/2004 |
| WO | 2004/072116 A2 | | 8/2004 |
| WO | 2005019259 A2 | | 3/2005 |
| WO | 2005084696 A1 | | 9/2005 |
| WO | 2006081139 A2 | | 8/2006 |
| WO | 2007002261 A2 | | 1/2007 |
| WO | 2007/042524 A2 | | 4/2007 |
| WO | 2007042524 | * | 4/2007 |
| WO | 2007/120828 A1 | | 10/2007 |
| WO | 2008/077145 A2 | | 6/2008 |
| WO | 2004022718 A2 | | 6/2008 |

OTHER PUBLICATIONS

Houghten et al. New Approaches to Immunization, Vaccines 86, Cold Spring Harbor Laboratory, p. 21-25, 1986.*
Van Gaal et al, Diabetolgia, 2003, suppl [1], pp. M44-M50.*
Bloomgarden, "Concepts of Insulin Resistence", Metabolic Syndrome and Related Disorders, 3(4):284-293 (2005).
Johnson, et al, "Inhibition of vagally mediated immune-to-brain signalling by vanadyl sulfate speeds recovery from sickness", PNAS 102: 15184-89 (2005).
Scheen et al., "Internal carotid artery occlusion detected with nonmydriatic fundus photography: a case report" Diabetes Care, 22(9):1568-1577 (1999).
Maedler et al, "Glucose-induced B cell production of IL-1B contributes to glucose toxicity in human pancreatic islets", J Clin Invest 110:851-860 (2002).

(Continued)

*Primary Examiner*—Bridget E Bunner
*Assistant Examiner*—Fozia M Hamud
(74) *Attorney, Agent, or Firm*—John Polo; K&L Gates LLP

(57) ABSTRACT

Disclosed are methods for the treatment and/or prevention of Type 2 diabetes, insulin resistance and disease states and conditions characterized by insulin resistance, obesity, hyperglycemia, hyperinsulinemia and Type 1 diabetes, comprising administering to a subject an effective amount of anti-IL-1β antibody or fragment thereof.

54 Claims, 12 Drawing Sheets

OTHER PUBLICATIONS

Donath et al, "Inflammatory mediators and islet Bcell failure; a link between type 1 and type 2 diabetes", J Mol Med 81:455-470 (2003).
Larsen et al, "Interleukin-1-receptor antagonist in type 2 diabetes mellitus", New England Journal of Medicine 356:1517-1526 (2007).
Maybee, et al "Is anti-inflammatory therapy for type-2 diabetes mellitus ready for routine clinical practice?", Nature Cinical Practice, 3(12): 806-7 (2007).
Trayhurn et al., "Adipokines: inflammation and the pleiotropic role of white adipose tissue" Br. J. Nutr. 92:347-355, 2004.
Wisse, "The inflammatory syndrome: the role of adipose tissue cytokines in metabolic disorders linked to obesity", J. Am. Soc. Nephrol. 15:2792-2800, 2004.
Fantuzzi, "Adipose tissue, adipokines, and inflammation", J. Allergy Clin. Immunol. 115:911-919 (2005).
Matsuzawa, "The metabolic syndrome and adipocytokines", FEBS Lett. 580:2917-2921 (2006).
Greenberg et al., "Identifying the links between obesity, insulin resistance and beta-cell function: potential role of adipocyte-derived cytokines in the pathogenesis of type 2 diabetes", Eur J. Clin. Invest. 32 Suppl.3:24-34 (2002).
Jager, et al., "Interleukin-1Beta-Induced Insulin Resistance in Adipocytes Through Down-Regulation of Insulin Receptor Substrate-1 Expression", Endocrinology 148:241-251 (2007).
Kern et al., "Adiponectin expression from human adipose tissue: relation to obesity, insulin resistance, and tumor necrosis factor-alpha expression", Diabetes 52:1779-1785 (2003).
Alheim, et al., Hyperresponsive febrile reactions to interleukin (IL) 1alpha and IL-1beta, and altered brain cytokine mRNA and serum cytokine levels in IL 1 beta deficient mice. Proc. Natl. Acad. Sci. 94:2681-686 (1997).
Smith et al., "The soluble form of IL-1 receptor accessory protein enhances the ability of soluble type II IL-1 receptor to inhibit IL-1 action", Immunity 18:87-96 (2003).
Slack et al., "Independent binding of interleukin-1 alpha and interleukin-1 beta to type I and type II interleukin-1 receptors", J. Biol. Chem. 268:2513-2524 (1993).
Fredericks et al., "Identification of potent human anti-IL-1RI antagonist antibodies", Protein Eng. Des. Sel. 17:95-106 (2004).
Yanofsky et al.,"High affinity type I interleukin 1 receptor antagonists discovered by screening recombinant peptide libraries", Proc. Natl. Acad. Sci. USA 93:7381-7386 (1996).
Vigers et al., "X-ray crystal structure of a small antagonist peptide bound to interleukin-1 receptor type 1", J. Biol. Chem. 275:36927-36933 (2000).
Evans et al., "Mapping receptor binding sites in interleukin (IL)-1 receptor antagonist and IL-1 beta by site-directed mutagenesis. Identification of a single site in IL-1ra and two sites in IL-1 beta.", J. Biol. Chem. 270:11477-11483 (1995).
Vigers et al., "Crystal structure of the type-I interleukin-1 receptor complexed with interleukin-1beta", Nature 386:190-194 (1997).
Ruggiero et al., "Inhibitory activity of IL-1 receptor antagonist depends on the balance between binding capacity for IL-1 receptor type 1 and IL-1 receptor type II", J. Immunol. 158:3881-3887 (1997).
Guo et al., "Fluorescence resonance energy transfer reveals interleukin (IL)-1-dependent aggregation of IL-1 type I receptors that correlates with receptor activation", J. Biol. Chem. 270:27562-27568 (1995).
Svenson et al., "Differential binding of human interleukin-1 (IL-1) receptor antagonist to natural and recombinant soluble and cellular IL-1 type I receptors.", Eur. J. Immunol. 25:2842-2850 (1995).
Arend et al., "Binding of IL-1 alpha, IL-1 beta, and IL-1 receptor antagonist by soluble IL-1 receptors and levels of soluble IL-1 receptors in synovial fluids", J. Immunol. 153:4766-4774 (1994).
Nathan, Thiazolidinediones for initial treatment of type 2 diabetes?, N. Engl. J. Med. 355:2477-2480 (2006).
Kahn, et al.,"Glycemic Durability of Rosiglitazone, Metformin, or Glyburide Monotherapy", N. Engl. J. Med. 355 (23):2427-2443 (2006).
Donath, et al., "Mechanisms of B-Cell Death in Type 2 Diabetes", Diabetes, 54(2):108-113 (2005).

Donath, et al., "Decreased beta-cell mass in diabetes: significance, mechanisms and therapeutic implications", Diabetologia, 47:581-589 (2004).
Feingold, et al., "Effect of Interleukin-1 on Lipid Metabolism in the Rat. Similarities to and differences from tumor necrosis factor", Arteriosclerosis and Thrombosis and Vacular Biology, Am Heart Assoc., 11(3):495-500 (1991).
Maedler et al., "Leptin modulates beta cell expression of IL-1 receptor antagonist and release of IL-1beta in human islets", Proc. Natl. Acad. Sci. USA 101:8138-8143 (2004).
Donath et al.,"Hyperglycemia-induced beta-cell apoptosis in pancreatic islets of Psammomys obesus during development of diabetes", Diabetes 48:738-744 (1999).
Reddy et al., "Immunoexpression of interleukin-1beta in pancreatic islets of NOD mice during cyclophosphamide-accelerated diabetes: co-localization in macrophages and endocrine cells and its attenuation with oral nicotinamide" Histochem J. 33:317-32, (2001).
Cailleau et al., "Treatment with neutralizing antibodies specific for IL-1 beta prevents cyclophosphamide-induced diabetes in nonobese diabetic mice" Diabetes 46:937-940 (1997).
Reddy et al., "Immunoexpression of interleukin-1beta in pancreatic islets of NOD mice during cyclophosphamide-accelerated diabetes: co-localization in macrophages and endocrine cells and its attenuation with oral nicotinamide", Histochem J., 34:1-12 (2002).
Harada et al., "Promotion of spontaneous diabetes in non-obese diabetes-prone mice by cyclophosphamide" Diabetologia 27:604-606 (1984).
Nicoletti, et al., "Protection from experimental autoimmune diabetes in the non-obese diabetic mouse with soluble interleukin-1 receptor", Eur J Immunol 24:1843-7 (1994).
Mellgren et al., "The renal subcapsular site offers better growth conditions for transplanted mouse pancreatic islet cells than the liver or spleen", Diabetologia 29:670-2 (1986).
Sandberg, et al.,"IL-1 receptor antagonist inhibits recurrence of disease after syngeneic pancreatic islet transplantation to spontaneously diabetic non-obese diabetic (NOD) mice", Clin Exp Immunol 108:314-7 (1997).
Dinarello, "Therapeutic strategies to reduce IL-1 activity in treating local and systemic inflammation", Curr. Opin. Pharmacol. 4:378-385 (2004).
Studnicka et al. "Human-engineered monoclonal antibodies retain full specific binding activity by preserving non-CDR complementarity-modulating residues", Protein Engineering, 7: 805-814 (1994).
O'Connor, et al., "IL-1Beta- Mediated Innate Immunity is Amplified in the db/db Mouse Model of Type 2 Diabetes", Journal of Immunology 174:4991-4997 (2005).
Kaizer, et al., "Gene Expression in Peripheral Blood Mononuclear Cells From Children With Diabetes", J Clin Endocrin Metab. 92(9):3705-3711 (2007).
D'Ettorre, et al., "Functional epitope mapping of human interleukin-1B by surface plasmon resonance." Eur. Cytokine Netw. 8:161-171 (1997).
Boraschi et al., Differential inhibition of IL-1Beta activities and receptor binding of monoclonal antibodies mapping within a discrete region of the protein. Lymphokine Cytokine Res. 10:377-384 (1991).
Towbin et al., Neoepitope immunoassay: An assay for human interleukin 1Beta based on an antibody induced conformational change. J. Immunoassay 17:353-369 (1996).
Jackson, et al., In vitro antibody maturation: Improvement of a high affinity, neutralizing antibody against IL-1beta. J. Immunol. 154:3310-3319 (1995).
Kock, et al., Characterization of a monoclonal antibody directed against the biologically active site of human interleukin 1. J. Exp. Med. 163:463-468 (1986).
Dinarello, et al., The production of antibody against human leukocytic pyrogen. J. Clin. Invest. 60:465-472 (1977).
Dinarello et al., Human leukocytic pyrogen: purification and development of a radioimmunoassay. Proc. Natl. Acad. Sci. USA 74:4624-4627 (1977).
Lu et al., IL-1beta epitope mapping using site-directed mutagenesis and hydrogen-deuterium exchange mass spectrometry analysis. Biochemistry 44:11106-11114 (2005).

Garrone et al., Generation and characterization of a human monoclonal autoantibody that acts as a high affinity interleukin-1 alpha specific inhibitor. Mol. Immunol. 33:649-658 (1996).
Mcintyre et al., Inhibition of interleukin 1 (IL-1) binding and bioactivity in vitro and modulation of acute inflammation in vivo by IL-1 receptor antagonist and anti-IL-1 receptor monoclonal antibody. J. Exp. Med. 173:931-939 (1991).
Gershenwald et al., Interleukin 1 receptor blockade attenuates the host inflammatory response. Proc. Natl. Acad. Sci. USA 87:4966-4970 (1990).
Herzbeck et al., Functional and molecular characterization of a monoclonal antibody against the 165-186 peptide of human IL-1 beta. Scand. J. Immunol. 30:549-562 (1989).
Boraschi et al., A monoclonal antibody to the IL-1 beta peptide 163-171 blocks adjuvanticity but not pyrogenicity of IL-1 beta in vivo. J. Immunol. 143:131-134 (1989); Erratum in: J. Immunol. 143:1403 (1989).
Chen et al., Effects of interleukin-1alpha, interleukin-1 receptor antagonist, and neutralizing antibody on proinflammatory cytokine expression by human squamous cell carcinoma lines. Cancer Res. 58:3668-3676 (1998).
Dinarello, "Biologic basis for interleukin-1 in disease", Blood, J Amer Soc Hematology, 87(6):2095-147 (1996).
Dinarello, The many worlds of reducing interleukin-1. Arthritis Rheum. 52:1960-1967 (2005).
Kenney et al., Monoclonal antibodies to human recombinant interleukin 1 (IL 1beta): Quantitation of IL 1beta and inhibition of biological activity. J. Immunol. 138:4236-4242 (1987).
Dinarello, Blocking IL-1 in systemic inflammation. J. Exp. Med. 201:1355-1359 (2005).
Smith et al., A single amino acid difference between human and monkey interleukin (IL)-1beta dictates effective binding to soluble type II IL-1 receptor. J. Biol. Chem. 277:47619-47625 (2002).
Yoon, et al., Antibodies to Domains II and III of IL-1 Receptor Accessory Protein Inhibit IL-1beta Activity But Not Binding: Regulation of IL-1 Responses is Via Type I Receptor, Not the Accessory Protein. J. Immuno. [3171-79] (1998).
Massone, et al., Mapping of Biologically Relevant Sites of Human IL-1beta Using Monoclonal Antibodies. J. Immuno. 140, No. 11 [3812-3816] (1988).
Faggioni, et al., ABX10-0031, a High Affinity Fully Human Anti-IL-1b Monoclonal Antibody for the Treatment of Inflammatory Diseases. Abstract for Presentation at 7th World Congress on Inflammation. Aug. 20-24, 2005 (Melbourne, Australia).
Khovidhunkit, et al., "Effects of infection and inflammation on lipo and lipoprotein metabolism; mechanisms and consequences to the host", J Lipid Research, 45:1169-96 (2004).
Pascual, et al., "Role of interleukin-1 (IL-1) in the pathogenesis of systemic onset juvenile idiopathic arthritis and clinical response to IL-1 blockade", J Exper Med. 201(9):1479-86 (2005).
Thomas, et al., "Il-1 Receptor Deficiency Slows Progression to Diabetes in the NOD Mouse", Diabetes, 53: 113-121 (2004).
Tilg, et al., "Adipocytokines; mediators linking adipose tissue, inflammation and immunity" Nature Rev Immun, 6:772-83 (2006).
Dinarello, C.A., "IL-1 beta", in Cytokine Reference: A compendium of cytokines and other mediators of host defense, Academic Press, p. 351-374 (2001).
Faggioni, et al., "IL-1 mediates leptin induction during inflammation" American Journal of Physiology-Regulatory 274:204-08 (1998).
Fantuzzi, et al., "Response to local inflammation of IL-1beta converting enzyme-deficient mice" J Immunology 158:1818-824 (1997).
Fantuzzi, et al. "Physiological and cytokine responses in interleukin-1beta deficient mice after zymosan-induced inflammation". American Journal of Physiology (1997).
Fantuzzi, et al., "Effect of endotoxin in IL-1beta deficient mice" Journal of Immunology 157:291-96 (1996).
Grundy, S.M., "Metabolic syndrome: connecting and reconciling cardiovascular and diabetes worlds", J. Am. Coll. Cardiol. 47:1093-1000 (2006).

Hoffman, et al., "Prevention of cold-associated acute inflammation in familial cold autoinflammatory syndrome by interleukin-1 receptor antagonist" Lancet 364:1779-85 (2004).
Kozak, et al. "IL-6 and IL-1beta in fever: studies using cytokine-deficient (knockout) mice" Annals of the New York Academy of Sciences 856:33-47 (1998).
Lovell, et al., "Interleukin-1 blockade by anakinra improves clinical systems in patients with neonatal-onset multisystem inflammatory disease" Arthritis and Rheumatism 52(4):1283-86 (2005).
Reznikov, et al., "Utilization of endoscopic inoculation in a mouse model of intrauterin infection-induced preterm birth: role of interleukin 1beta" Biology Reproduction 60:1231-238 (1999).
Zheng, et al., Resistance to fever induction and impaired acute-phase response in interleukin-1beta deficient mice. Immunity 3:9-19 (1995).
Barzilay, et al., Cardiovascular disease in older adults with glucose disorders: comparison of American Diabetes Association criteria for diabetes mellitus with WHO criteria. Lancet 354:622-25 (1999).
Butler, et al., Beta-cell deficit and increased beta-cell apoptosis in humans with type 2 diabetes. Diabetes 52:102-10 (2003).
Kim, et al., Comparison of the 1997 and 2003 American Diabetes Association classification of impaired fasting glucose. Journal of the American College of Cardiology 48(2):293-97 (2006).
Mayfield, Diagnosis and classification of diabetes mellitus: new criteria. Am Fam Physician 58:1355-62 (1998).
Sakuraba, et al., Reduced beta-cell mass and expression of oxidative stress-related DNA damage in the islet of Japanese type II diabetic patients. Diabetologia 45:85-96 (2002).
Dinarello CA. Biologic basis for interleukin-1 in disease. Blood-Am Soc Hematology 87(6):2095-147 (1996).
Scheen et al., Troglitazone: Antihyperglycemic Activity and Potential Role in the Treatment of Type 2 Diabetes. Diabetes Care, 22(9):1568-1577 (1999).
Nathan, Thiazolidinediones for initial treatment of type 2 diabetes?, N. Engl. J. Med. 355:2477-2480 (2006).
Perrier, et al., IL-1 Receptor antagonist in metabolic disease: Dr. Jekyll or Mr. Hyde?, FEBS Letters 580: 6289-94 (2006).
Rydgren, et al., Complete protection against interleukin-1beta-induced functional suppression and cytokine-mediated cytotoxicity in rat pancreatic islets in vitro using an interleukin-1 cytokine trap. Diabetes, 55(5):1407-12 (2006).
Vincent, et al., Inhibition of Caspase-1/Interleukin-1beta Signaling Prevents Degeneration of Retinal Capillaries in Diabetes and Galactosemia. Diabetes. 56(1):224-30 (2007).
Akahoshi, et al., Recent advances in crystal-induced acute inflammation, Current Opinion in Rheumatology 19:146-150 (2007).
Eggebeen, Gout: An Update, Am. Family Physician 76(6): 801-8, 811-2 (2007).
Cronstein, et al., The Inflammatory Process of Gout and its Treatment, Arthrities Research & Therapy 8(Suppl 1): S3 (2006).
Dinarello, Therapeutic strategies to reduce IL-1 activity in treating local and systemic inflammation, Current Opinion in Pharmacology 4:378-385 (2004).
Economides, et al., Cytokine traps: multi-component, high affinity blockers of cytokine action, Nature Medicine 9 (1):47-52 (2003).
Emad, et al., The Diagnostic dilemma of undifferentiated inflammatory synovitis of the knee joint/joints: a comprehensive approach, APLAR Journal of Rheumatology 10:182-189 (2007).
Martinon, et al., Gout: New insights into an old disease, J. Clin. Invest. 116:2073-2075 (2006).
Martinon, et al., Gout associated uric-acid crystals activate the NALP3 inflammasome, Nature 440:237-241 (2006).
Petrilli and Martinon., The inflammasome, autoimflammatory diseases and gout, Joint Bone Spine 74:571-576 (2007).
McGonagle, et al., Management of treatment resistent inflammation of acute on chronic tophaceous gout with anakinra, Ann. Rheum. Dis. 66:1683-1684 (2007).
Pope and Tschopp, The Role of Interleukin-1 and the Inflammasome in Gout, Arthritis and Rheumatism 56 (10):3183-88 (2007).
Schlesinger, Management of Acute and Chronic Gouty Arthritis, Drugs 64(21): 2399-2416 (2004).
So, et al., A pilot study of IL-1 inhibition by anakinra in acute gout, Arthritis Research & Therapy 9:R28 (2007).

Bieber and Terkeltaub, On the Brink of Novel Therapeutic Options for an Ancient Disease, Arthritis & Rheumatism 50 (8):2400-2414 (2004).

Chen, et al., MyD88 dependent IL-1 receptor signalling is essential for gouty inflammation stimulated by monosodium urate crystals, J. Clin. Investig. 116(8): 2262-71 (2006).

Di Giovine, et al., Urate Crystals Stimulate Production of Tumor Necrosis Factor Alpha from Human Blood Monocytes and Synovial Cells, J. Clin. Invest. 87:1375-1381 (1991).

Di Giovine, et al., Interleukin 1 (IL-1) as a mediator of crystal arthritis, J. Immunology 138(10): 3213-3218 (1987).

Liu-Bryan, et al., Innate Immunity Conferred by Toll-like Receptors 2 and 4 and Myeloid Differentiation Factor 88 Expression is Pivotal to Monosodium Urate Monohydrate Crystal-induced Inflammation, Arthritis & Rheumatism 52 (9):2936-46 (2005).

Liu-Bryan, et al., TLR2 Signaling in Chondrocytes Drives Calcium Pyrophosphate Dihydrate and Monosodium Urate Crystal-Induced Nitric Oxide Generation, J. Immunology 174:5016-5023 (2005).

Nuki and Simkin, A concise history of gout and hyperuricmia and their treatment, Arthritis Research & Therapy 8(Suppl 1):S1 (2006).

Guerne, et al., Inflammatory microcrystals stimulate interleukin-6 production and secretion by human monocytes and synoviocytes. Arthritis and Rheumatism 32(11):1443-452 (1989).

Simkin PA, The pathogenesis of podagra. Annals of Internal Medicine 86:230-33 (1977).

Terkeltaub, et al., Monocyte-derived neutrophil chemotactic factor/interleukin-8 is a potential mediator of crystal-induced inflammation. Arthritis and Rheumatism 34(7):894-903 (1991).

Haraoui et al., Biologic agents in the treatment of rheumatoid arthritis. Curr. Pharm. Biotechnol. 1:217-233 (2000).

Ledingham, et al., Nitric oxide donors stimulate prostaglandin F2a and inhibit thromboxane B2 production in the human cervix during the first trimester of pregnancy. Mol, Hum. Reprod. 5, No. 10 [973-82] (1999).

Abramson et al., Blocking the effects of IL-1 in rheumatoid arthritis protects bone and cartilage. Rheumatology 41:972-980 (2002).

Dayer, The pivotal role of interleukin-1 in the clinical manifestations of rheumatoid arthritis. Rheumatology 42 (Suppl.2):ii3-ii10 (2003).

Joosten, et al., IL-1abeta blockade prevents cartilage and bone destruction in murine type II collagen-induced arthritis, whereas TNF-a blockade only ameliorates joint inflammation. J. Immunol. 163:5049-5055 (1999).

Yang et al., IL-1 receptor antagonist-mediated therapeutic effect in murine myasthenia gravis is associated with suppressed serum proinflammatory cytokines, C3 and anti-acetylcholine receptor IgG1. J. Immunol. 175:2018-2025 (2005).

Osnes, et al., Inhibition of IL-1 induced tissue factor (TF) synthesis and procoagulant activity (PCA) in purified human monocytes by IL-4,1L-10 and IL-13. Cytokine 8, No. 11 [822-7] (1996).

Napoleone, et al., Monocytes Upregulate Endothelial Cell Expression of Tissue Factor: A Role for Cell-Cell Contact and Cross-Talk. Blood, 89, No. 2 [541-9] (1997).

Kuhns, et al., Ca2+-Dependent Production and Release of IL-3 in Human Neutrophils. J. Immuno. 161, No. 8 [4332-39] (1998).

Dezzutti, et al., Involvement of Matrix Metalloproteinases in Human Immunodeficiency Virus Type 1-Induced Replication by Clinical Mycobacterium avium Isolates. J. Infect. Dis. 180 [1142-52] (1999).

Grunstein, et al., Autocrine cytokine signaling mediates effects of rhinovirus on airway responsiveness. Am. J. Physiol Lung Cell Mol. Physiol. 278 [L1146-53] (2000).

Hedges, et al., Mitogen-Activated Protein Kinases Regulate Cytokine Gene Expression in Human Airway Myocytes. Am. J. Respir. Cell Mol. Bio. 23 [86-94] (2000).

Morisaki, et al., A combination of Cyclosporin-A (CsA) and InterferonGamma (INF-y) Induces Apoptosis in Human Gastric Carcinoma Cells. Anticancer Research 20 [3363-74] (2000).

Yates, et al., Amyloid β and Amylin Fibrils Induce Increases in Proinflammatory Cytokine and Chemokine Production by THP-1 Cells and Murine Microglia. J. Neurochem. 74 [1017-25] (2000).

Moldovan, et al., Diacerhein and rhein reduce the ICE-induced 1L-1β and IL-18 activation in human osteoarthritic cartilage. Osteoarthritis and Cartilage 8 [186-96] (2000).

Yoshiie, et al., Intracellular Infection by the Human Granulocytic Ehrlichiosis Agent Inhibits Human Neutrophil Apoptosis. Infection and Immunity 68(3):1125-33 (2000).

Kawakami, et al., CD4+ T Cell Mediated Cytotoxicity Toward Thyrocytes: The Importance of Fas/Fas Ligand Interaction Inducing Apoptosis of Thyrocytes and the Inhibitory Effect of Thyroid-Stimulating Hormone. Lab. Invest. 80, No. 4:471-84 (2000).

Novak et al., Engagement of FceR1 on Human Monocytes Induces the Production of IL-10 and Prevents Their Differentiation in Dendritic Cells. J. Immuno. 167, No. 2 [797-804] (2001).

Levesque, et al., Activated T Lymphocytes Regulate Hyaluronan Binding to Monocyte CD44 Via Production of IL-2 and IFN-y. J. Immuno. 166, No. 1 [188-96] (2001).

Sennikov, et al., Production of cytokines by immature erythroid cells derived from human embryonic liver. Eur. Cytokine Netw. 12, No. 2 [274-9] (2001).

Lin, et al., Lin, et al. Pseudomonas aeruginosa Activates Human Mast Cells to Induce Neutrophil Transendothelial Migration Via Mast Cell-Derived IL-1a and b. J. Immuno. 169:4522-30 (2002).

Li, et al., Expression of caspase-1 in synovial membrane-like interface tissue around loosened hip prostheses. Rheum. Int'l. 22 [97-102] (2002).

Rawlins, et al., Inhibition of endotoxin-induced TNF-a production in macrophages by 5Z 7-oxo-zeaenol and other fungal resorcylic acid lactones. Int. J. Irnmunopharm. Acol. 21, No. 12 [712-814] (1999).

Gracie, et al., A proinflammatory role for IL-18 in rheumatoid arthritis. J. Clin, Invest. 104, No. 10 [1393-401] (1999).

Trindade, et al., Interleukin-4 Inhibits Granulocyte-Macrophage Colony-Stimulating Factor, Interleukin-6, and Tumor Necrosis Factor-Alpha Expression by Human Monocytes in Response to Polymethylethacrylate Particle Challenge in Vitro. J. Orthop. Res. 176):797-302 (1999).

Gustafsson, et al., Cytokine, elastase and oxygen radical release by Fusobacterium nucleatum-activated leukocytes: a possible pathogenic factor in periodontitis. J. Clin, Periodontol. 27, No. 10 [758-62] (2000).

Marovich, et al., IL-12p70 Production by Leishmania major-Harboring Human Dendritic Cells Is a CD40/CD40 Ligand-Dependent Process. J. Immuno. 164, No. 11 [5658-65] (2000).

Christodoulides, et al., Interaction of primary human endometrial cells with Neisseria gonorrhoeae expressing green fluorescent protein. Mol. Microbiol 35, No. 1 [32-43] (2002).

Park, et al., TGF-beta1 down-regulates inflammatory cytokine-induced VCAM-1 expression in cultured human glomerular-endothelial cells. Nephrol. Dial Transplant 15, No. 5 [596-604] (2000).

Hultin, et al., Microbiological findings and host response in patients with peri-implantitis. Clin. Oral Implants Res. 13 [349-56] (2002).

Brand, et al., Activation and Translocation of p38 Mitogen-Activated Protein Kinase After Stimulation of Monocytes With Contact Sensitizers. J. Invest. Dermatol. 119 [99-106] (2002).

Darling, et al., Kinetic Exclusion Assay Technology: Characterization of Molecular Interactions. Assay and Drug Dev. Tech., vol. 2, No. 6 [647-657] (2004).

Khilko, et al., Measuring Interactions of MHC Class I Molecules Using Surface Plasmon Resonance. J. Immum. Methods., 183 [77-94] (1995).

Wooley PH, et al., The effect of an interleukin-1 receptor antagonist protein on type II collagen-induced arthritis and antigen-induced arthritis in mice. Arthritis Rheum. 1993;36(9):1305-14.

Inoue K, et al., Efficacy of daily compared to intermittent administration of IL-1 Ra for protection against bone and cartilage destruction in collagen-challenged mice. Clin Exp Rheumatol 2003;21(1):33-9.

Goupille P, et al., Safety and efficacy of intra-articular injection of IL-1ra (IL-1 receptor antagonist) in patients with painful osteoarthritis of the knee: a multicenter, double blind study. Arthritis and Rheumatism 2003;48(9).

Bresnihan B, et al. Treatment of rheumatoid arthritis with recombinant human interleukin-1 receptor antagonist. Arthritis Rheum. 1998;41(12):2196-204.

Jacques, C, et al.. The role of IL-1 and IL-Ra in joint inflammation and cartilage degradation. Vitam Horm 2006;74:371-404.

Keystone EC and Strond V, Emerging Therapies in Rheumatoid Arthritis. In: Kelley's Textbook of Rheumatology. Harris E, Jr., M.D., Budd R, M.D., Genovese M, M.D., Firestein GS, M.D., Sargent J, M.D. and Sledge C, M.D., eds. Philadelphia, Elsevier Saunders. 2005:951-60 (chapter 62).

Joosten LA, et al., Anticytokine treatment of established type II collagen-induced arthritis in DBA/1 mice. A comparative study using anti-TNF alpha, anti-IL-1 alpha/beta, and IL-1Ra. Arthritis Rheum. 1996;39(5):797-809.

Punzi L., et al., Pro-inflammatory interleukins in the synovial fluid of rheumatoid arthritis associated with joint hypermobility. Rheumatology. 2001;40:202-204.

Lovell DJ, et al., Preliminary evidence for bioactivity of IL-1 trap (rilonacept), a long acting IL-1 inhibitor, in systemic juvenile idiopathic arthritis (sJIA). Arthritis and Rheumatism 2006;54(9).

Grutter, MG, et al., A mutational analysis of receptor binding sites of interleukin-1β:differences in binding of human interleukin-1β muteins to human and mouse receptors. Protein Eng. 1994;7:663-671.

Sutton C., et al., A crucial role for interleukin (IL)-1 in the induction of IL-17-producing T cells that mediate autoimmune encephalomyelitis. J Exp Med. 2006;203:1685-91.

Geiger T, et al. Neutralization of interleukin-1 beta activity in vivo with a monoclonal antibody alleviates collagen-induced arthritis in DBA/1 mice and prevents the associated acute-phase response. Clin Exp Rheumatol. 1993;11 (5):515-22.

Firestein GS. Rheumatoid Arthritis. ACPMedicine. 2007;15(II):1-18 (in two parts).

Kim KY, A literature review of the epidemiology and treatment of acute gout. ClinTher 2003;25:1593-1616.

Harris ED, et al., Overview of the management of rheumatoid arthritis. UptoDate®. Feb. 4, 2008.

Martinon F, et al., Gout-associated uric acid crystals activate the nalp3 inflammasome. Nature 2006;440(9):237-41.

Nuki G and Simkin PA, A concise history of gout and hyperuricemia and their treatment. Arthritis Research and Therapy 2006;8(1):1-5.

Lichtman AH, et al., Role of interleukin 1 in the activation of T lymphocytes. PNAS. 1988;85:9699-9703.

Dinarello CA, Interleukin-1, inteleukin-1 receptors and interleukin-1 receptor antagonist. Intern Rev Immunol. 1998; 16:457-499.

Hawkins, PN et al. Spectrum of clinical features in muckle-wells syndrome and response to anakinra. Arthritis and Rheumatism. 2004;50:607-612.

Tilg and Moshen, Inflammatory Mechanisms in the Regulation of Insulin Resistance, Mol Med 2008; 14 (3-4) 222-231.

Masat, et al. Unpublished U.S. Appl. No. 12/463,741, filed May 11, 2009.

Masat, et al. Unpublished U.S. Appl. No. 12/463,844, filed May 11, 2009.

Maasat, et al. Unpublished U.S. Appl. No. 12/464,006, filed May 11, 2009.

Masat, et al. Unpublished U.S. Appl. No. 12/464,061, filed May 11, 2009.

Masat, et al. Unpublished U.S. Appl. No. 12/464,323, filed May 12, 2009.

Masat, et al. Unpublished U.S. Appl. No. 12/464,381, filed May 12, 2009.

Abbatecola, A.M., et al., Diverse effect of inflammatory markers on insulin resistance and insulin-resistance syndrome in the elderly. J Am Geriatr Soc 52(3):399-404 (2004).

Alexandraki, K., et al., Inflammatory process in type 2 diabetes: The role of cytokines. Ann N Y Acad Sci, 1084: 89-117 (2006).

Allantaz, F., et al., Microarray-based identification of novel biomarkers in IL-1-mediated diseases. Curr Opin Immunol, 19(6): 623-32 (2007).

Barksby, H.E., et al., The expanding family of interleukin-1 cytokines and their role in destructive inflammatory disorders. Clin Exp Immunol, 149(2): 217-25 (2007).

Baud, Laurent, et al., Switching off rental inflammation by anti-inflammatory mediators: The facts, the promise and the hope. Kidney Int'l 53:1118-1126 (1998).

Bendtzen, K., et al., Cytotoxicity of human pI 7 interleukin-1 for pancreatic islets of Langerhans. Science 232 (4757):1545-7 (1986).

Boni-Schnetzler, M., et al., Increased interleukin (IL)-1beta messenger ribonucleic acid expression in beta-cells of individuals with type 2 diabetes and regulation of IL-1beta in human islets by glucose and autostimulation. J Clin Endocrinol Metab, 93(10): 4065-74 (2008).

Butler, A.E., et al., Beta-cell deficit and increased beta-cell apoptosis in humans with type 2 diabetes. Diabetes 52(1): 102-10 (2003).

Corbett JA, Sweetland MA, Wang JL, Lancaster JR Jr, McDaniel ML. Nitric oxide mediates cytokine-induced inhibition of insulin secretion by human islets of Langerhans. PNAS 90(5):1731-1735 (1993).

Donath, M.Y., et al., XOMA 052, an anti-IL-1beta antibody, in a double-blind, placebo controlled, dose escalation study of the safety and pharmacokinetics in patients with type 2 diabetes mellitus—a new approach to therapy. Diabetologia 51: S1-S7 (2008).

Donath, Marc Y.; Schumann, Desiree M.; Faulenbach, Mirjam; Ellingsgaard, Helga; Perren, Aurel; Ehses, Jan A , Islet Inflammation in Type 2 Diabetes. Diabetes Care 31:S161-S164 (2008).

Ehses, Jan A.; Perren, Aurel; Eppler, Elisabeth; Ribaux, Pascale; Pospisilik, John A.; Maor-Cahn, Ranit; Gueripel, Xavier; Ellingsgaard, Helga; Schneider, Marten K. J.; Biollaz, Gregoire; Fontana, Adriano; Reinecke, Manfred; Homo-Delarche, Francoise; and Donath, Marc Y. Increased Number of Islet-Associated Macrophages in Type 2 Diabetes. Diabetes 56:2356-2370 (2007).

Eizirik, D.L. and T. Mandrup-Poulsen, A choice of death—the signal-transduction of immune-mediated beta-cell apoptosis. Diabetologia 44(12): 2115-33 (2001).

Giannoukakis N, Rudert WA, Ghivizzani SC, et al. Adenoviral gene transfer of the interleukin-1 receptor antagonist protein to human islets preventsIL-1beta-induced beta-cell impairment and activation of islet cell apoptosis in vitro. Diabetes 48(9):1730-1736 (1999).

Heitmeier MR, Arnush M, Scarim AL, Corbett JA. Pancreatic beta-cell damage mediated by beta-cell production of interleukin-1. A novel mechanism for virus-induced diabetes. J Biol Chem 276(14):11151-11158 (2001).

Herder, C. et al., Elevated levels of the anti-inflammatory interleukin-1 receptor antagonist precede the onset of type 2 diabetes: the Whitehall II study. Diabetes Care 32(3): 421-3 (2009).

Hotamisligil, G.S., Inflammation and metabolic disorders. Nature 444(7121): 860-7 (2006).

Lagathu C, Yvan-Charvet L, Bastard JP, et al. Long-term treatment with interleukin-1beta induces insulin resistance in murine and human adipocytes. Diabetologia 49(9):2162-2173 (2006).

LeRoith, D., Beta-cell dysfunction and insulin resistance in type 2 diabetes: role of metabolic and genetic abnormalities. Am J Med 113 Suppl 6A: 3S-11S (2002).

Loweth AC, Williams GT, James RF, Scarpello JH, Morgan NG. Human islets of Langerhans express Fas ligand and undergo apoptosis in response to interleukin-1beta and Fas ligation. Diabetes 47(5):727-732 (1998).

Maedler K, Schumann DM, Sauter N, et al. Low concentration of interleukin-1beta induces FLICE-inhibitory protein-mediated beta-cell proliferation in human pancreatic islets. Diabetes 55(10):2713-2722 (2006).

Maedler K, Spinas GA, Lehmann R, et al. Glucose induces beta-cell apoptosis via upregulation of the Fas receptorin human islets. Diabetes 50(8):1683-1690 (2001).

Mandrup-Poulsen, T., Apoptotic signal transduction pathways in diabetes. Biochem Pharmacol 66(8): 1433-40 (2003).

Mandrup-Poulsen, T., et al., Affinity-purified human interleukin I is cytotoxic to isolated islets of Langerhans. Diabetologia 29(1): 63-7 (1986).

Mandrup-Poulsen, T., et al., Cytokines cause functional and structural damage to isolated islets of Langerhans. Allergy 40(6): 424-9 (1985).

Meier, C.A., et al., IL-1 receptor antagonist serum levels are increased in human obesity: a possible link to the resistance to leptin? J Clin Endocrinol Metab 87(3): 1184-8 (2002).

Mine T, Okutsu T, Mitsui A, Kitahara Y. Gene expression profile in the pancreatic islets of Goto-Kakizaki (GK) rats withrepeated postprandial hyperglycemia. Diabetes 53(suppl 2):2475A (2004).

Odegaard, J.I., et al., Macrophage-specific PPARgamma controls alternative activation and improves insulin resistance. Nature 447(7148): 1116-20 (2007).

Osborn O, Brownell SE, Sanchez-Alavez M, Salomon D, Gram H, Bartfai T. Treatment with an Interleukin 1 beta antibody improves glycemic control in diet-induced obesity. Cytokine. 44(1):141-148 (2008).

Qatanani, M. and M.A. Lazar, Mechanisms of obesity-associated insulin resistance: many choices on the menu. Genes Dev 21(12): 1443-55 (2007).

Ruotsalainen, E., et al., Changes in inflammatory cytokines are related to impaired glucose tolerance in offspring of type 2 diabetic subjects. Diabetes Care 29(12): 2714-20 (2006).

Salmenniemi, U., et al., Multiple abnormalities in glucose and energy metabolism and coordinated changes in levels of adiponectin, cytokines, and adhesion molecules in subjects with metabolic syndrome. Circulation 110(25): 3842-8 (2004).

Sauter NS, Schulthess FT, Galasso R, Castellani LW, Maedler K. The anti-inflammatory cytokine interleukin-1 receptor antagonist protects from high-fat diet-induced hyperglycemia. Endocrinology 149(5):2208-2218 (2008).

Simon P. L. et al., Mapping of neutralizing epitopes and the receptor binding site of human interleukin 1 beta. The Journal of Biological Chemistry. 268(3):9771-9779 (1993).

Somm, E., et al., Interleukin-1 receptor antagonist is upregulated during diet-induced obesity and regulates insulin sensitivity in rodents. Diabetologia 49(2): 387-93 (2006).

Spranger J, Kroke A, Möhlig M, et al. Inflammatory cytokines and the risk to develop type 2 diabetes: results of the prospective population-based European Prospective Investigation into Cancer and Nutrition (EPIC)-Potsdam Study. Diabetes 52(3):812-817 (2003).

Stumvoll, Michael, et al., Type 2 diabetes: principles of pathogenesis and therapy. Lancet 365:1333-46 (2005).

Téllez N, Montolio M, Biarnés M, Castaño E, Soler J, Montanya E. Adenoviral overexpression of interleukin-1 receptor antagonist protein increases beta-cell replication in rat pancreatic islets. Gene Ther 12(2):120-128 (2005).

Wellen, K.E. and G.S. Hotamisligil, Inflammation, stress, and diabetes. J Clin Invest 115(5): 1111-9 (2005).

PCT/US07/088411 Notification of Transmittal of International Search Report and Written Opinion of International Searching Authority dated Sep. 26, 2008.

Anathapuram, V., et al, Interleukin-1 Receptor Antagonist Synthesis by Peripheral Blood Mononuclear Cells: A Novel Predictor of Morbidity among Hemodialysis Patients. J Am Soc Nephrol 11: 2114-2121 (2000).

Cheung, The new cardiovascular continuum. Hong Kong Med J 12(2): 161-163 (2006).

Donath, Modulation of inflammatory markers in diabetes, Abstract, 42nd EASD Annual Meeting (2006).

Maedler, K., et al., Beta-Cells in Type2 Diabetes: A Loss of Function and Mass. Horm Res 62(supple 3): 67-73 (2004).

Mandrup-Poulsen, Thomas, et al., Involvement of Interleukin 1 and Interleukin 1 Antagonist in Pancreatic Beta-Cell Destruction in Insulin-Dependent Diabetes Mellitus. Cytokine 5(3): 185-191 (1993).

Sandberg, J.O. et al., Interleukin-1 Receptor Antagonist Prevents Low Dose Streptozotocin Induced Diabetes In Mice, BioChem BioPhys Resrch Comm 202(1): 543-548 (1994).

* cited by examiner

Figure 6

| Stimulant | Ab | IL-1β | IL-1a | IL-6 | IL-8 | IL-1Ra | TNFα | IFNγ |
|---|---|---|---|---|---|---|---|---|
| RPMI | 0 | 0.0 | 0.0 | 0.0 | 0.1 | 0.0 | 0.0 | 1.1 |
| RPMI | 10000 | 0.0 | 0.0 | 0.0 | 13.4 | 22.0 | 0.0 | 0.8 |
| Staph | 10000 | 0.0 | 31.7 | 45.6 | 93.6 | 79.7 | 52.6 | 22.1 |
| Staph | 1000 | 0.0 | 30.7 | 49.4 | 85.9 | 94.8 | 74.0 | 26.7 |
| Staph | 100 | 0.9 | 40.8 | 74.1 | 97.1 | 92.6 | 69.5 | 34.9 |
| Staph | 10 | 18.4 | 46.9 | 80.4 | 97.9 | 93.3 | 94.9 | 36.9 |
| Staph | 3 | 23.8 | 41.1 | 71.3 | 93.7 | 101.2 | 97.3 | 43.8 |
| Staph | 1 | 26.4 | 49.6 | 69.8 | 98.0 | 95.7 | 96.1 | 48.7 |
| Staph | 0.1 | 56.1 | 63.3 | 75.1 | 103.6 | 102.5 | 101.0 | 54.8 |
| Staph | 0 | 100.0 | 100.0 | 100.0 | 100.0 | 100.0 | 100.0 | 100.0 |

SEQUENCE LISTING

```
<160> NUMBER OF SEQ ID NOS: 6

<210> SEQ ID NO 1
<211> LENGTH: 23
<212> TYPE: PRT
<213> ORGANISM: Artificial Sequence
<220> FEATURE:
<223> OTHER INFORMATION: IL-1Beta Epitope

<400> SEQUENCE: 1

Glu Ser Val Asp Pro Lys Asn Tyr Pro Lys Lys Lys Met Glu Lys Arg
1               5                   10                  15

Phe Val Phe Asn Lys Ile Glu
            20

<210> SEQ ID NO 2
<211> LENGTH: 5
<212> TYPE: PRT
<213> ORGANISM: Artificial Sequence
<220> FEATURE:
<223> OTHER INFORMATION: linker peptide

<400> SEQUENCE: 2

Gly Gly Gly Gly Ser
1               5

<210> SEQ ID NO 3
<211> LENGTH: 107
<212> TYPE: PRT
<213> ORGANISM: Artificial Sequence
<220> FEATURE:
<223> OTHER INFORMATION: AB5-LC

<400> SEQUENCE: 3

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80
```

Glu Asp Ile Ala Thr Tyr Phe Cys Leu Gln Gly Lys Met Leu Pro Trp
                85                  90                  95

Thr Phe Gly Gly Gly Thr Lys Leu Glu Ile Lys
            100                 105

<210> SEQ ID NO 4
<211> LENGTH: 120
<212> TYPE: PRT
<213> ORGANISM: Artificial Sequence
<220> FEATURE:
<223> OTHER INFORMATION: AB5-HC

<400> SEQUENCE: 4

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Thr Gln Leu Thr Ile Ser Lys Asp Thr Ser Arg Asn Gln Val
65                  70                  75                  80

Phe Leu Lys Ile Thr Ser Val Asp Thr Val Asp Thr Ala Thr Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: AB7-LC

<400> SEQUENCE: 5

Asp Ile Gln Met Thr Gln Ser Thr Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Lys Ala Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Gln
65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Glu Ile Lys
            100                 105

<210> SEQ ID NO 6
<211> LENGTH: 120
<212> TYPE: PRT
<213> ORGANISM: Artificial Sequence
<220> FEATURE:
<223> OTHER INFORMATION: AB7-HC

```
                       -continued
<400> SEQUENCE: 6

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
            115                 120
```

METHODS FOR THE TREATMENT OF IL-1β RELATED DISEASES

This application claims benefit under 35 U.S.C. §119 of U.S. Provisional Application No. 60/871,046, filed Dec. 20, 2006, 60/908,389, filed Mar. 27, 2007, and 60/911,033, filed Apr. 10, 2007, the disclosures of which are herein incorporated by reference in their entirety.

FIELD OF INVENTION

The invention relates to methods for the treatment and/or prevention of Type 2 diabetes, obesity, hyperglycemia, hyperinsulinemia, Type 1 diabetes, insulin resistance and disease states and conditions characterized by insulin resistance. Such methods may be used to treat a mammalian subject suffering from Type 2 diabetes, obesity, hyperglycemia, hyperinsulinemia, Type 1 diabetes, insulin resistance and disease states and conditions characterized by insulin resistance or to prevent occurrence of the same in an at risk subject.

BACKGROUND OF THE INVENTION

The present disclosure is directed to methods for the treatment and/or prevention in mammals of Type 2 diabetes, obesity, hyperglycemia, hyperinsulinemia, Type 1 diabetes, insulin resistance and disease states and conditions characterized by insulin resistance. Such methods may be used to treat a mammalian (e.g., human) subject suffering from Type 2 diabetes, obesity, hyperglycemia, hyperinsulinemia, Type 1 diabetes, insulin resistance and disease states and conditions characterized by insulin resistance or to prevent occurrence of the same in an at risk subject.

Diabetes mellitus is a metabolic disorder in humans with a prevalence of approximately one percent in the general population (Foster, D. W., Harrison's Principles of Internal Medicine, Chap. 114, pp. 661-678, 10th Ed., McGraw-Hill, New York). The disease manifests itself as a series of hormone-induced metabolic abnormalities that eventually lead to serious, long-term and debilitating complications involving several organ systems including the eyes, kidneys, nerves, and blood vessels. Pathologically, the disease is characterized by lesions of the basement membranes, demonstrable under electron microscopy. Diabetes mellitus can be divided into two clinical syndromes, Type 1 and Type 2 diabetes mellitus. Type 1, or insulin-dependent diabetes mellitus (IDDM), also referred to as the juvenile onset form, is a chronic autoimmune disease characterized by the extensive loss of beta cells in the pancreatic Islets of Langerhans, which produce insulin. As these cells are progressively destroyed, the amount of secreted insulin decreases, eventually leading to hyperglycemia (abnormally high level of glucose in the blood) when the amount of secreted insulin drops below the normally required blood glucose levels. Although the exact trigger for this immune response is not known, patients with IDDM have high levels of antibodies against proteins expressed in pancreatic beta cells. However, not all patients with high levels of these antibodies develop IDDM.

Type 1 diabetics characteristically show very low or immeasurable plasma insulin with elevated glucagon. Regardless of what the exact etiology is, most Type 1 patients have circulating antibodies directed against their own pancreatic cells including antibodies to insulin, to islet of Langerhans cell cytoplasm and to the enzyme glutamic acid decarboxylase. An immune response specifically directed against beta cells (insulin producing cells) leads to Type 1 diabetes. The current treatment for Type 1 diabetic patients is the injection of insulin, and may also include modifications to the diet in order to minimize hyperglycemia resulting from the lack of natural insulin, which in turn, is the result of damaged beta cells. Diet is also modified with regard to insulin administration to counter the hypoglycemic effects of the hormone.

Type 2 diabetes (also referred to as non-insulin dependent diabetes mellitus (NIDDM), maturity onset form, adult onset form) develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing insulin output. Over time, these cells become unable to produce enough insulin to maintain normal glucose levels, indicating progression to Type 2 diabetes. Type 2 diabetes is brought on by a combination of genetic and acquired risk factors, including a high-fat diet, lack of exercise, and aging. Greater than 90% of the diabetic population suffers from Type 2 diabetes and the incidence continues to rise, becoming a leading cause of mortality, morbidity and healthcare expenditure throughout the world (Amos et al., Diabetic Med. 14:S1-85, 1997).

Type 2 diabetes is a complex disease characterized by defects in glucose and lipid metabolism. Typically there are perturbations in many metabolic parameters including increases in fasting plasma glucose levels, free fatty acid levels and triglyceride levels, as well as a decrease in the ratio of HDL/LDL. As discussed above, one of the principal underlying causes of diabetes is thought to be an increase in insulin resistance in peripheral tissues, principally muscle and fat. The causes of Type 2 diabetes are not well understood. It is thought that both resistance of target tissues to the action of insulin and decreased insulin secretion ("β-cell failure") occur. Major insulin-responsive tissues for glucose homeostasis are liver, in which insulin stimulates glycogen synthesis and inhibits gluconeogenesis; muscle, in which insulin stimulates glucose uptake and glycogen stimulates glucose uptake and inhibits lipolysis. Thus, as a consequence of the diabetic condition, there are elevated levels of glucose in the blood, which can lead to glucose-mediated cellular toxicity and subsequent morbidity (nephropathy, neuropathy, retinopathy, etc.). Insulin resistance is strongly correlated with the development of Type 2 diabetes.

Currently, there are various pharmacological approaches for the treatment of Type 2 diabetes (Scheen et al., Diabetes Care, 22(9):1568-1577, 1999). They act via different modes of action: 1) sulfonylureas (e.g., glimepiride, glisentide, sulfonylurea, AY31637) essentially stimulate insulin secretion; 2) biguanides (e.g., metformin) act by promoting glucose utilization, reducing hepatic glucose production and diminishing intestinal glucose output; 3) alpha-glucosidase inhibitors (e.g. acarbose, miglitol) slow down carbohydrate digestion and consequently absorption from the gut and reduce postprandial hyperglycemia; 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054) enhance insulin action, thus promoting glucose utilization in peripheral tissues; 5) glucagon-like-peptides including DPP4 inhibitors (e.g., sitagliptin); and 6) insulin stimulates tissue glucose utilization and inhibits hepatic glucose output. The above mentioned pharmacological approaches may be utilized individually or in combination therapy. However, each approach has its limitations and adverse effects. Over time, a large percentage of Type 2 diabetic subjects lose their response to these agents.

Insulin treatment is typically instituted after diet, exercise, and oral medications have failed to adequately control blood glucose. The drawbacks of insulin treatment are the need for drug injection, the potential for hypoglycemia, and weight gain.

IL-1β is a pro-inflammatory cytokine secreted by a number of different cell types including monocytes and macrophages. When released as part of an inflammatory reaction, IL-1β produces a range of biological effects, mainly mediated through induction of other inflammatory mediators such as corticotrophin, platelet factor-4, prostaglandin E2 (PGE2), IL-6, and IL-8. IL-1β induces both local and systemic inflammatory effects through the activation of the IL-1 receptor found on almost all cell types. The interleukin-1 (IL-1) family of cytokines has been implicated in a number of disease states. IL-1 family members include IL-1α, IL-1β, and IL-1Ra. Although related by their ability to bind to IL-1 receptors (IL-1R1 and IL-1R2), each of these cytokines is different, being expressed by a different gene and having a different primary amino acid sequence. Furthermore, the physiological activities of these cytokines can be distinguished from each other. Experiments indicating the apparent involvement of IL-1β in diabetes have been published.

Maedler et al, J Clin Invest (2002) 110:851-860 suggested that in Type 2 diabetes chronic hyperglycemia can be detrimental to pancreatic β-cells, causing impaired insulin secretion, and noted that IL-1β is a proinflammatory cytokine acting during the autoimmune process of type 1 diabetes, and inhibits β cell function. In particular, they tested the hypothesis that IL-1β may mediate the deleterious effects of high glucose levels. Treatment of diabetic animals with phlorizin normalized plasma glucose and prevented β cell expression of IL-1β. This was said to implicate an inflammatory process in the pathogenesis of glucotoxicity in type 2 diabetes, and they identified the IL-1β/NF-$_κ$B pathway as a target to preserve β cell mass and function in this condition.

Donath et al, J Mol med (2003) 81:455-470 noted the apparent significance of IL-1β in the pathway to apoptosis of pancreatic islet β-cell death, leading to insulin deficiency and diabetes, and proposed anti-inflammatory therapeutic approaches designed to block β-cell apoptosis in Type 1 and 2 diabetes.

WO 2004/002512 is directed to the use of an IL-1 receptor antagonist (IL-1Ra) and/or pyrrolidine dithiocarbamate (PDTC) for the treatment or prophylaxis of type 2 diabetes. However, the frequent dosing suggested for therapeutic use of IL-Ra polypeptide in the treatment of Type 2 diabetes (injection every 24 hours) may result in problems with patient compliance, thereby decreasing effectiveness of this treatment modality and/or limiting its desirability. Thus, there remains a need for effective means to treat Type 2 diabetes, particularly those that do not require daily injections.

Larsen et al, New England Journal of Medicine (2007) 356:1517-1526 describes the use of a recombinant IL-1 receptor antagonist (IL-1Ra, anakinra) for the treatment of type 2 diabetes mellitus. However, the dosing of 100 mg of anakinra once daily for 13 weeks may result in problems with patient compliance, thereby decreasing effectiveness of this treatment modality/or limiting its desirability. Thus, there remains a need for effective means to treat Type 2 diabetes, particularly treatment means that do not require frequent (e.g., daily) injections.

US 2005/0256197 and US 2005/0152850 are directed to a method for facilitating metabolic control (e.g., glucose) in a subject (e.g., subject with diabetes), comprising decreasing the level of IL-1β in gingival crevicular fluid of the subject such that the level of circulating TNF is decreased, particularly by using an anti-inflammatory agent, such as an anti-inflammatory ketorolac oral rinse.

Obesity is a chronic disease that is highly prevalent and is associated not only with a social stigma, but also with decreased life span and numerous medical problems including adverse psychological development, dermatological disorders such as infections, varicose veins, exercise intolerance, diabetes mellitus, insulin resistance, hypertension, hypercholesterolemia, and coronary heart disease (Rissanen et al., British Medical Journal, 301: 835-837, 1990). Obesity is highly correlated with insulin resistance and diabetes in experimental animals and humans. Indeed, obesity and insulin resistance, the latter of which is generally accompanied by hyperinsulinemia or hyperglycemia, or both, are hallmarks of Type 2 diabetes. In addition, Type 2 diabetes is associated with a two- to four-fold risk of coronary artery disease. Despite decades of research on these serious health problems, the etiology of obesity and insulin resistance is unknown.

Insulin resistance is associated with a number of disease states and conditions and is present in approximately 30-40% of non-diabetic individuals. These disease states and conditions include, but are not limited to, pre-diabetes and metabolic syndrome (also referred to as insulin resistance syndrome). Pre-diabetes is a state of abnormal glucose tolerance characterized by either impaired glucose tolerance (IGT) or impaired fasting glucose (IFG). Patients with pre-diabetes are insulin resistant and are at high risk for future progression to overt Type 2 diabetes. Metabolic syndrome is an associated cluster of traits that include, but is not limited to, hyperinsulinemia, abnormal glucose tolerance, obesity, redistribution of fat to the abdominal or upper body compartment, hypertension, dysfibrinolysis, and a dyslipidemia characterized by high triglycerides, low HDL-cholesterol, and small dense LDL particles. Insulin resistance has been linked to each of the traits, suggesting metabolic syndrome and insulin resistance are intimately related to one another. The diagnosis of metabolic syndrome is a powerful risk factor for future development of Type 2 diabetes, as well as accelerated atherosclerosis resulting in heart attacks, strokes, and peripheral vascular disease. Inflammatory cytokines, including IL-1, have been shown to mediate inflammation within adipose tissue which appears to be involved in insulin resistance of adipocytes (Trayhurn et al., Br. J. Nutr. 92:347-355, 2004; Wisse, J. Am. Soc. Nephrol. 15:2792-2800, 2004; Fantuzzi, J. Allergy Clin. Immunol. 115:911-919, 2005; Matsuzawa, FEBS Lett. 580:2917-2921, 2006; Greenberg et al., Eur J. Clin. Invest. 32 Suppl.3:24-34, 2002; Jager et al., Endocrinology 148:241-251, 2007). Adipocytes are cells that store fat and secrete adipokines (i.e., a subset of cytokines) and are a major component of adipose tissue. Macrophages, which are inflammatory cells and the main producers of the inflammatory cytokines, IL-1, TNF-α, and IL-6, also exist within adipose tissue, especially inflamed adipose associated with obesity (Kern et al., Diabetes 52:1779-1785, 2003). TNF-α and IL-6 have been known previously to desensitize adipocytes to insulin stimulation (i.e., insulin resistance).

Because of the problems with current treatments, new therapies to treat Type 2 diabetes and other disease indications such as those disclosed herein are needed to replace or complement available pharmaceutical approaches. The present invention provides a method for treatment of Type 2 diabetes. In addition, the present invention also provides a method for treating obesity, hyperglycemia, hyperinsulinemia, Type 1 diabetes, insulin resistance and disease states and conditions characterized by insulin resistance. The methods disclosed herein comprise, for example, administering an anti-IL-1β antibody or fragment thereof. Methods that directly target the IL-1β ligand with an antibody, particularly antibodies that exhibit high affinity, provide advantages over other potential methods of treatment, such as IL-1β receptor antagonists (e.g., IL-1Ra, Anakinra, Kineret®). The challenge for IL-1 receptor antagonist-based therapeutics is the need for such therapeutics to occupy a large number of receptors, which is a formidable task since these receptors are widely expressed on all cells except red blood cells (Dinarello, Curr. Opin. Pharmacol. 4:378-385, 2004). In most immune-mediated diseases, such as the diseases disclosed herein, the amount of IL-1β cytokine that is measurable in body fluids or associated with activated cells is relatively low. Thus, a method of treatment and/or prevention that directly targets the IL-1β ligand is a superior strategy, particularly when administering an IL-1β antibody with high affinity.

SUMMARY OF THE INVENTION

The present disclosure is directed to methods for the treatment and/or prevention in mammals of Type 2 diabetes, obesity, hyperglycemia, hyperinsulinemia, decreased insulin production, Type 1 diabetes, insulin resistance and/or disease states and conditions characterized by insulin resistance. Such methods may be used to treat a mammalian (e.g., human) subject suffering from or at risk for diabetes, obesity, hyperglycemia, hyperinsulinemia, decreased insulin production, insulin resistance and/or disease states and conditions characterized by insulin resistance. The methods also may be used to prevent the occurrence of Type 2 diabetes, Type 1 diabetes, obesity, hyperglycemia, hyperinsulinemia, decreased insulin production, insulin resistance and disease states and conditions characterized by insulin resistance in an at risk subject.

In one aspect, the invention is a method of treating in a human, a disease or condition selected from the group consisting of Type 2 diabetes, hyperglycemia, hyperinsulinemia, obesity, decreased insulin production, Type 1 diabetes, and insulin resistance, the method comprising administering an anti-IL-1β antibody or fragment thereof to the human. In a preferred embodiment, the disease or condition is selected from the group consisting of Type 2 diabetes, hyperglycemia, hyperinsulinemia, obesity, decreased insulin production, and insulin resistance. Preferably, the disease or condition is Type 2 diabetes, obesity, decreased insulin production, or insulin resistance. More preferably the disease or condition is Type 2 diabetes, obesity, or insulin resistance. Most preferably the disease or condition is Type 2 diabetes. In one embodiment, the method does not augment a cardiovascular disease or condition. In certain embodiments, the antibody or fragment is used to treat two or more of the aforementioned diseases or conditions in the same patient (e.g., human subject).

In another aspect, the invention provides a method for treating or preventing a disease or condition by administering an anti-IL-1β antibody or fragment, wherein the disease or condition is pre-diabetes, dyslipidemia, hyperlipidemia, hypertension, metabolic syndrome or sickness behavior. In yet another aspect, the method reduces or prevents in a human a complication or condition associated with Type 2 diabetes selected from the group consisting of retinopathy, renal failure, cardiovascular disease, and wound healing, the method comprising administering an anti-IL-1β antibody or fragment thereof to the human. In certain embodiments, the antibody or fragment is used to treat two or more of the aforementioned diseases or conditions in the same patient (e.g., human subject). In another embodiment, the antibody or fragment is used to treat renal failure (e.g., renal disease) that may result from a condition other than Type 2 diabetes. In yet another embodiment, the antibody or fragment is used to decrease the level of C-reactive protein (CRP) in a subject exhibiting elevated levels of CRP.

In another aspect, the invention provides IL-1β antibodies or antibody fragments thereof for use in treating or preventing a disease or condition as disclosed herein. In a further aspect, the invention provides IL-1β antibodies or antibody fragments thereof for use in treating or preventing a disease or conditions selected from the group consisting of Type 2 diabetes, obesity, decreased insulin production, and insulin resistance. In yet another aspect, the invention provides IL-1β antibodies or antibody fragments thereof for use in treating or preventing Type 2 diabetes.

In another aspect, the invention provides pharmaceutical compositions comprising IL-1β antibodies or antibody fragments thereof and optionally at least one pharmaceutically acceptable excipient for use in treating or preventing a disease or condition as disclosed herein. In a further aspect, the invention provides pharmaceutical compositions comprising IL-1β antibodies or antibody fragments thereof and optionally at least one pharmaceutically acceptable excipient for use in treating or preventing a disease or conditions selected from the group consisting of Type 2 diabetes, obesity, decreased insulin production, and insulin resistance. In yet another aspect, the invention provides pharmaceutical compositions comprising IL-1β antibodies or antibody fragments thereof and optionally at least one pharmaceutically acceptable excipient for use in treating or preventing Type 2 diabetes.

The anti-IL-1β antibodies or antibody fragments used in the methods of the invention generally bind to IL-1β with high affinity. In preferred embodiments, the antibody or antibody fragment binds to IL-1β with a dissociation constant of about 10 nM or less, about 5 nM or less, about 1 nM or less, about 500 pM or less, about 250 pM or less, about 100 pM or less, about 50 pM or less, or about 25 pM or less. In particularly preferred embodiments, the antibody or antibody fragment binds to human IL-1β with a dissociation constant of about 100 pM or less, about 50 pM or less, about 10 pM or less, about 5 pM or less, about 3 pM or less, about 1 pM or less, about 0.75 pM or less, about 0.5 pM or less, about 0.3 pM or less, about 0.2 pM or less, or about 0.1 pM or less. In particularly preferred embodiments, the antibody or antibody fragment binds to human IL-1β with a dissociation constant of about 10 pM or less.

In another aspect of the invention, the anti-IL-1β antibody or antibody fragment is a neutralizing antibody. In another aspect, the anti-IL-1β antibody or antibody fragment binds to an IL-1β epitope such that the bound antibody or fragment substantially permits the binding of IL-1β to IL-1 receptor I (IL-1RI). In another aspect, the anti-IL-1β antibody or antibody fragment binds to IL-1β, but does not substantially prevent the bound IL-1β from binding to IL-1 receptor I (IL-1RI). In another aspect, the antibody or antibody fragment does not detectably bind to IL-1α, IL-1R or IL-1Ra. In yet another aspect of the invention, the antibody or antibody fragment binds to an epitope contained in the sequence ESVDPKNYPKKKMEKRFVFNKIE (SEQ ID NO: 1). In yet another aspect of the invention, the antibody or antibody fragment binds to an epitope incorporating Glu64 of IL-1β. In yet another aspect of the invention, the antibody or antibody fragment binds to amino acids 1-34 of the N terminus of IL-1β. Preferably, the antibody or antibody fragment is human engineered, humanized or human.

In another aspect, the invention provides a method of treating a human displaying symptoms of, or at risk for, developing any of the aforementioned diseases or conditions (e.g., Type 1 diabetes, Type 2 diabetes, hyperglycemia, hyperinsulinemia, obesity, decreased insulin production, insulin resistance), the method comprising administering an anti-IL-1β antibody or fragment thereof to the human in one or more doses.

In another aspect of the invention, a method is provided for treating in a human, a disease or condition selected from the group consisting of Type 1 diabetes, Type 2 diabetes, hyperglycemia, hyperinsulinemia, obesity, decreased insulin production, and insulin resistance, the method comprising administering an anti-IL-1β antibody or fragment thereof to the human, wherein administration of an initial dose of the IL-1β antibody or antibody fragment is followed by the administration of one or more subsequent doses. In one embodiment, administration of an initial dose of the antibody or antibody fragment is followed by the administration of two or more subsequent doses. In another embodiment, administration of an initial dose of the antibody or antibody fragment is followed by the administration of one or more subsequent doses, and wherein said one or more subsequent doses are in an amount that is approximately the same or less than the initial dose. In another embodiment, administration of an initial dose of the antibody or antibody fragment is followed by the administration of one or more subsequent doses, and wherein at least one of the subsequent doses is in an amount that is more than the initial dose.

In one embodiment, two or more, three or more, four or more, five or more, six or more, seven or more, eight or more, nine or more, ten or more or eleven or more subsequent doses of the antibody are administered. In another embodiment administration of the initial dose and each one or more subsequent doses are separated from each other by an interval of at least about two weeks, at least about three weeks, at least about one month, at least about two months, at least about three months, at least about four months, at least about five months, at least about six months, at least about seven months, at least about eight months, at least about nine months, at least about ten months, at least about eleven months, or at least about twelve months.

In another embodiment, the antibody or fragment is administered in one or more doses of 5 mg/kg or less of antibody or fragment, 3 mg/kg or less of antibody or fragment, 2 mg/kg or less of antibody or fragment, 1 mg/kg or less of antibody or fragment, 0.75 mg/kg or less of antibody or fragment, 0.5 mg/kg or less of antibody or fragment, 0.3 mg/kg or less of antibody or fragment, 0.1 mg/kg or less of antibody or fragment, or 0.03 mg/kg or less of antibody or fragment. Preferably, in each of the aforementioned embodiments, the antibody or fragment is administered in one or more doses of at least 0.01 mg/kg of antibody or fragment, at least, 0.03 mg/kg of antibody or fragment, at least 0.05 mg/kg of antibody or fragment, or at least 0.09 mg/kg of antibody or fragment. The above dosage amounts refer to mg (antibody or fragment)/kg (weight of the individual to be treated).

In another embodiment, the initial dose and one or more subsequent doses of antibody or fragment are each from about 0.01 mg/kg to about 10 mg/kg of antibody, from about 0.05 to about 5 mg/kg of antibody, from about 0.05 mg/kg to about 3 mg/kg of antibody, from about 0.1 mg/kg to about 3 mg/kg of antibody, from about 0.1 mg/kg to about 1 mg/kg of antibody, from about 0.1 mg/kg to about 0.5 mg/kg of antibody, from about 0.3 mg/kg to about 5 mg/kg of antibody, from about 0.3 mg/kg to about 3 mg/kg of antibody, from about 0.3 mg/kg to about 1 mg/kg of antibody, from about 0.5 mg/kg to about 5 mg/kg of antibody, from about 0.5 mg/kg to about 3 mg/kg of antibody, from about 0.5 mg/kg to about 1 mg/kg of antibody, from about 1 mg/kg to about 5 mg/kg of antibody, or from about 1 mg/kg to about 3 mg/kg of antibody.

In certain embodiments, two or more, three or more, four or more, five or more, six or more, seven or more, eight or more, nine or more, ten or more or eleven or more subsequent doses of the antibody are administered. The above dosage amounts refer to mg (antibody or fragment)/kg (weight of the individual to be treated). The same applies hereinafter if a dosage amount is mentioned.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human as an initial dose of about 5 mg/kg or less of antibody or fragment and a plurality of subsequent doses of antibody or fragment in an amount about the same or less than the initial dose, wherein the subsequent doses are separated by an interval of time of at least 2 weeks.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human as an initial dose of about 3 mg/kg or less of antibody or fragment and a plurality of subsequent doses of antibody or fragment in an amount about the same or less than the initial dose, wherein the subsequent doses are separated by an interval of time of at least 2 weeks.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human as an initial dose of about 1 mg/kg or less of antibody or fragment and a plurality of subsequent doses of antibody or fragment in an amount about the same or less than the initial dose, wherein the subsequent doses are separated by an interval of time of at least 2 weeks.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human as an initial dose of about 0.5 mg/kg or less of antibody or fragment and a plurality of subsequent doses of antibody or fragment in an amount about the same or less than the initial dose, wherein the subsequent doses are separated by an interval of time of at least 2 weeks.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human as an initial dose of about 0.3 mg/kg or less of antibody or fragment and a plurality of subsequent doses of antibody or fragment in an amount about the same or less than the initial dose, wherein the subsequent doses are separated by an interval of time of at least 2 weeks.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human as an initial dose of about 0.1 mg/kg or less of antibody or fragment and a plurality of subsequent doses of antibody or fragment in an amount about the same or less than the initial dose, wherein the subsequent doses are separated by an interval of time of at least 2 weeks.

Preferably, in the aforementioned embodiments wherein the antibody or fragment is administered as an initial dose and a plurality of subsequent doses, the dose of antibody or fragment is at least 0.01 mg/kg of antibody or fragment, at least, 0.03 mg/kg of antibody or fragment, at least 0.05 mg/kg of antibody or fragment, or at least 0.09 mg/kg of antibody or fragment.

In yet another aspect of the invention, the antibody or fragment is administered as a fixed dose, independent of a dose per subject weight ratio. In one embodiment, the antibody or fragment is administered in one or more fixed doses of 1000 mg or less of antibody or fragment, 750 mg or less of antibody or fragment, 500 mg or less of antibody or fragment, 250 mg or less of antibody or fragment, 100 mg or less of antibody or fragment, or about 25 mg or less of antibody or fragment. In another embodiment, the antibody or fragment is administered in one or more fixed doses of at least about 1 mg of antibody or fragment, at least about 5 mg of antibody or fragment, or at least about 10 mg of antibody or fragment.

In certain embodiments, the fixed dose is from about 1 mg to about 10 mg, about 1 mg to about 25 mg, about 10 mg to about 25 mg, about 10 mg to about 50 mg, about 10 mg to about 100 mg, about 25 mg to about 50 mg, about 25 mg to about 100 mg, about 50 mg to about 100 mg, about 50 mg to about 150 mg, about 100 mg to about 150 mg, about 100 mg to about 200 mg, about 150 mg to about 200 mg, about 150 mg to about 250 mg, about 200 mg to about 250 mg, about 200 mg to about 300 mg, about 250 mg to about 300 mg, about 250 mg to about 500 mg, about 300 mg to about 400 mg, about 400 mg to about 500 mg, about 400 mg to about 600 mg, about 500 mg to about 750 mg, about 600 mg to about 750 mg, about 700 mg to about 800 mg, about 750 mg to about 1000 mg. In a preferred embodiment, the fixed dose is selected from the group consisting of about 1 mg to about 10 mg, about 1 mg to about 25 mg, about 10 mg to about 25 mg, about 10 mg to about 100 mg, about 25 mg to about 50 mg, about 50 mg to about 100 mg, about 100 mg to about 150 mg, about 150 mg to about 200 mg, about 200 mg to about 250 mg.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human, wherein administration of an initial dose of the antibody or antibody fragment is followed by the administration of one or more subsequent doses, and wherein the plasma concentration of said antibody or antibody fragment in the human is permitted to decrease below a level of about 0.1 ug/mL for a period of time greater than about 1 week and less than about 6 months between administrations during a course of treatment with said initial dose and one or more subsequent doses. In one embodiment, the plasma concentration of said antibody or antibody fragment is permitted to decrease below a level of about 0.07 ug/mL, about 0.05 ug/mL, about 0.03 ug/mL or about 0.01 ug/mL for a period of time greater than about 1 week and less than about 5 months, about 4 months, about 3 months, about 2 months, about 1 month, about 3 weeks, or about 2 weeks between administrations. In one embodiment, these plasma values refer to values obtained for an individual that is treated with the antibody of fragment in accordance with the invention. In one embodiment, such an individual may be a patient suffering from one of the diseases mentioned hereinafter such as Type 2 diabetes.

The invention contemplates that an anti-IL-1β antibody or fragment used in accordance with the methods herein may be administered in any of the aforementioned dose amounts, numbers of subsequent administrations, and dosing intervals between administrations, and that any of the disclosed dose amounts, numbers of subsequent administrations, and dosing intervals between administrations may be combined with each other in alternative regimens to modulate the therapeutic benefit. In certain embodiments, the one or more subsequent doses are in an amount that is approximately the same or less than the first dose administered. In another embodiment, the one or more subsequent doses are in an amount that is approximately more than the first dose administered. Preferably the anti-IL-1β antibody or fragment is administered by subcutaneous, intramuscular or intravenous injection. The invention contemplates that each dose of antibody or fragment may be administered at one or more sites.

In another aspect, the invention provides a method of treating or preventing a disease or condition in a human using an anti-IL-1β antibody or antibody fragment, wherein the disease or condition is Type 2 diabetes, and wherein a dose of the antibody or fragment is sufficient to achieve at least a 0.5, at least a 1.0, at least a 1.5, at least a 2.0, at least a 2.5, or at least a 3.0 percentage point improvement in hemoglobin A1c. In one embodiment, these parameter values refer to values obtained for an individual that is treated with the antibody of fragment in accordance with the invention. In one embodiment, such an individual may be a patient suffering from one of the diseases mentioned hereinafter such as Type 2 diabetes.

In a preferred embodiment, the improvement in hemoglobin A1c is sufficient to meet regulatory guidelines for approval of therapeutic agents in Type 2 diabetes treatment. Assay methods for determination of hemoglobin A1c are well known in the art. The invention contemplates that the dose of antibody or fragment sufficient to achieve the improvement in hemoglobin A1c, may comprise any of the aforementioned dose amounts, numbers of subsequent administrations, and dosing intervals between administrations, as well as any combination of dose amounts numbers of subsequent administrations, and dosing intervals between administrations antibody or fragment described herein. Further, the improvement in hemoglobin A1c may be at a time-point at least about 1 month, about 2 months, about 3 months, about 4 months, or about 5 months, and preferably about 6 months or more, about 7 months or more, about 8 months or more, about 9 months or more, about 10 months or more, about 11 months or more, or about 12 months or more following an initial administration of one or more doses of antibody or fragment.

In another aspect of the aforementioned methods for treating or preventing Type 2 diabetes, the method is sufficient to achieve at least one of the following modifications: reduction in fasting blood sugar level, decrease in insulin resistance, reduction of hyperinsulinemia, improvement in glucose tolerance, reduction in C-reactive peptide (CRP), increased insulin production and reduction of hyperglycemia, reduction in the need for diabetes medication, reduction in BMI, change in glucose/insulin C-peptide AUC, reduction in urine glucose level, reduction in acute phase reactants, decrease in serum lipids with improvement in the lipid profile with respect to cardiovascular risk. Assay methods for determining any of the above modifications are well known in the art. Further, the invention contemplates that achievement of one of the aforementioned modifications may be at a time-point at least about 1 month, about 2 months, about 3 months, about 4 months, or about 5 months, and preferably at least about 6 months or more, about 7 months or more, about 8 months or more, about 9 months or more, about 10 months or more, about 11 months or more, or about 12 months or more following an initial administration of one or more doses of antibody or fragment.

In another aspect of the invention, the method provided herein reduces or prevents a complication or condition associated Type 2 diabetes selected from the group consisting of retinopathy, renal failure, cardiovascular disease, and wound healing, the method comprising administering an anti-IL-1β antibody or fragment thereof to the human. In one embodiment, the complication or condition is cardiovascular disease, and wherein said cardiovascular disease is atherosclerosis or peripheral vascular disease. In another embodiment, the complication or condition is wound healing, and wherein said wound healing condition is diabetic ulcer. In another aspect, the method prevents or delays end stage renal disease or diabetic neuropathy. In one embodiment, the anti-IL-1β antibody or fragment is administered in combination with at least one other medically accepted treatment for the disease, condition or complication. In another embodiment, the at least one other medically accepted treatment for the disease, condition or complication is reduced or discontinued, while treatment with the anti-IL-1β antibody or fragment is maintained at a constant dosing regimen. In another embodiment, the at least one other medically accepted treatment for the disease, condition or complication is reduced or discontinued, and treatment with the anti-IL-1β antibody or fragment is reduced. In another embodiment, the at least one other medically accepted treatment for the disease, condition or complication is reduced or discontinued, and treatment with the anti-IL-1β antibody or fragment is increased. In yet another embodiment, the at least one other medically accepted treatment for the disease, condition or complication is maintained and treatment with the anti-IL-1β antibody or fragment is reduced or discontinued. In yet another embodiment, the at least one other medically accepted treatment for the disease, condition or complication and treatment with the anti-IL-1β antibody or fragment are reduced or discontinued.

In another aspect of the invention, a method of reducing the amount of C-reactive protein in a subject is provided, the method comprising administering an anti-IL-1β antibody or fragment thereof to the subject. In one embodiment, the antibody or antibody fragment is administered in one or more doses of 1 mg/kg or less of antibody or fragment, 0.75 mg/kg or less of antibody or fragment, 0.5 mg/kg or less of antibody or fragment, 0.3 mg/kg or less of antibody or fragment, 0.1 mg/kg or less of antibody or fragment, or 0.03 mg/kg or less of antibody or fragment. Preferably, the antibody or fragment is administered in one or more doses of at least 0.01 mg/kg of antibody or fragment, at least, 0.03 mg/kg of antibody or fragment, at least 0.05 mg/kg of antibody or fragment, or at least 0.09 mg/kg of antibody or fragment. In another embodiment, the antibody or fragment is administered as one or more fixed doses, independent of a dose per subject weight ratio, of 500 mg or less of antibody or fragment, 250 mg or less of antibody or fragment, 100 mg or less of antibody or fragment, or about 25 mg or less of antibody or fragment. Preferably, the antibody or fragment is administered in one or more fixed doses of at least about 1 mg of antibody or fragment, at least about 5 mg of antibody or fragment, or at least about 10 mg of antibody or fragment. In another embodiment, the antibody or antibody fragment binds to IL-1β with a dissociation constant of about 500 pM or less, 250 pM or less, about 100 pM or less, about 50 pM or less, or about 25 pM or less, about 10 pM or less, about 5 pM or less, about 3 pM or less, about 1 pM or less, about 0.75 pM or less, about 0.5 pM or less, about 0.3 pM or less, about 0.2 pM or less, or about 0.1 pM or less. In another embodiment, administration of an initial dose is followed by administration of one or more subsequent doses, separated from each other by an interval of at least about two weeks, at least about three weeks, at least about one month, at least about two months, at least about three months, at least about four months, at least about five months, at least about six months, at least about seven months, at least about eight months, at least about nine months, at least about ten months, at least about eleven months, or at least about twelve months. In another embodiment, said method of reducing the amount of C-reactive protein in a subject is provided, wherein the subject is suffering from a renal disease (e.g., chronic renal disease, renal failure). In another embodiment, the subject is suffering from Type 2 diabetes, Type 1 diabetes, obesity, hyperglycemia, hyperinsulinemia, decreased insulin production, insulin resistance and/or disease states and conditions characterized by insulin resistance. In another embodiment, the subject is suffering from a disease or condition of pre-diabetes, dyslipidemia, hyperlipidemia, hypertension, metabolic syndrome or sickness behavior. The above dosage amounts refer to mg (antibody or fragment)/kg (weight of the individual to be treated). Administration of the antibodies or fragments with the aforementioned dissociation constants may be performed according to any of the aforementioned dose amounts and dosing intervals (when administering two or more doses).

In another aspect, methods provided herein are in conjunction with at least one additional treatment method, said additional treatment method comprising administering at least one pharmaceutical composition comprising an active agent other than an IL-1β antibody or fragment. In yet another aspect, the methods prevent or delay the need for at least one additional treatment method, said additional treatment method comprising administering at least one pharmaceutical composition comprising an active agent other than an IL-1β antibody or fragment. In still another aspect, the methods reduce the amount, frequency or duration of at least one additional treatment method, said additional treatment method comprising administering at least one pharmaceutical composition comprising an active agent other than an IL-1β antibody or fragment. In one embodiment, the at least one pharmaceutical composition comprising an active agent other than an IL-1β antibody or fragment is selected from the group consisting of a sulfonylurea, a meglitinide, a biguanide, an alpha-glucosidase inhibitor, a thiazolidinedione, a glucagon-like peptide, and insulin. In another embodiment, the active agent is a sulfonylurea. In another embodiment, the active agent is a meglitinide. In another embodiment, the active agent is a biguanide. In another embodiment, the active agent is an alpha-glucosidase inhibitor. In another embodiment, the active agent is a thiazolidinedione. In another embodiment, the active agent is a glucagon-like peptide. In another embodiment, the active agent is insulin. In another embodiment, the at least one pharmaceutical composition comprising an active agent, comprises two active agents. In one embodiment, the two active agents are a sulfonylurea and a biguanide. In another embodiment, the two active agents are a thiazolidinedione and a biguanide. In yet another embodiment, treatment with the at least one active agent is maintained. In another embodiment, treatment with the at least one active agent is reduced or discontinued, while treatment with the anti-IL-1β antibody or fragment is maintained at a constant dosing regimen. In another embodiment, treatment with the at least one active agent is reduced or discontinued and treatment with the anti-IL-1β antibody or fragment is reduced. In another embodiment, treatment with the at least one active agent is reduced or discontinued, and treatment with the anti-IL-1β antibody or fragment is increased. In yet another embodiment, treatment with the at least one active agent is maintained and treatment with the anti-IL-1β antibody or fragment is reduced or discontinued. In yet another embodiment, treatment with the at least one active agent and treatment with the anti-IL-1β antibody or fragment are reduced or discontinued.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human, wherein administration of an initial dose of the antibody or antibody fragment is followed by the administration of one or more subsequent doses, and wherein the plasma concentration of said antibody or antibody fragment in the human is maintained at a level of at least about 0.03 ug/mL, at least about 0.05 ug/mL, at least about 0.08 ug/mL, at least about 0.1 ug/mL, at least about 0.15 ug/mL, at least about 0.2 ug/mL, at least about 0.25 ug/mL, at least about 0.3 ug/mL, at least about 0.4 ug/mL, at least about 0.5 ug/mL, at least about 0.6 ug/mL, at least about 0.8 ug/mL, at least about 1 ug/mL, at least about 1.5 ug/mL, at least about 2 ug/mL, at least about 3 ug/mL, at least about 4 ug/mL, or at least about 5 ug/mL during a course of treatment with said initial dose and one or more subsequent doses. In one embodiment, these plasma values refer to values obtained for an individual that is treated with the antibody of fragment in accordance with the invention. In one embodiment, such an individual may be a patient suffering from one of the diseases mentioned hereinafter such as Type 2 diabetes.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human, wherein administering the anti-IL-1β antibody or fragment thereof to the human results in a decrease in the production of one or more gene products selected from the group consisting of leptin, resistin, visfatin, RANTES, IL-6, MCP-1, PAI-1, acylation-stimulating protein, SAA3, Pentraxin-3, macrophage migration inhibition factor, IL-1RA, IL-12, IL-8 and TNF-α. In one embodiment, administering the anti-IL-1β antibody or fragment thereof to the human results in a decrease in the production of one or more gene products selected from the group consisting of leptin, resistin, and visfatin. In another embodiment, administering the anti-IL-1β antibody or fragment thereof to the human results in a decrease in the production of one or more gene products selected from the group consisting of MCP-1, RANTES, IL-6, TNF-α, and Pentraxin-3. In yet another embodiment, said decrease in the production of one or more gene products is from adipose tissue. In yet another embodiment, said decrease is detected in the blood of the human.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human, wherein administering the anti-IL-1β antibody or fragment thereof to the human results in an increase in the production of adiponectin. In one embodiment, said increase in the production of adiponectin is from adipose tissue. In another embodiment, said increase is detected in the blood of the human.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human, wherein the antibody or fragment thereof has a lower $IC_{50}$ than an IL-1β receptor antagonist in a human whole blood IL-1β inhibition assay that measures IL-1β induced production of IL-8. In one embodiment, the antibody or fragment has an $IC_{50}$ that is less than about 90%, 80%, 70%, 60%, 50% of the $IC_{50}$ of an IL-1β receptor antagonist in a human whole blood IL-1β inhibition assay that measures IL-1β induced production of IL-8. In a further embodiment, the antibody or fragment has an $IC_{50}$ that is less than about 40%, 30%, 20%, 10% of the $IC_{50}$ of an IL-1β receptor antagonist in a human whole blood IL-1β inhibition assay that measures IL-1β induced production of IL-8. In a preferred embodiment, the antibody or fragment has an $IC_{50}$ that is less than about 8%, 5%, 4%, 3%, 2%, 1% of the $IC_{50}$ of an IL-1β receptor antagonist in a human whole blood IL-1β inhibition assay that measures IL-1β induced production of IL-8. In one embodiment, the IL-1β receptor antagonist is anakinra (i.e., Kineret®).

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human, wherein the antibody or fragment thereof provides in vivo inhibition of IL-1β stimulated release of IL-6 in mice compared to a control antibody using an assay that is described by Economides et al., *Nature Med.*, 9:47-52 (2003) which is incorporated by reference. In one embodiment the antibody or fragment provides in vivo inhibition of IL-1β stimulated release of IL-6 in mice of at least about 10%, 20%, 30%, 40%, 50% compared to the control antibody. In a further embodiment, the antibody or fragment provides in vivo inhibition of IL-1β stimulated release of IL-6 in mice of at least about 60%, 70%, 80%, 90%, 95% compared to the control antibody. In one embodiment, the control antibody is an isotype control antibody.

In another aspect, the invention provides a method of treating in a human, a disease or condition selected from the group consisting of Type 1 diabetes, Type 2 diabetes, hyperglycemia, hyperinsulinemia, obesity, decreased insulin production, and insulin resistance, the method comprising administering a therapeutically effective amount of an anti-IL-1β antibody or fragment thereof to the human, wherein the antibody or fragment thereof inhibits *Staphylococcus epidermidis* induced cytokine production in human whole blood compared to a control where no antibody is used. In one embodiment the antibody or fragment provides a greater level of inhibition of *Staphylococcus epidermidis* induced cytokine production in human whole blood by at least about 10%, 20%, 30%, 40%, 50% compared to the control. In a further embodiment, the antibody or fragment provides a greater level of inhibition of *Staphylococcus epidermidis* induced cytokine production in human whole blood by at least about 60%, 70%, 80%, 90%, 95% compared to the control. In one embodiment, the inhibited cytokines are IL-1β, IL-1a, IL-6, IL-8, IL-1Ra, TNFα or IFNγ.

In another aspect, the invention discloses the use of an anti-IL-1β antibody or fragment thereof which as a lower $IC_{50}$ than an IL-1β receptor antagonist in a human whole blood IL-1β inhibition assay that measures IL-1β induced production of IL-8, in the manufacture of a composition for use in the treatment of Type 1 diabetes, Type 2 diabetes, hyperglycemia, hyperinsulinemia, obesity, decreased insulin production, and insulin resistance. In one embodiment, the IL-1β receptor antagonist is anakinra (i.e., Kineret®)

In another aspect of the invention, the use of the IL-1β antibodies or binding fragments is contemplated in the manufacture of a medicament for treating or preventing a disease or condition as disclosed herein. In any of the uses, the medicament can be coordinated with treatment using a second active agent. In another embodiment of the invention, the use of a synergistic combination of an antibody of the invention for preparation of a medicament for treating a patient exhibiting symptoms of at risk for developing a disease or condition as disclosed herein, wherein the medicament is coordinated with treatment using a second active agent is contemplated. In yet another related embodiment, the composition is provided wherein the second active agent is another antibody, a growth factor, a cytokine or insulin. Embodiments of any of the aforementioned uses are contemplated wherein the amount of the IL-1β binding antibody or fragment in the medicament is at a dose effective to reduce the dosage of second active agent required to achieve a therapeutic effect.

In yet another aspect of the invention, an article of manufacture is provided, comprising a container, a composition within the container comprising an anti-IL-1β antibody or fragment thereof, and a package insert containing instructions to administer the antibody or fragment to a human in need of treatment according to the aforementioned methods of the invention. In one embodiment, the container further comprises a pharmaceutically suitable carrier, excipient or diluent. In a related embodiment, the composition within the container further comprises a second active agent. In yet another related embodiment, the composition is provided wherein the second active agent is another antibody, a growth factor, a cytokine or insulin.

Kits are also contemplated by the present invention. In one embodiment, a kit comprises a therapeutically or prophylactically effective amount of an anti-IL-1β antibody or fragment, packaged in a container, such as a vial or bottle, and further comprising a label attached to or packaged with the container, the label describing the contents of the container and providing indications and/or instructions regarding use of the contents of the container for treatment or prevention of a disease or condition according to the aforementioned methods of the invention. In one embodiment, the container further comprises a pharmaceutically suitable carrier, excipient or diluent. In a related embodiment, the container further contains a second active agent. In yet another related embodiment, the second active agent comprises another antibody, a growth factor, a cytokine or insulin.

In one embodiment, the article of manufacture, kit or medicament is for the treatment or prevention of a disease or condition in a human, said disease or condition selected from the group consisting of Type 1 diabetes, Type 2 diabetes, hyperglycemia, hyperinsulinemia, obesity, decreased insulin production, and insulin resistance. In one preferred embodiment, the disease or condition is selected from the group consisting of Type 2 diabetes, obesity and insulin resistance. In another embodiment, the instructions of a package insert of an article of manufacture or label of a kit comprise instructions for administration of the antibody or fragment according to any of the aforementioned dose amounts, numbers of subsequent administrations, and dosing intervals between administrations, as well as any combination of dose amounts numbers of subsequent administrations, and dosing intervals between administrations described herein. In yet another embodiment, the container of kit or article of manufacture is a pre-filled syringe.

It is to be understood that where the present specification mentions methods of treatments making use of antibodies or fragments thereof with certain properties (such as Kd values or $IC_{50}$ values), this also means to embody the use of such antibodies or fragments thereof in the manufacture of a medicament for use in these methods. Further, the invention also encompasses antibodies or fragments thereof having these properties as well as pharmaceutical compositions comprising these antibodies or fragments thereof for use in the methods of treatment discussed hereinafter.

BRIEF DESCRIPTION OF THE DRAWINGS

FIG. 6 is a table showing reduction of *Staphyloccus epidermidis*-induced cytokine production in human whole blood by treatment with an anti-IL-1β antibody.

DETAILED DESCRIPTION

Figure 1:
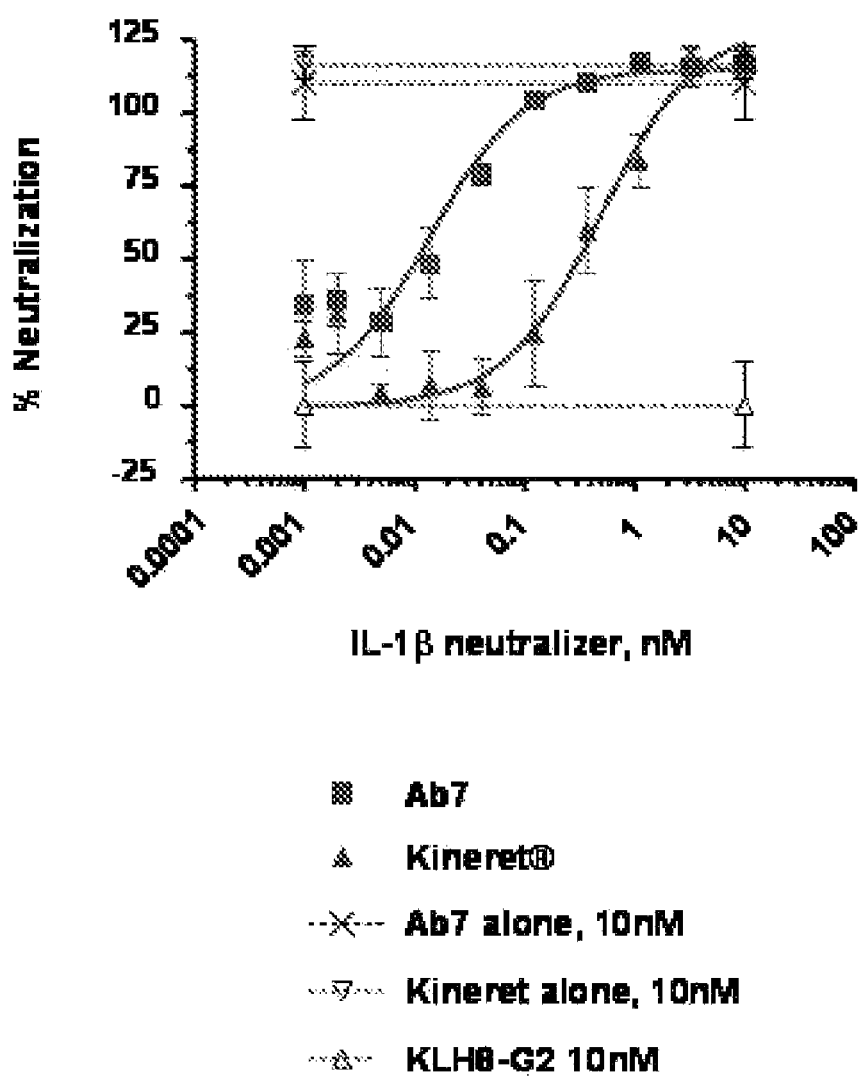
FIG. 1 is a graph showing the results of an in vitro IL-1β inhibition experiment for the antibody designated AB7 and for Kineret® involving IL-1 induced production of IL-8.

IL-1β is a pro-inflammatory cytokine secreted by a number of different cell types including monocytes and macrophages. When released as part of an inflammatory reaction, IL-1β produces a range of biological effects, mainly mediated through induction of other inflammatory mediators such as corticotrophin, platelet factor-4, prostaglandin E2 (PGE2), IL-6, and IL-8. IL-1β induces both local and systemic inflammatory effects through the activation of the IL-1 receptor found on almost all cell types.

The interleukin-1 (IL-1) family of cytokines has been implicated in several disease states such as rheumatoid arthritis (RA), osteoarthritis, Crohn's disease, ulcerative colitis (UC), septic shock, chronic obstructive pulmonary disease (COPD), asthma, graft versus host disease, atherosclerosis, adult T-cell leukemia, multiple myeloma, multiple sclerosis, stroke, and Alzheimer's disease. IL-1 family members include IL-1α, IL-1β, and IL-1Ra. Although related by their ability to bind to IL-1 receptors (IL-1R1, IL-1R2), each of these cytokines is expressed by a different gene and has a different primary amino acid sequence. Furthermore, the physiological activities of these cytokines can be distinguished from each other.

Compounds that disrupt IL-1 receptor signaling have been investigated as therapeutic agents to treat IL-1 mediated diseases, such as for example some of the aforementioned diseases. These compounds include recombinant IL-1Ra (Amgen Inc., Thousand Oaks, Calif.). IL-1 receptor "trap" peptide (Regeneron Inc., Tarrytown, N.Y.), as well as animal-derived IL-1β antibodies and recombinant IL-1 antibodies and fragments thereof.

As noted above, IL-1 receptor antagonist (IL-1Ra) polypeptide has been suggested for use in the treatment of Type 2 diabetes (WO 2004/002512), but there remains a need for effective means to treat Type 2 diabetes, particularly those that do not require daily, repeated injections. An additional challenge for IL-1 receptor antagonist-based therapeutics is the need for such therapeutics to occupy a large number of receptors, which is a formidable task since these receptors are widely expressed on all cells except red blood cells (Dinarello, Curr. Opin. Pharmacol. 4:378-385, 2004). In most immune-mediated diseases, such as the diseases disclosed herein, the amount of IL-1β cytokine that is measurable in body fluids or associated with activated cells is relatively low. Thus, a method of treatment and/or prevention that directly targets the IL-1β ligand is a superior strategy, particularly when administering an IL-1β antibody with high affinity.

The present invention provides methods and related articles of manufacture for the treatment and/or prevention in mammals of Type 2 diabetes, Type 1 diabetes, obesity, hyperglycemia, hyperinsulinemia, decreased insulin production, insulin resistance and/or disease states and conditions characterized by insulin resistance, using an antibody or fragment thereof specific for IL-1β.

As shown in Example 1 below, we have surprisingly found that such an antibody (e.g. with high affinity) can be far more potent an inhibitor of the IL-1 pathway than is IL-Ra (e.g., Kineret®), and as shown in Example 9 below provides an opportunity to achieve a therapeutic effect at a lower dose and/or with less frequent administration than necessary for other drugs, such as recombinant IL-1Ra.

Such methods as described herein with an IL-1β antibody or fragment may include the treatment of a subject suffering from Type 2 diabetes, Type 1 diabetes, obesity, hyperglycemia, hyperinsulinemia, decreased insulin production, hypoinsulinemia, insulin resistance and/or disease states and conditions characterized by insulin resistance. The methods also may include preventing the occurrence of Type 2 diabetes, Type 1 diabetes, obesity, hyperglycemia, hyperinsulinemia, decreased insulin production, insulin resistance and disease states and conditions characterized by insulin resistance or to prevent occurrence of the same in an at risk subject. As used herein, hyperinsulinemia refers to relative hyperinsulinemia due to insulin resistance.

Antibodies, Humanized Antibodies, and Human Engineered Antibodies

The IL-1 (e.g., IL-1β) binding antibodies of the present invention may be provided as polyclonal antibodies, monoclonal antibodies (mAbs), recombinant antibodies, chimeric antibodies, CDR-grafted antibodies, fully human antibodies, single chain antibodies, and/or bispecific antibodies, as well as fragments, including variants and derivatives thereof, provided by known techniques, including, but not limited to enzymatic cleavage, peptide synthesis or recombinant techniques.

Antibodies generally comprise two heavy chain polypeptides and two light chain polypeptides, though single domain antibodies having one heavy chain and one light chain, and heavy chain antibodies devoid of light chains are also contemplated. There are five types of heavy chains, called alpha, delta, epsilon, gamma and mu, based on the amino acid sequence of the heavy chain constant domain. These different types of heavy chains give rise to five classes of antibodies, IgA (including $IgA_1$ and $IgA_2$), IgD, IgE, IgG and IgM, respectively, including four subclasses of IgG, namely $IgG_1$, $IgG_2$, $IgG_3$ and $IgG_4$. There are also two types of light chains, called kappa (κ) or lambda (λ) based on the amino acid sequence of the constant domains. A full-length antibody includes a constant domain and a variable domain. The constant region need not be present in an antigen binding fragment of an antibody. Antigen binding fragments of an antibody disclosed herein can include Fab, Fab', $F(ab')_2$, and F(v) antibody fragments. As discussed in more detail below, IL-1β binding fragments encompass antibody fragments and antigen-binding polypeptides that will bind IL-1β.

Each of the heavy chain and light chain sequences of an antibody, or antigen binding fragment thereof, includes a variable region with three complementarity determining regions (CDRs) as well as non-CDR framework regions (FRs). The terms "heavy chain" and "light chain," as used herein, mean the heavy chain variable region and the light chain variable region, respectively, unless otherwise noted. Heavy chain CDRs are referred to herein as CDR-H1, CDR-H2, and CDR-H3. Light chain CDRs are referred to herein as CDR-L1, CDR-L2, and CDR-L3. Variable regions and CDRs in an antibody sequence can be identified (i) according to general rules that have been developed in the art or (ii) by aligning the sequences against a database of known variable regions. Methods for identifying these regions are described in Kontermann and Dubel, eds., *Antibody Engineering*, Springer, New York, N.Y., 2001, and Dinarello et al., *Current Protocols in Immunology*, John Wiley and Sons Inc., Hoboken, N.J., 2000. Databases of antibody sequences are described in and can be accessed through "The Kabatman" database at www.bioinf.org.uk/abs (maintained by A. C. Martin in the Department of Biochemistry & Molecular Biology University College London, London, England) and VBASE2 at www.vbase2.org, as described in Retter et al., *Nucl. Acids Res.*, 33(Database issue): D671-D674 (2005). The "Kabatman" database web site also includes general rules of thumb for identifying CDRs. The term "CDR," as used herein, is as defined in Kabat et al., *Sequences of Immunological Interest*, 5th ed., U.S. Department of Health and Human Services, 1991, unless otherwise indicated.

Polyclonal antibodies are preferably raised in animals by multiple subcutaneous (sc) or intraperitoneal (ip) injections of the relevant antigen and an adjuvant. An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to {fraction (1/10)} the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibody refers to an antibody obtained from a population of substantially homogeneous antibodies. Monoclonal antibodies are generally highly specific, and may be directed against a single antigenic site, in contrast to conventional (polyclonal) antibody preparations that typically include different antibodies directed against different determinants (epitopes). In addition to their specificity, the monoclonal antibodies are advantageous in that they are synthesized by the homogeneous culture, uncontaminated by other immunoglobulins with different specificities and characteristics.

Monoclonal antibodies to be used in accordance with the present invention may be made by the hybridoma method first described by Kohler et al., (Nature, 256:495-7, 1975), or may be made by recombinant DNA methods (see, e.g., U.S. Pat. No. 4,816,567). The monoclonal antibodies may also be isolated from phage antibody libraries using the techniques described in, for example, Clackson et al., (Nature 352:624-628, 1991) and Marks et al., (J. Mol. Biol. 222:581-597, 1991).

In the hybridoma method, a mouse or other appropriate host animal, such as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or UPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, DMEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

It is further contemplated that antibodies of the invention may be used as smaller antigen binding fragments of the antibody well-known in the art and described herein.

The present invention encompasses IL-1 (e.g., IL-1β) binding antibodies that include two full length heavy chains and two full length light chains. Alternatively, the IL-1β binding antibodies can be constructs such as single chain antibodies or "mini" antibodies that retain binding activity to IL-1β. Such constructs can be prepared by methods known in the art such as, for example, the PCR mediated cloning and assembly of single chain antibodies for expression in E. coli (as described in Antibody Engineering, The practical approach series, J. McCafferty, H. R. Hoogenboom, and D. J. Chiswell, editors, Oxford University Press, 1996). In this type of construct, the variable portions of the heavy and light chains of an antibody molecule are PCR amplified from cDNA. The resulting amplicons are then assembled, for example, in a second PCR step, through a linker DNA that encodes a flexible protein linker composed of the amino acids Gly and Ser. This linker allows the variable heavy and light chain portions to fold in such a way that the antigen binding pocket is regenerated and antigen is bound with affinities often comparable to the parent full-length dimeric immunoglobulin molecule.

The IL-1 (e.g., IL-1β) binding antibodies and fragments of the present invention encompass variants of the exemplary antibodies, fragments and sequences disclosed herein. Variants include peptides and polypeptides comprising one or more amino acid sequence substitutions, deletions, and/or additions that have the same or substantially the same affinity and specificity of epitope binding as one or more of the exemplary antibodies, fragments and sequences disclosed herein. Thus, variants include peptides and polypeptides comprising one or more amino acid sequence substitutions, deletions, and/or additions to the exemplary antibodies, fragments and sequences disclosed herein where such substitutions, deletions and/or additions do not cause substantial changes in affinity and specificity of epitope binding. For example, a variant of an antibody or fragment may result from one or more changes to an antibody or fragment, where the changed antibody or fragment has the same or substantially the same affinity and specificity of epitope binding as the starting sequence. Variants may be naturally occurring, such as allelic or splice variants, or may be artificially constructed. Variants may be prepared from the corresponding nucleic acid molecules encoding said variants. Variants of the present antibodies and IL-1β binding fragments may have changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen.

Variants of IL-1 (e.g., IL-1β) binding antibodies and binding fragments may also be prepared by mutagenesis techniques. For example, amino acid changes may be introduced at random throughout an antibody coding region and the resulting variants may be screened for binding affinity for IL-1β or for another property. Alternatively, amino acid changes may be introduced in selected regions of an IL-1β antibody, such as in the light and/or heavy chain CDRs, and/or in the framework regions, and the resulting antibodies may be screened for binding to IL-1β or some other activity. Amino acid changes encompass one or more amino acid substitutions in a CDR, ranging from a single amino acid difference to the introduction of multiple permutations of amino acids within a given CDR, such as CDR3. In another method, the contribution of each residue within a CDR to IL-1β binding may be assessed by substituting at least one residue within the CDR with alanine. Lewis et al. (1995), Mol. Immunol. 32: 1065-72. Residues which are not optimal for binding to IL-1β may then be changed in order to determine a more optimum sequence. Also encompassed are variants generated by insertion of amino acids to increase the size of a CDR, such as CDR3. For example, most light chain CDR3 sequences are nine amino acids in length. Light chain sequences in an antibody which are shorter than nine residues may be optimized for binding to IL-1β by insertion of appropriate amino acids to increase the length of the CDR.

Variants may also be prepared by "chain shuffling" of light or heavy chains. Marks et al. (1992), Biotechnology 10: 779-83. A single light (or heavy) chain can be combined with a library having a repertoire of heavy (or light) chains and the resulting population is screened for a desired activity, such as binding to IL-1β. This permits screening of a greater sample of different heavy (or light) chains in combination with a single light (or heavy) chain than is possible with libraries comprising repertoires of both heavy and light chains.

The IL-1 (e.g. IL-1β) binding antibodies and fragments of the present invention encompass derivatives of the exemplary antibodies, fragments and sequences disclosed herein. Derivatives include polypeptides or peptides, or variants, fragments or derivatives thereof, which have been chemically modified. Examples include covalent attachment of one or more polymers, such as water soluble polymers, N-linked, or O-linked carbohydrates, sugars, phosphates, and/or other such molecules. The derivatives are modified in a manner that is different from naturally occurring or starting peptide or polypeptides, either in the type or location of the molecules attached. Derivatives further include deletion of one or more chemical groups which are naturally present on the peptide or polypeptide.

The IL-1β binding antibodies and fragments of the present invention can be bispecific. Bispecific antibodies or fragments can be of several configurations. For example, bispecific antibodies may resemble single antibodies (or antibody fragments) but have two different antigen binding sites (variable regions). Bispecific antibodies can be produced by chemical techniques (Kranz et al. (1981), Proc. Natl. Acad. Sci. USA, 78: 5807), by "polydoma" techniques (U.S. Pat. No. 4,474,893) or by recombinant DNA techniques. Bispecific antibodies of the present invention can have binding specificities for at least two different epitopes, at least one of which is an epitope of IL-1β. The IL-1β binding antibodies and fragments can also be heteroantibodies. Heteroantibodies are two or more antibodies, or antibody binding fragments (Fab) linked together, each antibody or fragment having a different specificity.

Techniques for creating recombinant DNA versions of the antigen-binding regions of antibody molecules which bypass the generation of monoclonal antibodies are contemplated for the present IL-1 (e.g., IL-1β) binding antibodies and fragments. DNA is cloned into a bacterial expression system. One example of such a technique suitable for the practice of this invention uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind IL-1β. Such IL-1β binding agents (Fab fragments with specificity for an IL-1β polypeptide) are specifically encompassed within the IL-1β binding antibodies and fragments of the present invention.

The present IL-1 (e.g., IL-1β) binding antibodies and fragments can be humanized or human engineered antibodies. As used herein, a humanized antibody, or antigen binding fragment thereof, is a recombinant polypeptide that comprises a portion of an antigen binding site from a non-human antibody and a portion of the framework and/or constant regions of a human antibody. A human engineered antibody or antibody fragment is a non-human (e.g., mouse) antibody that has been engineered by modifying (e.g., deleting, inserting, or substituting) amino acids at specific positions so as to reduce or eliminate any detectable immunogenicity of the modified antibody in a human.

Humanized antibodies include chimeric antibodies and CDR-grafted antibodies. Chimeric antibodies are antibodies that include a non-human antibody variable region linked to a human constant region. Thus, in chimeric antibodies, the variable region is mostly non-human, and the constant region is human. Chimeric antibodies and methods for making them are described in Morrison, et al., *Proc. Natl. Acad. Sci. USA*, 81: 6841-6855 (1984), Boulianne, et al., *Nature,* 312: 643-646 (1984), and PCT Application Publication WO 86/01533. Although, they can be less immunogenic than a mouse monoclonal antibody, administrations of chimeric antibodies have been associated with human anti-mouse antibody responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. Morrison et al. (1984), Proc. Natl. Acad. Sci., 81: 6851; Neuberger et al. (1984), Nature, 312: 604. One example is the replacement of a Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody of the invention can comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in, Jones et al., Nature, 321: 522-525 (1986), Riechmann et al., Nature, 332: 323-327 (1988), and Verhoeyen et al., Science, 239: 1534-1536 (1988)). Methods that can be used to produce humanized antibodies also are described in U.S. Pat. Nos. 4,816,567, 5,721,367, 5,837,243, and 6,180,377. CDR-grafted antibodies are considered less likely than chimeric antibodies to induce an immune reaction against non-human antibody portions. However, it has been reported that framework sequences from the donor antibodies are required for the binding affinity and/or specificity of the donor antibody, presumably because these framework sequences affect the folding of the antigen-binding portion of the donor antibody. Therefore, when donor, non-human CDR sequences are grafted onto unaltered human framework sequences, the resulting CDR-grafted antibody can exhibit, in some cases, loss of binding avidity relative to the original non-human donor antibody. See, e.g., Riechmann et al., Nature, 332: 323-327 (1988), and Verhoeyen et al., Science, 239: 1534-1536 (1988).

Human engineered antibodies include for example "veneered" antibodies and antibodies prepared using HUMAN ENGINEERING™ technology (U.S. Pat. No. 5,869,619). HUMAN ENGINEERING™ technology is commercially available, and involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or antigen-binding properties. Thus, a low risk position is one for which a substitution is predicted to be beneficial because it is predicted to reduce immunogenicity without significantly affecting antigen binding properties. A moderate risk position is one for which a substitution is predicted to reduce immunogenicity, but is more likely to affect protein folding and/or antigen binding. High risk positions contain residues most likely to be involved in proper folding or antigen binding. Generally, low risk positions in a non-human antibody are substituted with human residues, high risk positions are rarely substituted, and humanizing substitutions at moderate risk positions are sometimes made, although not indiscriminately. Positions with prolines in the non-human antibody variable region sequence are usually classified as at least moderate risk positions.

The particular human amino acid residue to be substituted at a given low or moderate risk position of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering, 7: 805-814 (1994), U.S. Pat. Nos. 5,766,886, 5,770,196, 5,821,123, and 5,869,619, and PCT Application Publication WO 93/11794.

"Veneered" antibodies are non-human or humanized (e.g., chimeric or CDR-grafted antibodies) antibodies that have been engineered to replace certain solvent-exposed amino acid residues so as to further reduce their immunogenicity or enhance their function. As surface residues of a chimeric antibody are presumed to be less likely to affect proper antibody folding and more likely to elicit an immune reaction, veneering of a chimeric antibody can include, for instance, identifying solvent-exposed residues in the non-human framework region of a chimeric antibody and replacing at least one of them with the corresponding surface residues from a human framework region. Veneering can be accomplished by any suitable engineering technique, including the use of the above-described HUMAN ENGINEERING™ technology.

In a different approach, a recovery of binding avidity can be achieved by "de-humanizing" a CDR-grafted antibody. De-humanizing can include restoring residues from the donor antibody's framework regions to the CDR grafted antibody, thereby restoring proper folding. Similar "de-humanization" can be achieved by (i) including portions of the "donor" framework region in the "recipient" antibody or (ii) grafting portions of the "donor" antibody framework region into the recipient antibody (along with the grafted donor CDRs).

For a further discussion of antibodies, humanized antibodies, human engineered, and methods for their preparation, see Kontermann and Dubel, eds., Antibody Engineering, Springer, New York, N.Y., 2001.

Exemplary humanized or human engineered antibodies include IgG, IgM, IgE, IgA, and IgD antibodies. The present antibodies can be of any class (IgG, IgA, IgM, IgE, IgD, etc.) or isotype and can comprise a kappa or lambda light chain. For example, a human antibody can comprise an IgG heavy chain or defined fragment, such as at least one of isotypes, IgG1, IgG2, IgG3 or IgG4. As a further example, the present antibodies or fragments can comprise an IgG1 heavy chain and an IgG1 light chain.

The present antibodies and fragments can be human antibodies, such as antibodies which bind IL-1β polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulin repertoire has been replaced with human V-genes in the mammal chromosome. Such mammals appear to carry out VDJ recombination and somatic hypermutation of the human germline antibody genes in a normal fashion, thus producing high affinity antibodies with completely human sequences.

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851, 1996), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (*Cloning Stem Cells.* 4:91-102, 2002) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TC MOUSE™ with various human antigens produces antibody responses comprising human antibodies.

See also Jakobovits et al., *Proc. Natl. Acad. Sci. USA,* 90:2551 (1993); Jakobovits et al., *Nature,* 362:255-258 (1993); Bruggermann et al., *Year in Immunol.,* 7:33 (1993); and U.S. Pat. No. 5,591,669, U.S. Pat. No. 5,589,369, U.S. Pat. No. 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human antibodies can also be generated through the in vitro screening of antibody display libraries. See Hoogenboom et al. (1991), J. Mol. Biol. 227: 381; and Marks et al. (1991), J. Mol. Biol. 222: 581. Various antibody-containing phage display libraries have been described and may be readily prepared. Libraries may contain a diversity of human antibody sequences, such as human Fab, Fv, and scFv fragments, that may be screened against an appropriate target. Phage display libraries may comprise peptides or proteins other than antibodies which may be screened to identify selective binding agents of IL-1β.

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

The invention contemplates a method for producing target-specific antibody or antigen-binding portion thereof comprising the steps of synthesizing a library of human antibodies on phage, screening the library with target protein or a portion thereof, isolating phage that bind target, and obtaining the antibody from the phage. By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the invention may be obtained in this way.

Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the invention can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum. Antibod. Hybridomas* 3:81-85; Huse et al. (1989) *Science* 246:1275-1281; McCafferty et al., *Nature* (1990) 348:552-554; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) Nuc Acid Res 19:4133-4137; and Barbas et al. (1991) *Proc. Natl. Acad. Sci. USA* 88:7978-7982.

In one embodiment, to isolate human antibodies specific for the target antigen with the desired characteristics, a human $V_H$ and $V_L$ library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (*Nature* 348:552-554, 1990); and Griffiths et al., (*EMBO J* 12:725-734, 1993). The scFv antibody libraries preferably are screened using target protein as the antigen.

Alternatively, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol*, 222:581-597 (1991); U.S. Pat. Nos. 5,565,332 and 5,573,905; Clackson, T., and Wells, J. A., *TIBTECH* 12, 173-184 (1994)). In particular, in vitro selection and evolution of antibodies derived from phage display libraries has become a powerful tool (See Burton, D. R., and Barbas III, C. F., *Adv. Immunol.* 57, 191-280 (1994); Winter, G., et al., *Ann. Rev. Immunol.* 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178: 187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, lke, ZJ/Z, Ff and one of the class II phages Xf, Pf1 and Pf3. The phage may be M13, or fd or a derivative thereof.

Once initial human $V_L$ and $V_H$ segments are selected, "mix and match" experiments, in which different pairs of the initially selected $V_L$ and $V_H$ segments are screened for target binding, are performed to select preferred $V_L/V_H$ pair combinations. Additionally, to further improve the quality of the antibody, the $V_L$ and $V_H$ segments of the preferred $V_L/V_H$ pair(s) can be randomly mutated, preferably within the any of the CDR1, CDR2 or CDR3 region of $V_H$ and/or $V_L$, in a process analogous to the in vivo somatic mutation process responsible for affinity maturation of antibodies during a natural immune response. This in vitro affinity maturation can be accomplished by amplifying $V_L$ and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to target antigen.

Following screening and isolation of an target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (*Bio/Technology*, 10:779-783, 1992).

Methods for display of peptides on the surface of yeast and microbial cells have also been used to identify antigen specific antibodies. See, for example, U.S. Pat. No. 6,699,658.

Antibody libraries may be attached to yeast proteins, such as agglutinin, effectively mimicking the cell surface display of antibodies by B cells in the immune system.

In addition to phage display methods, antibodies may be isolated using ribosome mRNA display methods and microbial cell display methods. Selection of polypeptide using ribosome display is described in Hanes et al., (*Proc. Natl Acad Sci USA*, 94:4937-4942, 1997) and U.S. Pat. Nos. 5,643, 768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

The IL-1 (e.g. IL-1β) binding antibodies and fragments may comprise one or more portions that do not bind IL-1β but instead are responsible for other functions, such as circulating half-life, direct cytotoxic effect, detectable labeling, or activation of the recipient's endogenous complement cascade or endogenous cellular cytotoxicity. The antibodies or fragments may comprise all or a portion of the constant region and may be of any isotype, including IgA (e.g., IgA1 or IgA2), IgD, IgE, IgG (e.g. IgG1, IgG2, IgG3 or IgG4), or IgM. In addition to, or instead of, comprising a constant region, antigen-binding compounds of the invention may include an epitope tag, a salvage receptor epitope, a label moiety for diagnostic or purification purposes, or a cytotoxic moiety such as a radionuclide or toxin.

The constant region (when present) of the present antibodies and fragments may be of the γ1, γ2, γ3, γ4, μ, β2, or δ or ε type, preferably of the γ type, more preferably of the y, type, whereas the constant part of a human light chain may be of the κ or λ type (which includes the $\lambda_1$, $\lambda_2$ and $\lambda_3$ subtypes) but is preferably of the κ type.

Variants also include antibodies or fragments comprising a modified Fc region, wherein the modified Fc region comprises at least one amino acid modification relative to a wild-type Fc region. The variant Fc region may be designed, relative to a comparable molecule comprising the wild-type Fc region, so as to bind Fc receptors with a greater or lesser affinity.

For example, the present IL-1β binding antibodies and fragments may comprise a modified Fc region. Fc region refers to naturally-occurring or synthetic polypeptides homologous to the IgG C-terminal domain that is produced upon papain digestion of IgG. IgG Fc has a molecular weight of approximately 50 kD. In the present antibodies and fragments, an entire Fc region can be used, or only a half-life enhancing portion. In addition, many modifications in amino acid sequence are acceptable, as native activity is not in all cases necessary or desired.

The Fc region can be mutated, if desired, to inhibit its ability to fix complement and bind the Fc receptor with high affinity. For murine IgG Fc, substitution of Ala residues for Glu 318, Lys 320, and Lys 322 renders the protein unable to direct ADCC. Substitution of Glu for Leu 235 inhibits the ability of the protein to bind the Fc receptor with high affinity. Various mutations for human IgG also are known (see, e.g., Morrison et al., 1994, The Immunologist 2: 119 124 and Brekke et al., 1994, The Immunologist 2: 125).

In some embodiments, the present an antibodies or fragments are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g. IgG1, $IgG_2$, $IgG_3$, or $IgG_4$) that is responsible for increasing the in vivo serum half-life of the IgG molecule.

A salvage receptor binding epitope can include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment. See also International applications WO 97/34631 and WO 96/32478 which describe Fc variants and their interaction with the salvage receptor.

Mutation of residues within Fc receptor binding sites can result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position). For example it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., *Mol Immunol.* 30: 105-8, 1993).

Antibody fragments are portions of an intact full length antibody, such as an antigen binding or variable region of the intact antibody. Examples of antibody fragments include Fab, Fab', F(ab')$_2$, and Fv fragments; diabodies; linear antibodies; single-chain antibody molecules (e.g., scFv); multispecific antibody fragments such as bispecific, trispecific, and multi-specific antibodies (e.g., diabodies, triabodies, tetrabodies); minibodies; chelating recombinant antibodies; tribodies or bibodies; intrabodies; nanobodies; small modular immunopharmaceuticals (SMIP), adnectins, binding-domain immunoglobulin fusion proteins; camelized antibodies; $V_{HH}$ containing antibodies; and any other polypeptides formed from antibody fragments.

The present invention includes IL-1β binding antibody fragments comprising any of the foregoing heavy or light chain sequences and which bind IL-1β. The term fragments as used herein refers to any 3 or more contiguous amino acids (e.g., 4 or more, 5 or more 6 or more, 8 or more, or even 10 or more contiguous amino acids) of the antibody and encompasses Fab, Fab', F(ab')$_2$, and F(v) fragments, or the individual light or heavy chain variable regions or portion thereof. IL-13 binding fragments include, for example, Fab, Fab', F(ab')$_2$, Fv and scFv. These fragments lack the Fc fragment of an intact antibody, clear more rapidly from the circulation, and can have less non-specific tissue binding than an intact antibody. See Wahl et al. (1983), J. Nucl. Med., 24: 316-25. These fragments can be produced from intact antibodies using well known methods, for example by proteolytic cleavage with enzymes such as papain (to produce Fab fragments) or pepsin (to produce F(ab')$_2$ fragments).

In vitro and cell based assays are well described in the art for use in determining binding of IL-1β to IL-1 receptor type I (IL-1R1), including assays that determining in the presence of molecules (such as antibodies, antagonists, or other inhibitors) that bind to IL-1β or IL-1RI. (see for example Evans et al., (1995), J. Biol. Chem. 270:11477-11483; Vigers et al., (2000), J. Biol. Chem. 275:36927-36933; Yanofsky et al., (1996), Proc. Natl. Acad. Sci. USA 93:7381-7386; Fredericks et al., (2004), Protein Eng. Des. Sel. 17:95-106; Slack et al., (1993), J. Biol. Chem. 268:2513-2524; Smith et al., (2003), Immunity 18:87-96; Vigers et al., (1997), Nature 386:190-194; Ruggiero et al., (1997), J. Immunol. 158:3881-3887; Guo et al., (1995), J. Biol. Chem. 270:27562-27568; Svenson et al., (1995), Eur. J. Immunol. 25:2842-2850; Arend et al., (1994), J. Immunol. 153:4766-4774). Recombinant IL-1 receptor type I, including human IL-1 receptor type I, for such assays is readily available from a variety of commercial sources (see for example R&D Systems, SIGMA). IL-1 receptor type I also can be expressed from an expression construct or vector introduced into an appropriate host cell using standard molecular biology and transfection techniques known in the art. The expressed IL-1 receptor type I may then be isolated and purified for use in binding assays, or alternatively used directly in a cell associated form.

For example, the binding of IL-1β to IL-1 receptor type I may be determined by immobilizing an IL-1β binding antibody, contacting IL-1β with the immobilized antibody and determining whether the IL-1β was bound to the antibody, and contacting a soluble form of IL-1RI with the bound IL-1β/antibody complex and determining whether the soluble IL-1RI was bound to the complex. The protocol may also include contacting the soluble IL-1RI with the immobilized antibody before the contact with IL-1β, to confirm that the soluble IL-1RI does not bind to the immobilized antibody. This protocol can be performed using a Biacore® instrument for kinetic analysis of binding interactions. Such a protocol can also be employed to determine whether an antibody or other molecule permits or blocks the binding of IL-1β to IL-1 receptor type I.

For other IL-1β/IL-1RI binding assays, the permitting or blocking of IL-1β binding to IL-1 receptor type I may be determined by comparing the binding of IL-1β to IL-1RI in the presence or absence of IL-1β antibodies or IL-1β binding fragments thereof. Blocking is identified in the assay readout as a designated reduction of IL-1β binding to IL-1 receptor type I in the presence of anti-IL-1β antibodies or IL-1β binding fragments thereof, as compared to a control sample that contains the corresponding buffer or diluent but not an IL-1β antibody or IL-1β binding fragment thereof. The assay readout may be qualitatively viewed as indicating the presence or absence of blocking, or may be quantitatively viewed as indicating a percent or fold reduction in binding due to the presence of the antibody or fragment.

Alternatively or additionally, when an IL-1β binding antibody or IL-1β binding fragment substantially blocks IL-1β binding to IL-1RI, the IL-1β binding to IL-1RI is reduced by at least 10-fold, alternatively at least about 20-fold, alternatively at least 50-fold, alternatively at least about 100-fold, alternatively at least about 1000-fold, alternatively at least about 10000-fold, or more, compared to binding of the same concentrations of IL-1β and IL-1RI in the absence of the antibody or fragment. As another example, when an IL-1β binding antibody or IL-1β binding fragment substantially permits IL-1β binding to IL-1RI, the IL-1β binding to IL-1RI is at least about 90%, alternatively at least about 95%, alternatively at least about 99%, alternatively at least about 99.9%, alternatively at least about 99.99%, alternatively at least about 99.999%, alternatively at least about 99.9999%, alternatively substantially identical to binding of the same concentrations of IL-1β and IL-1RI in the absence of the antibody or fragment.

The present invention may in certain embodiments encompass IL-1β binding antibodies or IL-1β binding fragments that bind to the same epitope or substantially the same epitope as one or more of the exemplary antibodies described herein. Alternatively or additionally, the IL-1β binding antibodies or IL-1β binding fragments compete with the binding of an antibody having variable region sequences of AB7, described in U.S. application Ser. No. 11/472,813 (sequences shown below). Alternatively or additionally, the present invention encompasses IL-1β binding antibodies and fragments that bind to an epitope contained in the amino acid sequence ESVDPKNYPKKKMEKRFVFNKIE (SEQ ID NO: 1), an epitope that the antibodies designated AB5 and AB7 (U.S. application Ser. No. 11/472,813) bind to. As contemplated herein, one can readily determine if an IL-1β binding antibody or fragment binds to the same epitope or substantially the same epitope as one or more of the exemplary antibodies, such as for example the antibody designated AB7, using any of several known methods in the art.

For example, the key amino acid residues (epitope) bound by an IL-1β binding antibody or fragment may be determined using a peptide array, such as for example, a PepSpot™ peptide array (JPT Peptide Technologies, Berlin, Germany), wherein a scan of twelve amino-acid peptides, spanning the entire IL-1β amino acid sequence, each peptide overlapping by 11 amino acid to the previous one, is synthesized directly on a membrane. The membrane carrying the peptides is then probed with the antibody for which epitope binding information is sought, for example at a concentration of 2 μg/ml, for 2 hr at room temperature. Binding of antibody to membrane bound peptides may be detected using a secondary IRP-conjugated goat anti-human (or mouse, when appropriate) antibody, followed by enhanced chemiluminescence (ECL). The peptides spot(s) corresponding to particular amino acid residues or sequences of the mature IL-1β protein, and which score positive for antibody binding, are indicative of the epitope bound by the particular antibody.

Alternatively or in addition, antibody competition experiments may be performed and such assays are well known in the art. For example, to determine if an antibody or fragment binds to an epitope contained in a peptide sequence comprising the amino acids ESVDPKNYPKKKMEKRFVFNKIE (SEQ ID NO: 1), which corresponds to residues 83-105 of the mature IL-1β protein, an antibody of unknown specificity may be compared with any of the exemplary of antibodies (e.g., AB7) of the present invention that are known to bind an epitope contained within this sequence. Binding competition assays may be performed, for example, using a Biacore® instrument for kinetic analysis of binding interactions or by ELISA. In such an assay, the antibody of unknown epitope specificity is evaluated for its ability to compete for binding against the known comparator antibody (e.g., AB7). Competition for binding to a particular epitope is determined by a reduction in binding to the IL-1β epitope of at least about 50%, or at least about 70%, or at least about 80%, or at least about 90%, or at least about 95%, or at least about 99% or about 100% for the known comparator antibody (e.g., AB7) and is indicative of binding to substantially the same epitope.

In view of the identification in this disclosure of IL-1β binding regions in exemplary antibodies and/or epitopes recognized by the disclosed antibodies, it is contemplated that additional antibodies with similar binding characteristics and therapeutic or diagnostic utility can be generated that parallel the embodiments of this disclosure.

Antigen-binding fragments of an antibody include fragments that retain the ability to specifically bind to an antigen, generally by retaining the antigen-binding portion of the antibody. It is well established that the antigen-binding function of an antibody can be performed by fragments of a full-length antibody. Examples of antigen-binding portions include (i) a Fab fragment, which is a monovalent fragment consisting of the VL, VH, CL and CH1 domains; (ii) a F(ab')$^2$ fragment, which is a bivalent fragment comprising two Fab fragments linked by a disulfide bridge at the hinge region; (iii) a Fd fragment which is the $V_H$ and CH1 domains; (iv) a Fv fragment which is the $V_L$ and $V_H$ domains of a single arm of an antibody, (v) a dAb fragment (Ward et al., (1989) Nature 341:544-546), which is a VH domain; and (vi) an isolated complementarity determining region (CDR). Single chain antibodies are also encompassed within the term antigen-binding portion of an antibody. The IL-1β binding antibodies and fragments of the present invention also encompass monovalent or multivalent, or monomeric or multimeric (e.g. tetrameric), CDR-derived binding domains with or without a scaffold (for example, protein or carbohydrate scaffolding).

The present IL-1β binding antibodies or fragments may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibodies and fragments comprising immunoadhesion molecules can be obtained using standard recombinant DNA techniques, as described herein. Preferred antigen binding portions are complete domains or pairs of complete domains.

The IL-1β binding antibodies and fragments of the present invention also encompass domain antibody (dAb) fragments (Ward et al., Nature 341:544-546, 1989) which consist of a $V_H$ domain. The IL-1β binding antibodies and fragments of the present invention also encompass diabodies, which are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

The IL-1β binding antibodies and fragments of the present invention also encompass single-chain antibody fragments (scFv) that bind to IL-1β. An scFv comprises an antibody heavy chain variable region ($V_H$) operably linked to an antibody light chain variable region ($V_L$) wherein the heavy chain variable region and the light chain variable region, together or individually, form a binding site that binds IL-1β. An scFv may comprise a $V_H$ region at the amino-terminal end and a $V_L$ region at the carboxy-terminal end. Alternatively, scFv may comprise a $V_L$ region at the amino-terminal end and a $V_H$ region at the carboxy-terminal end. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883).

An scFv may optionally further comprise a polypeptide linker between the heavy chain variable region and the light chain variable region. Such polypeptide linkers generally comprise between 1 and 50 amino acids, alternatively between 3 and 12 amino acids, alternatively 2 amino acids. An example of a linker peptide for linking heavy and light chains in an scFv comprises the 5 amino acid sequence Gly-Gly-Gly-Gly-Ser (SEQ ID NO: 2). Other examples comprise one or more tandem repeats of this sequence (for example, a polypeptide comprising two to four repeats of Gly-Gly-Gly-Gly-Ser (SEQ ID NO: 2) to create linkers.

The IL-1β binding antibodies and fragments of the present invention also encompass heavy chain antibodies (HCAb). Exceptions to the $H_2L_2$ structure of conventional antibodies occur in some isotypes of the immunoglobulins found in camelids (camels, dromedaries and llamas; Hamers-Casterman et al., 1993 Nature 363: 446; Nguyen et al., 1998 J. Mol. Biol. 275: 413), wobbegong sharks (Nuttall et al., Mol Immunol. 38:313-26, 2001), nurse sharks (Greenberg et al., Nature 374:168-73, 1995; Roux et al., 1998 Proc. Nat. Acad. Sci. USA 95: 11804), and in the spotted ratfish (Nguyen, et al., "Heavy-chain antibodies in Camelidae; a case of evolutionary innovation," 2002 Immunogenetics 54(1): 39-47). These antibodies can apparently form antigen-binding regions using only heavy chain variable regions, in that these functional antibodies are dimers of heavy chains only (referred to as "heavy-chain antibodies" or "HCAbs"). Accordingly, some embodiments of the present IL-1β binding antibodies and fragments may be heavy chain antibodies that specifically bind to IL-1β. For example, heavy chain antibodies that are a class of IgG and devoid of light chains are produced by animals of the genus Camelidae which includes camels, dromedaries and llamas (Hamers-Casterman et al., Nature 363:446-448 (1993)). HCAbs have a molecular weight of about 95 kDa instead of the about 160 kDa molecular weight of conventional IgG antibodies. Their binding domains consist only of the heavy-chain variable domains, often referred to as $V_{HH}$ to distinguish them from conventional $V_H$. Muyldermans et al., J. Mol. Recognit. 12:131-140 (1999). The variable domain of the heavy-chain antibodies is sometimes referred to as a nanobody (Cortez-Retamozo et al., Cancer Research 64:2853-57, 2004). A nanobody library may be generated from an immunized dromedary as described in Conrath et al., (Antimicrob Agents Chemother 45: 2807-12, 2001) or using recombinant methods.

Since the first constant domain ($C_{H1}$) is absent (spliced out during mRNA processing due to loss of a splice consensus signal), the variable domain ($V_{HH}$) is immediately followed by the hinge region, the $C_{H2}$ and the $C_{H3}$ domains (Nguyen et al., Mol. Immunol. 36:515-524 (1999); Woolven et al., Immunogenetics 50:98-101 (1999)). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains.

Although the HCAbs are devoid of light chains, they have an antigen-binding repertoire. The genetic generation mechanism of HCAbs is reviewed in Nguyen et al. Adv. Immunol 79:261-296 (2001) and Nguyen et al., Immunogenetics 54:39-47 (2002). Sharks, including the nurse shark, display similar antigen receptor-containing single monomeric V-domains. Irving et al., J. Immunol. Methods 248:31-45 (2001); Roux et al., Proc. Natl. Acad. Sci. USA 95:11804 (1998).

$V_{HH}$s comprise small intact antigen-binding fragments (for example, fragments that are about 15 kDa, 118-136 residues). Camelid $V_{HH}$ domains have been found to bind to antigen with high affinity (Desmyter et al., *J. Biol. Chem.* 276:26285-90, 2001), with $V_{HH}$ affinities typically in the nanomolar range and comparable with those of Fab and scFv fragments. $V_{HH}$s are highly soluble and more stable than the corresponding derivatives of scFv and Fab fragments. $V_H$ fragments have been relatively difficult to produce in soluble form, but improvements in solubility and specific binding can be obtained when framework residues are altered to be more $V_{HH}$-like. (See, for example, Reichman et al., J Immunol Methods 1999, 231:25-38.) $V_{HH}$s carry amino acid substitutions that make them more hydrophilic and prevent prolonged interaction with BiP (immunoglobulin heavy-chain binding protein), which normally binds to the H-chain in the Endoplasmic Reticulum (ER) during folding and assembly, until it is displaced by the L-chain. Because of the $V_{HH}$s' increased hydrophilicity, secretion from the ER is improved.

Functional $V_{HH}$s may be obtained by proteolytic cleavage of HCAb of an immunized camelid, by direct cloning of $V_{HH}$ genes from B-cells of an immunized camelid resulting in recombinant $V_{HH}$s, or from naive or synthetic libraries. $V_{HH}$s with desired antigen specificity may also be obtained through phage display methodology. Using $V_{HH}$s in phage display is much simpler and more efficient compared to Fabs or scFvs, since only one domain needs to be cloned and expressed to obtain a functional antigen-binding fragment. Muyldermans, Biotechnol. 74:277-302 (2001); Ghahroudi et al., FEBS Lett. 414:521-526 (1997); and van der Linden et al., J. Biotechnol. 80:261-270 (2000). Methods for generating antibodies having camelid heavy chains are also described in U.S. Patent Publication Nos. 20050136049 and 20050037421.

Ribosome display methods may be used to identify and isolate scFv and/or $V_{HH}$ molecules having the desired binding activity and affinity. Irving et al., J. Immunol. Methods 248: 31-45 (2001). Ribosome display and selection has the potential to generate and display large libraries ($10^{14}$).

Other embodiments provide $V_{HH}$-like molecules generated through the process of camelisation, by modifying non-Camelidae $V_H$s, such as human $V_H$s, to improve their solubility and prevent non-specific binding. This is achieved by replacing residues on the $V_L$s side of $V_H$s with $V_{HH}$-like residues, thereby mimicking the more soluble $V_{HH}$ fragments. Camelised $V_H$ fragments, particularly those based on the human framework, are expected to exhibit a greatly reduced immune response when administered in vivo to a patient and, accordingly, are expected to have significant advantages for therapeutic applications. Davies et al., FEBS Lett. 339:285-290 (1994); Davies et al., Protein Eng. 9:531-537 (1996); Tanha et al., J. Biol. Chem. 276:24774-24780 (2001); and Riechmann et al., Immunol. Methods 231:25-38 (1999).

A wide variety of expression systems are available for the production of IL-1β fragments including Fab fragments, scFv, and $V_{HH}$s. For example, expression systems of both prokaryotic and eukaryotic origin may be used for the large-scale production of antibody fragments and antibody fusion proteins. Particularly advantageous are expression systems that permit the secretion of large amounts of antibody fragments into the culture medium.

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab. A "minibody" consisting of scFv fused to CH3 via a peptide linker (hingeless) or via an IgG hinge has been described in Olafsen, et al., Protein Eng Des Sel. 2004 April; 17(4):315-23.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al (*EMBO J.* 14:1542-51, 1995) and Wheeler et al. (*FASEB J* 17:1733-5. 2003). Transbodies are cell-permeable antibodies in which a protein transduction domains (PTD) is fused with single chain variable fragment (scFv) antibodies Heng et al., (*Med Hypotheses.* 64:1105-8, 2005).

The IL-1β binding antibodies and fragments of the present invention also encompass antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

The IL-1β binding antibodies and fragments of the present invention also encompass immunoadhesins. One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs disclosed herein permit the immunoadhesin to specifically bind to IL-1β.

The IL-1β binding antibodies and fragments of the present invention also encompass antibody mimics comprising one or more IL-1β binding portions built on an organic or molecular scaffold (such as a protein or carbohydrate scaffold). Proteins having relatively defined three-dimensional structures, commonly referred to as protein scaffolds, may be used as reagents for the design of antibody mimics. These scaffolds typically contain one or more regions which are amenable to specific or random sequence variation, and such sequence randomization is often carried out to produce libraries of proteins from which desired products may be selected. For example, an antibody mimic can comprise a chimeric non-immunoglobulin binding polypeptide having an immunoglobulin-like domain containing scaffold having two or more solvent exposed loops containing a different CDR from a parent antibody inserted into each of the loops and exhibiting selective binding activity toward a ligand bound by the parent antibody. Non-immunoglobulin protein scaffolds have been proposed for obtaining proteins with novel binding properties. (Tramontano et al., J. Mol. Recognit. 7:9, 1994; McConnell and Hoess, J. Mol. Biol. 250:460, 1995). Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164:243, 1995; Wang et al., J. Biol. Chem. 270:12250, 1995). Methods for employing scaffolds for antibody mimics are disclosed in U.S. Pat. No. 5,770,380 and US Patent Publications 2004/0171116, 2004/0266993, and 2005/0038229.

Preferred IL-1β antibodies or antibody fragments for use in accordance with the invention generally bind to human IL-1β with high affinity (e.g., as determined with BIACORE), such as for example with an equilibrium binding dissociation constant ($K_D$) for IL-1β of about 10 nM or less, about 5 nM or less, about 1 nM or less, about 500 pM or less, or more preferably about 250 pM or less, about 100 pM or less, about 50 pM or less, about 25 pM or less, about 10 pM or less, about 5 pM or less, about 3 pM or less about 1 pM or less, about 0.75 pM or less, about 0.5 pM or less, or about 0.3 pM or less.

Antibodies or fragments of the present invention may, for example, bind to IL-1β with an $IC_{50}$ of about 10 nM or less, about 5 nM or less, about 2 nM or less, about 1 nM or less, about 0.75 nM or less, about 0.5 nM or less, about 0.4 nM or less, about 0.3 nM or less, or even about 0.2 nM or less, as determined by enzyme linked immunosorbent assay (ELISA). Preferably, the antibody or antibody fragment of the present invention does not cross-react with any target other than IL-1. For example, the present antibodies and fragments may bind to IL-1β, but do not detectably bind to IL-1α, or have at least about 100 times (e.g., at least about 150 times, at least about 200 times, or even at least about 250 times) greater selectivity in its binding of IL-1β relative to its binding of IL-1α. Antibodies or fragments used according to the invention may, in certain embodiments, inhibit IL-1β induced expression of serum IL-6 in an animal by at least 50% (e.g., at least 60%, at least 70%, or even at least 80%) as compared to the level of serum IL-6 in an IL-1β stimulated animal that has not been administered an antibody or fragment of the invention. Antibodies may bind IL-1β but permit or substantially permit the binding of the bound IL-1β ligand to IL-1 receptor type I (IL-1RI). In contrast to many known IL-1β binding antibodies that block or substantially interfere with binding of IL-1β to IL-1RI, the antibodies designated AB5 and AB7 (U.S. application Ser. No. 11/472,813) selectively bind to the IL-1β ligand, but permit the binding of the bound IL-1β ligand to IL-1RI. For example, the antibody designated AB7 binds to an IL-1β epitope but still permits the bound IL-1β to bind to IL-1RI. In certain embodiments, the antibody may decrease the affinity of interaction of bound IL-1β to bind to IL-1RI. Accordingly, the invention provides, in a related aspect, use of an IL-1β binding antibody or IL-1β binding antibody fragment that has at least one of the aforementioned characteristics. Any of the foregoing antibodies, antibody fragments, or polypeptides of the invention can be humanized or human engineered, as described herein.

A variety of IL-1 (e.g., IL-1β) antibodies and fragments known in the art may be used according the methods provided herein, including for example antibodies described in or derived using methods described in the following patents and patent applications: U.S. Pat. No. 4,935,343; US 2003/0026806; US 2003/0124617; WO 2006/081139; WO 03/034984; WO 95/01997; WO 02/16436; WO 03/010282; WO 03/073982, WO 2004/072116, WO 2004/067568, EP 0 267 611 B1, EP 0 364 778 B1, and U.S. application Ser. No. 11/472,813. As a non-limiting example, antibodies AB5 and AB7 (U.S. application Ser. No. 11/472,813, WO2007/002261) may be used in accordance with the invention. Variable region sequences of AB5 and AB7 are as follows:

AB5

Light Chain (SEQ ID NO: 3)
DIQMTQTTSSLSASLGDRVTIS<u>CRASQDISNYLS</u>WYQQKPDGTVKLLIY<u>Y</u>

<u>TSKLHS</u>GVPSRFSGSGSGTDYSLTISNLEQEDIATYFC<u>LQGKMLPWTFGG</u>

<u>GTKLEIK</u>

The underlined sequences depict (from left to right) CDR1, 2 and 3.

Heavy Chain (SEQ ID NO: 4)
QVTLKESGPGILKPSQTLSLTCSFSGFSLS<u>TSGMGVG</u>WIRQPSGKGLEWL <u>AHIWWDGDESYNPSLK</u>TQLTISKDTSRNQVFLKITSVDTVDTATYFCAR<u>N</u>

<u>RYDPPWFVDW</u>GQGTLVTVSS

The underlined sequences depict (from left to right) CDR1, 2 and 3.

AB7

Light Chain (SEQ ID NO: 5)
DIQMTQSTSSLSASVGDRVTITC<u>RASQDISNYLS</u>WYQQKPGKAVKLLIY<u>Y</u>

<u>TSKLHS</u>GVPSRFSGSGSGTDYTLTISSLQQEDFATYFC<u>LQGKMLPWTFGQ</u>

<u>GTKLEIK</u>

The underlined sequences depict (from left to right) CDR1, 2 and 3.

Heavy Chain (SEQ ID NO: 6)
QVQLQESGPGLVKPSQTLSLTCSFSGFSLS<u>TSGMGVG</u>WIRQPSGKGLEWL <u>AHIWWDGDESYNPSLK</u>SRLTISKDTSKNQVSLKITSVTAADTAVYFCAR<u>N</u>

<u>RYDPPWFVDW</u>GQGTLVTVSS

The underlined sequences depict (from left to right) CDR1, 2 and 3.

The antibodies and antibody fragments described herein can be prepared by any suitable method. Suitable methods for preparing such antibodies and antibody fragments are known in the art. Other methods for preparing the antibodies and antibody fragments are as described herein as part of the invention. The antibody, antibody fragment, or polypeptide of the invention, as described herein, can be isolated or purified to any degree. As used herein, an isolated compound is a compound that has been removed from its natural environment. A purified compound is a compound that has been increased in purity, such that the compound exists in a form that is more pure than it exists (i) in its natural environment or (ii) when initially synthesized and/or amplified under laboratory conditions, wherein "purity" is a relative term and does not necessarily mean "absolute purity."

Pharmaceutical Compositions

IL-1 (e.g., IL-1β) binding antibodies and antibody fragments for use according to the present invention can be formulated in compositions, especially pharmaceutical compositions, for use in the methods herein. Such compositions comprise a therapeutically or prophylactically effective amount of an IL-1β binding antibody or antibody fragment of the invention in admixture with a suitable carrier, e.g., a pharmaceutically acceptable agent. Typically, IL-1β binding antibodies and antibody fragments of the invention are sufficiently purified for administration to an animal before formulation in a pharmaceutical composition.

Pharmaceutically acceptable agents include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in *Remington's Pharmaceutical Sciences,* 18th Edition, A. R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g. sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g. polysorbate 20, polysorbate 80); poloxamers (e.g. poloxamer 188); poly (ethylene glycol) phenyl ethers (e.g. Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g. Pluronics, PF68 etc). Exemplary amounts of surfactant that may be present in the pre-lyophilized formulation are from about 0.001-0.5%. High molecular weight structural additives (e.g. fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, intralesional, intrarectal, transdermal, oral, and inhaled routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) sustained release and/or increased stability or half-life in a particular local environment. The invention contemplates that in certain embodiments such compositions may include a significantly larger amount of antibody or fragment in the initial deposit, while the effective amount of antibody or fragment actually released and available at any point in time for is in accordance with the disclosure herein an amount much lower than the initial deposit. The compositions can include the formulation of IL-1β binding antibodies, antibody fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies). See, for example, the description of controlled release porous polymeric microparticles for the delivery of pharmaceutical compositions in PCT Application Publication WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly (2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon- (rhIFN—), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present invention. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humour of the eye. Esterified derivatives of hyaluronic acid have been used to produce microspheres for use in delivery that are biocompatible and biodegrable (see for example, Cortivo et al., Biomaterials (1991) 12:727-730; European Publication No. 517,565; International Publication No. WO 96/29998; Illum et al., J. Controlled Rel. (1994) 29:133-141). Exemplary hyaluronic acid containing compositions of the present invention comprise a hyaluronic acid ester polymer in an amount of approximately 0.1% to about 40% (w/w) of an IL-1β binding antibody or fragment to hyaluronic acid polymer.

Both biodegradable and non-biodegradable polymeric matrices can be used to deliver compositions in accordance with the invention, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which can be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see for example WO 04/009664, WO 05/087201, Sawhney, et al., Macromolecules, 1993, 26, 581-587,) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324).

A pharmaceutical composition comprising an IL-1β binding antibody or fragment can be formulated for inhalation, such as for example, as a dry powder. Inhalation solutions also can be formulated in a liquefied propellant for aerosol delivery. In yet another formulation, solutions may be nebulized. Additional pharmaceutical composition for pulmonary administration include, those described, for example, in PCT Application Publication WO 94/20069, which discloses pulmonary delivery of chemically modified proteins. For pulmonary delivery, the particle size should be suitable for delivery to the distal lung. For example, the particle size can be from 1 μm to 5 μm; however, larger particles may be used, for example, if each particle is fairly porous.

Certain formulations containing IL-1β binding antibodies or antibody fragments can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Another preparation can involve an effective quantity of an IL-1β binding antibody or fragment in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations can be determined in view of the present disclosure and general knowledge of formulation technology, depending upon the intended route of administration, delivery format, and desired dosage. Regardless of the manner of administration, an effective dose can be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages can be ascertained through use of appropriate dose-response data.

Additional formulations will be evident in light of the present disclosure, including formulations involving IL-1β binding antibodies and fragments in combination with one or more other therapeutic agents. For example, in some formulations, an IL-1β binding antibody, antibody fragment, nucleic acid, or vector of the invention is formulated with a second inhibitor of an IL-1 signaling pathway Representative second inhibitors include, but are not limited to, antibodies, antibody fragments, peptides, polypeptides, compounds, nucleic acids, vectors and pharmaceutical compositions, such as, for example, those described in U.S. Pat. No. 6,899,878, US 2003022869, US 20060094663, US 20050186615, US 20030166069, WO/04022718, WO/05084696, WO/05019259. For example, a composition may comprise an IL-1β binding antibody, antibody fragment, nucleic acid, or vector of the invention in combination with an IL-1β binding antibody, fragment, or a nucleic acid or vector encoding such an antibody or fragment.

The pharmaceutical compositions can comprise IL-1β binding antibodies or fragments in combination with other active agents. Such combinations are those useful for their intended purpose. The combinations which are part of this invention can be IL-1β antibodies and fragments, such as for example those described herein, and at least one additional agent selected from the lists below. The active agents set forth below are illustrative for purposes and not intended to be limited. The combination can also include more than one additional agent, e.g., two or three additional agents if the combination is such that the formed composition can perform its intended function.

The invention further contemplates that pharmaceutical compositions comprising one or more other active agents may be administered separately from the IL-1β binding antibodies or fragments, and such separate administrations may be performed at the same point or different points in time, such as for example the same or different days. Administration of the other active agents may be according to standard medical practices known in the art, or the administration may be modified (e.g., longer intervals, smaller dosages, delayed initiation) when used in conjunction with administration of IL-1β binding antibodies or fragments, such as disclosed herein.

Active agents or combinations with the present antibodies or fragments include a non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors. Other active agents for combination include steroids such as prednisolone, prednisone, methylprednisolone, betamethasone, dexamethasone, or hydrocortisone. Such a combination may be especially advantageous, since one or more side-effects of the steroid can be reduced or even eliminated by tapering the steroid dose required when treating patients in combination with the present antibodies and fragments.

Alternatively or in addition, therapeutic treatment with at least one or more additional active agents may be used which may act via different modes of action: 1) sulfonylureas (e.g., chlorpropamide, tolazamide, acetohexamide, tolbutamide, glyburide, glimepiride, glipizide) and/or meglitinides (e.g., repaglinide, nateglinide) that essentially stimulate insulin secretion; 2) biguanides (e.g., metformin) act by promoting glucose utilization, reducing hepatic glucose production and diminishing intestinal glucose output; 3) alpha-glucosidase inhibitors (e.g. acarbose, miglitol) slow down carbohydrate digestion and consequently absorption from the gut and reduce postprandial hyperglycemia; 4) thiazolidinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054) that enhance insulin action, thus promoting glucose utilization in peripheral tissues; 5) glucagon-like-peptides including DPP4 inhibitors (e.g., sitagliptin); and 6) insulin, which stimulates tissue glucose utilization and inhibits hepatic glucose output. Glucagon-like peptide-1 (GLP-1), DPP-IV-resistant analogues (incretin mimetics), DPP-IV inhibitors, insulin, insulin analogues, PPAR gamma agonists, dual-acting PPAR agonists, GLP-1 agonists or analogues, PTP1B inhibitors, SGLT inhibitors, insulin secretagogues, RXR agonists, glycogen synthase kinase-3 inhibitors, insulin sensitizers, immune modulators, beta-3 adrenergic receptor agonists, Pan-PPAR agonists, 11beta-HSD1 inhibitors, amylin analogues, biguanides, alpha-glucosidase inhibitors, meglitinides, thiazolidinediones, sulfonylureas and the like also may be used as the other active agent(s) (see for example Nathan, 2006, N. Engl. J. Med. 355:2477-2480; Kahn et al., 2006, N. Engl. J. Med. 355:2427-2443). In yet another embodiment, the active agent may be an HMG Co-A reductase inhibitor (e.g., statins).

It is further contemplated that an anti-IL-1β antibody or fragment administered to a subject in accordance with the invention may be administered in combination with treatment with at least one additional active agent, such as for example any of the aforementioned active agents. In one embodiment, treatment with the at least one active agent is maintained. In another embodiment, treatment with the at least one active agent is reduced or discontinued (e.g., when the subject is stable), while treatment with the anti-IL-1β antibody or fragment is maintained at a constant dosing regimen. In another embodiment, treatment with the at least one active agent is reduced or discontinued (e.g., when the subject is stable), and treatment with the anti-IL-1β antibody or fragment is reduced (e.g., lower dose, less frequent dosing, shorter treatment regimen). In another embodiment, treatment with the at least one active agent is reduced or discontinued (e.g., when the subject is stable), and treatment with the anti-IL-1β antibody or fragment is increased (e.g., higher dose, more frequent dosing, longer treatment regimen). In yet another embodiment, treatment with the at least one active agent is maintained and treatment with the anti-IL-1β antibody or fragment is reduced or discontinued (e.g., lower dose, less frequent dosing, shorter treatment regimen). In yet another embodiment, treatment with the at least one active agent and treatment with the anti-IL-1β antibody or fragment are reduced or discontinued (e.g., lower dose, less frequent dosing, shorter treatment regimen)

The pharmaceutical compositions used in the invention may include a therapeutically effective amount or a prophylactically effective amount of the IL-1β binding antibodies or fragments. A therapeutically effective amount refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A prophylactically effective amount refers to an amount effective, at dosages and for periods of time necessary, to achieve the desired prophylactic result.

A therapeutically or prophylactically effective amount of a pharmaceutical composition comprising an IL-1β binding antibody or fragment will depend, for example, upon the therapeutic objectives such as the indication for which the composition is being used, the route of administration, and the condition of the subject. Pharmaceutical compositions are administered in a therapeutically or prophylactically effective amount to treat an IL-1 related condition. A "therapeutically or prophylactically effective amount" of an IL-1β binding antibody or fragment, of the invention is that amount which can treat or prevent one or more symptoms of an IL-1 related disease in a subject, as disclosed herein.

Methods of Use

Anti-IL-1β antibodies in an effective amount may be used in the present invention for the treatment and/or prevention of Type 1 diabetes, Type 2 diabetes, obesity, hyperglycemia, hyperinsulinemia, insulin resistance and disease states and conditions characterized by insulin resistance. Such methods may be used to treat a mammalian subject (e.g., human) suffering from Type 2 diabetes, Type 1 diabetes, obesity, hyperglycemia, hyperinsulinemia, insulin resistance and disease states and conditions characterized by insulin resistance or to prevent occurrence of the same in an at risk subject.

The terms "prevention", "prevent", "preventing", "suppression", "suppress", "suppressing", "inhibit" and "inhibition" as used herein refer to a course of action (such as administering a compound or pharmaceutical composition) initiated in a manner (e.g., prior to the onset of a clinical symptom of a disease state or condition) so as to prevent, suppress or reduce, either temporarily or permanently, the onset of a clinical manifestation of the disease state or condition. Such preventing, suppressing or reducing need not be absolute to be useful.

The terms "treatment", "treat" and "treating" as used herein refers a course of action (such as administering a compound or pharmaceutical composition) initiated after the onset of a clinical symptom of a disease state or condition so as to eliminate, reduce, suppress or ameliorate, either temporarily or permanently, a clinical manifestation or progression of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or compound of the disclosure.

The term "therapeutically effective amount" as used herein refers to an amount of a compound (e.g., antibody), either alone or as a part of a pharmaceutical composition, that is capable of having any detectable, positive effect on any symptom, aspect, or characteristics of a disease state or condition when administered to a patient (e.g., as one or more doses). Such effect need not be absolute to be beneficial.

The term "insulin resistance" as used herein refers to a condition where a normal amount of insulin is unable to produce a normal physiological or molecular response. In some cases, a hyper-physiological amount of insulin, either endogenously produced or exogenously added, is able to overcome the insulin resistance in whole or in part and produce a biologic response.

Anti-IL-1β antibodies or fragments may be administered to a human in an effective amount for the treatment and/or prevention of Type 2 diabetes, Type 1 diabetes, obesity, hyperglycemia, hyperinsulinemia, insulin resistance and/or disease states and conditions characterized by insulin resistance. Other diseases or conditions contemplated for treatment with anti-IL-1β antibodies or fragments according to the present invention include pre-diabetes, dyslipidemia, hyperlipidemia, hypertension, Metabolic Syndrome and Sickness Behavior. The invention further contemplates methods of using such antibodies or fragments to decrease the incidence or severity, or stabilize, complications or conditions associated with Type 2 diabetes, such as for example, retinopathy, renal failure, cardiovascular disease (e.g., atherosclerosis, peripheral vascular disease), and wound healing (e.g., diabetic ulcer).

In addition, the invention further contemplates the use of IL-1β antibodies and fragments as described herein to reduce the level of C-reactive protein (CRP) in a subject. CRP is an acute phase protein that is produced predominantly by hepatocytes under the influence of cytokines such as IL-1, IL-6, and tumor necrosis factor (TNF). Based on the 2007 electronic version of the internal medicine textbook UpToDate®, despite a lack of specificity for the cause of inflammation (e.g. infection, chronic renal disease, auto-inflammatory disease, cancer), data from more than 30 epidemiologic studies have shown a significant association between elevated serum or plasma concentrations of CRP and the prevalence of underlying atherosclerosis, the risk of recurrent cardiovascular events among patients with established disease, and the incidence of first cardiovascular events among individuals at risk for atherosclerosis. In addition, the interplay of primary renal disease, the resultant kidney failure with its oxidative stress and post-synthetic protein modifications, dialysis with the associated contaminants and effect of the dialysis membrane on serum proteins, and the infections associated with repeated access site entry and subsequent systemic infections leads these patients to an excessive load of inflammatory stimuli. As the serum creatinine clearance levels fall with the worsening renal function there is a proportional rise in of serum inflammatory mediators (e.g., cytokines TNF, IL-6, IL-1) as well as evidence of the body attempting to combat this situation with increased, but inefficient, production of IL-1 RA and IL-10, anti-inflammatory mediators. This inflammatory state in chronic renal failure patients leads to atherosclerotic plaque instability due to direct triggering of apoptosis of vascular smooth muscle cells. The consequence of cytokine elevation leads to one of the top two major mortalities in these patients—a remarkable increase in cardiovascular deaths from myocardial infarctions and strokes. A direct illustration of this increased risk is seen with evaluation of patient's CRP levels; when divided into quartiles of CRP values, the group with the highest CRP values has a 12-month mortality rate of approximately 35%. Thus, the present invention discloses the use of an IL-1β antibody or fragment as provided herein to reduce CRP levels in such patients (e.g., subjects suffering from renal disease). The reduction in CRP levels in a subject as described herein is a suitable means to achieve a corresponding proportional decrease in cardiovascular morbidity and mortality.

In one embodiment, the anti-IL-1β antibody or fragment is administered to a subject with at least one of the aforementioned diseases, conditions, or complications and the subject also receives at least one other medically accepted treatment (e.g, medication, drug, therapeutic, active agent) for the disease, condition or complication. In another embodiment, the at least one other medically accepted treatment for the disease, condition or complication is reduced or discontinued (e.g., when the subject is stable), while treatment with the anti-IL-1β antibody or fragment is maintained at a constant dosing regimen. In another embodiment, the at least one other medically accepted treatment for the disease, condition or complication is reduced or discontinued (e.g., when the subject is stable), and treatment with the anti-IL-1β antibody or fragment is reduced (e.g., lower dose, less frequent dosing, shorter treatment regimen). In another embodiment, the at least one other medically accepted treatment for the disease, condition or complication is reduced or discontinued (e.g., when the subject is stable), and treatment with the anti-IL-1β antibody or fragment is increased (e.g., higher dose, more frequent dosing, longer treatment regimen). In yet another embodiment, the at least one other medically accepted treatment for the disease, condition or complication is maintained and treatment with the anti-IL-1β antibody or fragment is reduced or discontinued (e.g., lower dose, less frequent dosing, shorter treatment regimen). In yet another embodiment, the at least one other medically accepted treatment for the disease, condition or complication and treatment with the anti-IL-1β antibody or fragment are reduced or discontinued (e.g., lower dose, less frequent dosing, shorter treatment regimen)

In preferred methods of treating or preventing the aforementioned diseases or conditions (e.g., Type 1 diabetes, Type 2 diabetes, hyperglycemia, hyperinsulinemia, obesity, insulin resistance) anti-IL-1β antibody or fragment thereof is administered to the human subject according to the aforementioned numbers of doses, amounts per dose and/or intervals between dosing. Alternatively, the anti-IL-1β antibody or fragment may be administered as one or more initial doses of the aforementioned amounts that are lower than one or more subsequent dose amounts. By providing the initial dose(s) in a lower amount, the effectiveness and/or tolerability of the treatment may be enhanced. For example, in a non-limiting embodiment of the invention, one or more initial doses (e.g., 1, 2, 3, 4, 5) of an amount of antibody or fragment $\leq 1$ mg/kg (e.g., $\leq 0.9$ mg/kg, $\leq 0.8$ mg/kg, $\leq 0.7$ mg/kg, $\leq 0.6$ mg/kg, $\leq 0.5$ mg/kg, $\leq 0.4$ mg/kg, $\leq 0.3$ mg/kg, $\leq 0.2$ mg/kg, $\leq 0.1$ mg/kg, $\leq 0.05$ mg/kg, $\leq 0.03$ mg/kg, $\leq 0.01$ mg/kg) may be administered, followed by one or more subsequent doses in an amount greater than the initial dose(s) (e.g., ≧0.01 mg/kg, ≧0.03 mg/kg, ≧0.1 mg/kg, ≧0.3 mg/kg, ≧0.5 mg/kg, ≧0.6 mg/kg, ≧0.7 mg/kg, ≧0.8 mg/kg, ≧0.9 mg/kg, ≧1.0 mg/kg, ≧1.5 mg/kg, ≧2 mg/kg, ≧2.5 mg/kg, ≧3 mg/kg, ≧3.5 mg/kg, ≧4 mg/kg, ≧4.5 mg/kg, ≧5 mg/kg). The invention contemplates that each dose of antibody or fragment may be administered at one or more sites.

Methods of treating or preventing a disease or condition in accordance with the present invention may use a pre-determined or "routine" schedule for administration of the antibody or fragment. As used herein a routine schedule refers to a predetermined designated period of time between dose administrations. The routine schedule may encompass periods of time which are identical or which differ in length, as long as the schedule is predetermined. Any particular combination would be covered by the routine schedule as long as it is determined ahead of time that the appropriate schedule involves administration on a certain day.

The invention further contemplates that IL-1β antibodies or fragments used in accordance with the methods provided herein, may be administered in conjunction with more traditional treatment methods and pharmaceutical compositions (e.g., active agents). Such compositions, may include for example, DPP-IV inhibitors, insulin, insulin analogues, PPAR gamma agonists, dual-acting PPAR agonists, GLP-1 agonists or analogues, PTP1B inhibitors, SGLT inhibitors, insulin secretagogues, RXR agonists, glycogen synthase kinase-3 inhibitors, insulin sensitizers, immune modulators, beta-3 adrenergic receptor agonists, Pan-PPAR agonists, 11beta-HSD1 inhibitors, amylin analogues, biguanides, alpha-glucosidase inhibitors, meglitinides, thiazolidinediones, sulfonylureas and the like (see for example Nathan, 2006, N. Engl. J. Med. 355:2477-2480; Kahn et al., 2006, N. Engl. J. Med. 355:2427-2443). In certain embodiments, the antibodies and fragments used in accordance with the invention may prevent or delay the need for additional treatment methods or pharmaceutical compositions. In other embodiments, the antibodies or fragments may reduce the amount, frequency or duration of additional treatment methods or pharmaceutical compositions.

Alternatively, methods of treating or preventing a disease or condition in accordance with the present invention may use a schedule for administration of the antibody or fragment that is based upon the presence of disease symptoms and/or changes in any of the assessments herein (e.g., HbA1c, fasting blood sugar levels, OGTT, glucose/insulin C-peptide AUC, use of diabetes medication, insulin sensitivity, serum cytokine levels, CRP levels, quality of life measurements, BMI improvement) as a means to determine when to administer one or more subsequent doses. Similar, this approach may be used as a means to determine whether a subsequent dose should be increased or decreased, based upon the effect of a previous dose.

Diagnosis of such diseases or conditions in patients, or alternatively the risk for developing such diseases or conditions may be according to standard medical practices known in art. Following administration of an anti-IL-1β antibodies or fragment, clinical assessments for a treatment or preventative effect on the aforementioned diseases and conditions are well known in the art and may be used as a means to monitor the effectiveness of methods of the invention.

For example, response to treatment of Type 2 diabetes may be assessed based on a primary efficacy endpoint of improvement in hemoglobin A1c (HbA1c, see for example Reynolds et al., BMJ, 333(7568):586-589, 2006). Improvements in HbA1c that are indicative of therapeutic efficacy may vary depending on the initial baseline measurement in a patient, with a larger decrease often corresponding to a higher initial baseline and a smaller decrease often corresponding to a lower initial baseline. In one aspect of the invention, the method should result in an HbA1c decrease of at least about 0.5% (e.g., at least about 0.5%, at least about 1%, at least about 1.5%, at least about 2%, at least about 2.5%, at least about 3%, at least about 3.5%, at least about 4% or more) compared with pre-dose levels.

One or more of the following secondary endpoints also may be determined in order to assess efficacy of the treatment, such as for example fasting blood sugar (e.g., glucose) levels (e.g., decrease to ≦130, ≦125, ≦120, ≦115, ≦110, ≦105, ≦100; alternatively decrease of >20%, >30%, >40%, >50%, >60%, >70%, >80%, >90%, >95% compared to pre-dose levels), 120 minute oral glucose tolerance test (OGTT) (e.g., ≦200, ≦190, ≦180, ≦170, ≦160, ≦150, ≦140), glucose/insulin C-peptide AUC (e.g., >25%, >50%, >60%, >70%, >80%, >90%, >100% increase from pre-treatment), reduction in diabetes medication (e.g., insulin, oral hypoglycemic agent), improvement in insulin sensitivity, serum cytokine levels (e.g. normalization), CRP levels (e.g. decrease of ≧0.2, ≧0.4, ≧0.6, ≧0.8, ≧1.0, ≧1.4, ≧1.8, ≧2.2, ≧2.6, ≧3.0 mg/L; alternatively a decrease of >20%, >30%, >40%, >50%, >60%, >70%, >80%, >90%, >95% from pre-treatment) quality of life measurements, BMI improvement (reduction of 1%, 3%, 5%), pharmacokinetics, and the like (Saudek, et al., JAMA, 295:1688-97, 2006; Pfutzner et al., Diabetes Technol Ther. 8:28-36, 2006; Norberg, et al., J Intern Med. 260:263-71, 2006).

Similarly, assessment of efficacy for other diseases or conditions may use one or more of the aforementioned endpoints and/or others known in the art. For example, the effect on hyperglycemia can be assessed by measuring fasting blood sugar (i.e., glucose) levels, the effect on hyperinsulinemia may be assessed by measuring insulin levels and/or C-peptide levels, the effect on obesity may be assessed by measuring weight and/or BMI, and the effect on insulin resistance may be assessed by OGTT.

Alternatively, or in addition, subjects treated in accordance with the invention may experience a decrease in the triglyceride level in the blood of the subject of at least 5%, 10%, 15%, 20%, 25%, 30%, 35%, 40%, 45%, 50%, 55%, 60%, 65%, 70%, or more from the pre-treatment level. Alternatively, or in addition, subjects treated in accordance with the invention may experience a decrease in the level of free fatty acids of at least 5%, 10%, 15%, 20%, 25%, 30%, 35%, 40%, 45%, 50%, 55%, 60%, or more from the pre-treatment level.

EXAMPLES

The following examples are intended merely to further illustrate the practice of the present invention, but should not be construed as in any way limiting its scope. The disclosures of all patent and scientific literatures cited within are hereby expressly incorporated in their entirety by reference.

Example 1

Inhibition of IL-1β Using a High Affinity IL-1β Antibody in an In Vitro Cell Based Assay, with IL-1 Induced Production of IL-8 as a Read-out The inhibitory effect of the IL-1β-specific antibody was compared to a non-antibody inhibitor of the IL-1 pathway, Kineret® (anakinra), which is a recombinant IL-1 receptor antagonist. Fresh, heparinized peripheral blood was collected from healthy donors. 180 µl of whole blood was plated in a 96-well plate and incubated with various concentrations of the antibody AB7 (U.S. application Ser. No. 11/472,813, WO 2007/002261) and 100 pM rhIL-1β. For Kineret®-treated samples, Kineret® and rhIL-1β were combined 1:1 prior to mixing with blood. Samples were incubated for 6 hours at 37° C. with 5% $CO_2$. Whole blood cells were then lysed with 50 µl 2.5% Triton X-100. The concentration of interleukin-8 (IL-8) in cleared lysates was assayed by ELISA (Quantikine human IL-8 ELISA kit, R&D Systems) according to manufacturer's instructions. IL-8 concentrations in AB7 and Kineret® treated samples were compared to a control sample treated with anti-KLH control. The results are depicted in FIG. 1 and summarized in Table 6. $IC_{50}$ is the concentration of antibody required to inhibit 50% of IL-8 released by IL-1β stimulation.

TABLE 1

|  | $IC_{50}$ (pM) |
| --- | --- |
| AB7 | 1.9 pM |
| Kineret ® | 53.4 pM |

These results demonstrate the in vitro potency of AB7, as measured by inhibition of IL-1β stimulated release of IL-8. These results showing greater potency compared with Kineret® indicate that the antibody will have IL-1β inhibitory efficacy in vivo.

Example 2

In Vivo Inhibition of the Biological Activity of Human IL-1β Using IL-1β-Specific Antibodies, as Measured by the Impact on IL-1β Stimulated Release of IL-6

To confirm the in vivo efficacy of AB7, its ability to block the biological activity of human IL-1β was tested in mice. Details of the assay are described in Economides et al., *Nature Med.*, 9: 47-52 (2003). Briefly, male C57/B16 mice (Jackson Laboratory Bar Harbor, Me.) were injected intraperitoneally with titrated doses of AB7, another IL-1β antibody, AB5, or a control antibody. Twenty-four hours after antibody injection, mice were injected subcutaneously with recombinant human IL-1β (rhIL-1β) (from PeproTech Inc., Rocky Hill, N.J.) at a dose of 1 µg/kg. Two hours post-rhIL-1β injection (peak IL-6 response time), mice were sacrificed, and blood was collected and processed for serum. Serum IL-6 levels were assayed by ELISA (BD Pharmingen, Franklin Lakes, N.J.) according to the manufacturer's protocol. Percent inhibition was calculated from the ratio of IL-6 detected in experimental animal serum to IL-6 detected in control animal serum (multiplied by 100).

Figure 2A:
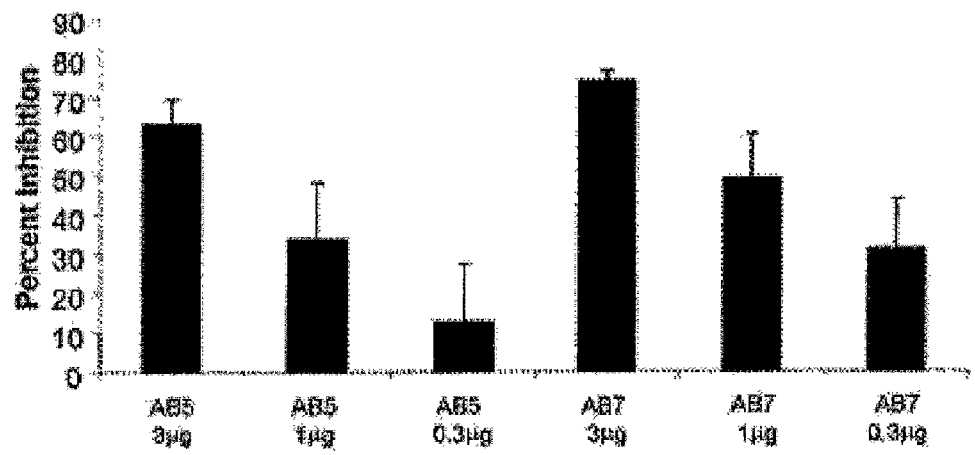
FIG. 2A is a graph showing the results of an in vivo IL-1β inhibition experiment for the antibodies designated AB5 and AB7 involving IL-1 stimulated release of IL-6.

The results are set forth in FIG. 2A. The ability to inhibit the in vivo activity of IL-1β was assessed as a function of IL-1β stimulated IL-6 levels in serum. As illustrated by FIG. 2A, the AB7 and AB5 antibodies were effective for inhibiting the in vivo activity of human IL-1β. These results also show that a single injection of AB7 or AB5 can block the systemic action to IL-1β stimulation and that such antibodies are useful for the inhibition of IL-1β activity in vivo.

Figure 2B:
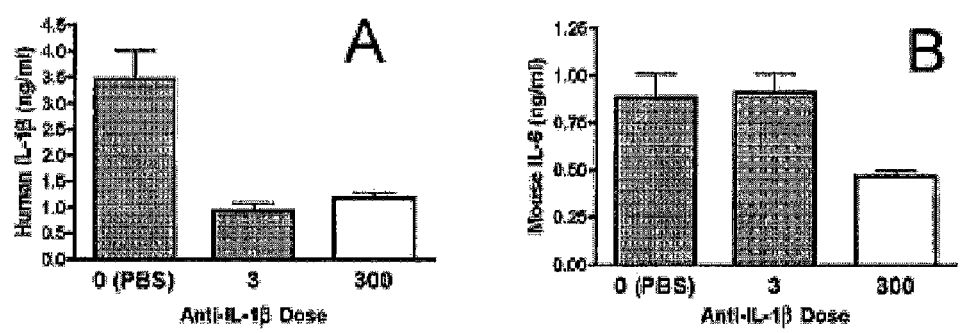
FIG. 2B is a graph showing the results of an in vivo IL-1β inhibition experiment for the antibodies designated AB7 involving IL-1 stimulated release of IL-6, and comparing inhibition of human (panel A) versus mouse (panel B) IL-1β.

A similar experiment was performed to further demonstrate the ability of AB7 to neutralize mouse IL-1β in vivo, to support the use of this antibody in mouse models of disease. It was determined that AB7 has an affinity for human IL-1β that is ~10,000 times greater than the affinity for mouse IL-1β, and an in vitro potency in the D 10.G4.1 assay that is ~1,000 times greater than that for mouse IL-1β. In the C57BL/6 mouse model with IL-6 readout, the mice were injected with AB7 (3 or 300 ug) or PBS vehicle control i.p. 24 hours before a s.c. injection of human (FIG. 2B, panel A) or mouse (FIG. 2B, panel B) IL-1β (20 ng). Blood was drawn 2 hours later and serum samples were analyzed for IL-6 levels via ELISA. These data show maximum suppression of IL-6 levels (~75%) induced by human IL-1β at 3 µg (panel A), whereas submaximum suppression of IL-6 levels (~50%) induced by mouse IL-1β was demonstrated with 300 g (panel B). These results are consistent with the observation of far greater affinity and in vitro potency of the AB7 antibody for human IL-1β, as compared to mouse IL-1β. In addition, the data indicate that this antibody may be used for mouse in vivo disease models with an appropriate higher dose than would be needed for treatment of human subjects, where the antibody has far superior affinity and potency. In the case of other IL-1β antibodies, such as for example antibodies disclosed and/or cited herein, that do not exhibit such a property of significantly higher affinity and in vitro potency for human IL-1β as compared to mouse IL-1β, similar higher doses in mouse models may not be necessary.

Example 3

Pharmacokinetics of an Anti-IL-1β Antibody Following Administration of a Single Intravenous or Subcutaneous Dose to Rats To examine the pharmacokinetic profile, an IL-1β antibody designated AB7 was administered to adult male rats as an intravenous (IV) bolus into the tail vein at doses of 0.1, 1.0, or 10 mg/kg (Groups 1, 2, and 3 respectively) or a subcutaneous (SC) dose between the shoulder blades at 1.0 mg/kg (Group 4). Blood samples were collected via the jugular vein cannula or the retro-orbital sinus at specified times for up to 91 days after dosing. Blood samples were centrifuged to obtain serum. Samples were analyzed for the concentration of anti-IL-1β antibody using an alkaline phosphatase-based ELISA assay as follows.

IL-1β (Preprotech) was diluted to 0.5 µg/mL in PBS and 50 µL of this solution was added to wells of Nunc-Immuno Maxisorp microtiter plates (VWR) and incubated overnight at 2-8° C. The antigen solution was removed and 200 µL of blocking buffer [1% bovine serum albumin (BSA) in 1×PBS containing 0.05% Tween 20] was added to all wells and incubated for 1 hour at room temperature. After blocking, the wells were washed three times with wash buffer (1×PBS, containing 0.05% Tween 20). Standards, samples and controls were diluted in sample diluent (25% Rat Serum in 1×PBS containing 1% BSA and 0.05% Tween 20). Anti-IL-1β antibody standard solutions were prepared as serial two-fold dilutions from 2000 to 0.24 ng/mL. Each replicate and dilution of the standards, samples and controls (50 µL) were transferred to the blocked microtiter plates and incubated for 1 hour at 37° C. After incubation, the wells were washed 3 times with wash buffer. Alkaline phosphatase conjugated goat anti-human IgG (H+L) antibody (Southern Biotech Associates Inc, Birmingham, Ala.) was diluted 1/1000 in conjugate diluent (1% BSA in 1×PBS containing 0.05% Tween 20). Fifty µL of the diluted conjugate was added to all wells except for the BLANK wells, which received 50 µL of conjugate diluent only. The plates were incubated for 1 hour at 37° C. and then all wells were washed 3 times with wash buffer and 3 times with deionized water. The substrate p-nitrophenylphosphate (1 mg/mL in 10% diethanolamine buffer, pH 9.8) was added to all wells and color development was allowed to proceed for 1 hour at room temperature, after which 50 µL of 1 N NaOH was added to stop the reaction. The absorbance at 405 nm was determined using a SPECTRAmax M2 Plate Reader (Molecular Devices, Menlo Park, Calif.) and a standard curve was then plotted as $A_{405}$ versus ng/mL of antibody standard. A regression analysis was performed and concentrations were determined for samples and controls by interpolation from the standard curve. The limit of quantification was 40 ng/mL.

Figure 3:
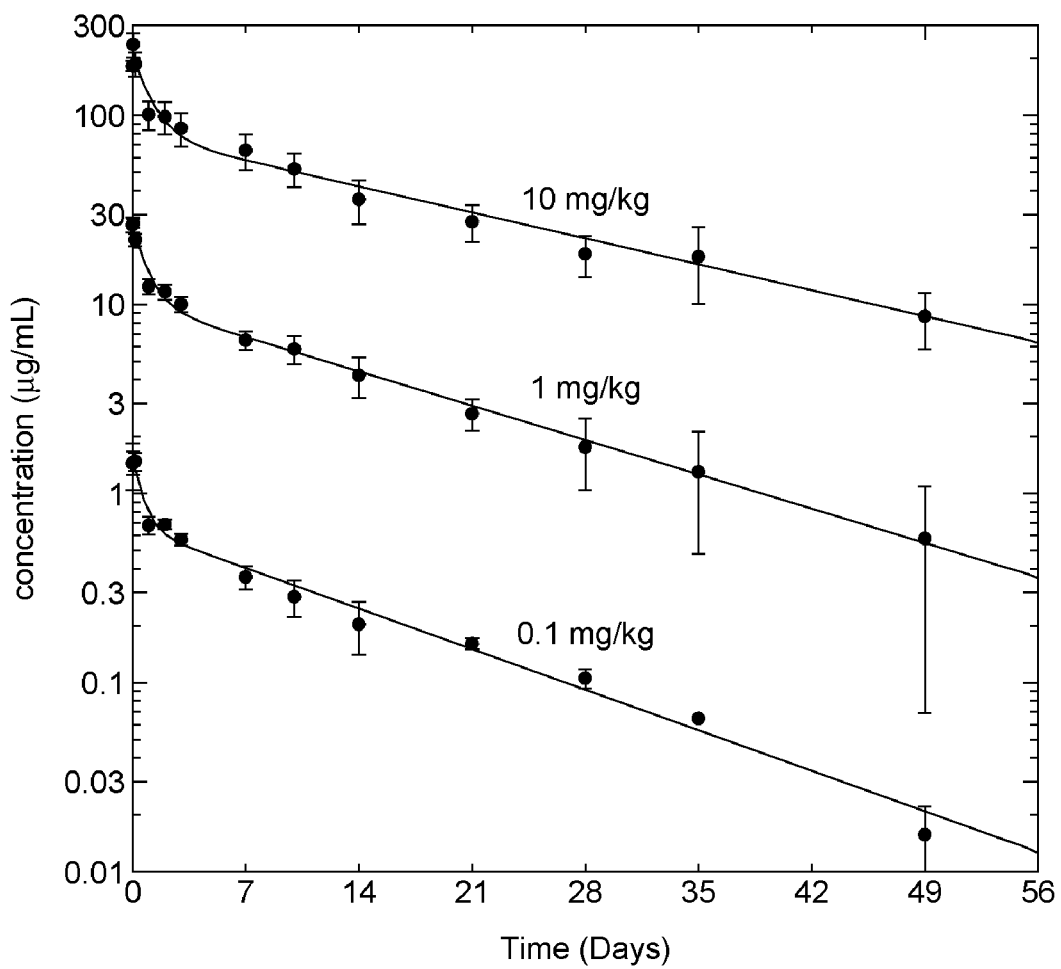
FIG. 3 is a graph showing serum concentrations following administration 0.1, 1 or 10 mg/kg of an anti-IL-1β antibody in rats.
Figure 4:
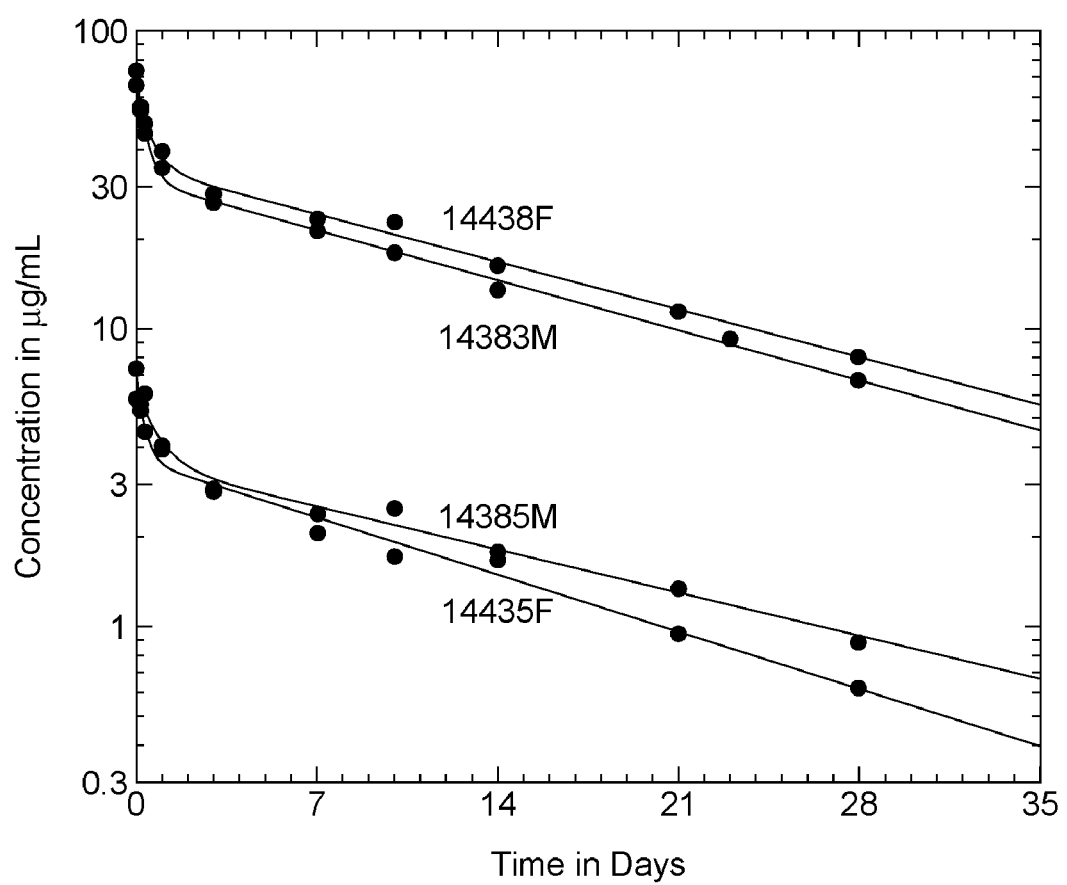
FIG. 4 is a graph showing serum concentrations following administration of 0.3 or 3 mg/kg of an anti-IL-1β antibody in Cynomolgus monkeys.

As shown in FIG. 3, serum concentrations declined bi-exponentially among the IV dose groups. A compartmental analysis was performed on the individual animal data, and resulting pharmacokinetic parameters were averaged for each dose group excluding those animals in which a RAHA response was generated. The serum levels of anti-IL-1β antibody declined with an average alpha phase half-life of 0.189±0.094 to 0.429±0.043 days (4.54 to 10.3 hours) and a beta phase half-life of 9.68±0.70 to 14.5±1.7 days. Among rats receiving a 1 mg/kg subcutaneous dose of AB7 serum levels increased to a peak of 4.26±0.065 µg/mL by 2-3 days, and declined with a half-life of 2.59±0.25 days.

Example 4

Pharmacokinetics of an Anti-IL-1β Antibody Following Administration of a Single Intravenous Dose to Cynomolgus Monkeys Adult male and female cynomolgus monkeys received the anti-IL-1β antibody designated AB7 as an intravenous (IV) single bolus injection at doses of 0.3, 3.0, or 30 mg/kg. Blood samples were collected from animals prior to dose, 5 minutes, 4 and 8 hours post dose on Day 1, and Days 2, 4, 8, 11, 15, 22, 29, 43 and 56. Samples were analyzed for the concentration of anti-IL-1β antibody using an alkaline phosphatase-based ELISA assay as follows.

IL-1β solution was diluted to 0.5 µg/mL in PBS and 50 µL of this solution was added to wells of Nunc-Immuno Maxisorp microtiter plates (VWR) and incubated overnight at 2-8° C. The antigen solution was removed and 200 µL of blocking buffer [1% bovine serum albumin (BSA) in 1×PBS containing 0.05% Tween 20] was added to all wells and then incubated for 1-4 hours at room temperature. After blocking, the wells of each plate were washed three times with wash buffer (1×PBS, containing 0.05% Tween 20). Standards, samples, and controls were diluted in sample diluent (2% Normal Cynomolgus Serum (NCS) in 1×PBS containing 1% BSA and 0.05% Tween 20). Anti-IL-1β standard solutions were prepared as serial two-fold dilutions from 8000 ng/mL. Each replicate and dilution of the standards, samples, and controls (50 µL) were transferred to the blocked microtiter plates and incubated for 1 hour at 37° C. After the primary incubation, the wells were washed 3 times with wash buffer and 50 µL of biotinylated rhIL-1 beta was added to all wells. The plates were then incubated for 1 hour at 37° C. The wells were washed 3 times with wash buffer and a tertiary incubation with fifty µL of diluted alkaline phosphatase conjugated streptavidin was added to all wells except for the BLANK wells, which received 50 µL of diluent only. The plates were incubated for 30 minutes at 37° C., and then all wells were washed 3 times with wash buffer and 3 times with deionized water. The substrate p-nitrophenylphosphate (1 mg/mL in 10% diethanolamine buffer, pH 9.8) was added to all wells. Color development was allowed to proceed in the dark for 1 hour at room temperature, after which 50 µL of 1 N NaOH was added to stop the reaction. The absorbance at 405 nm was determined for all wells using a SPECTRAmax M2 Plate Reader (Molecular Devices, Menlo Park, Calif.). A standard curve was then plotted as $A_{405}$ versus ng/mL of anti-IL-1β standard. A 4-parameter regression analysis was performed and concentrations were determined for samples and controls by interpolation from the standard curve. The limit of quantification was 40 ng/mL.

Figure 5:
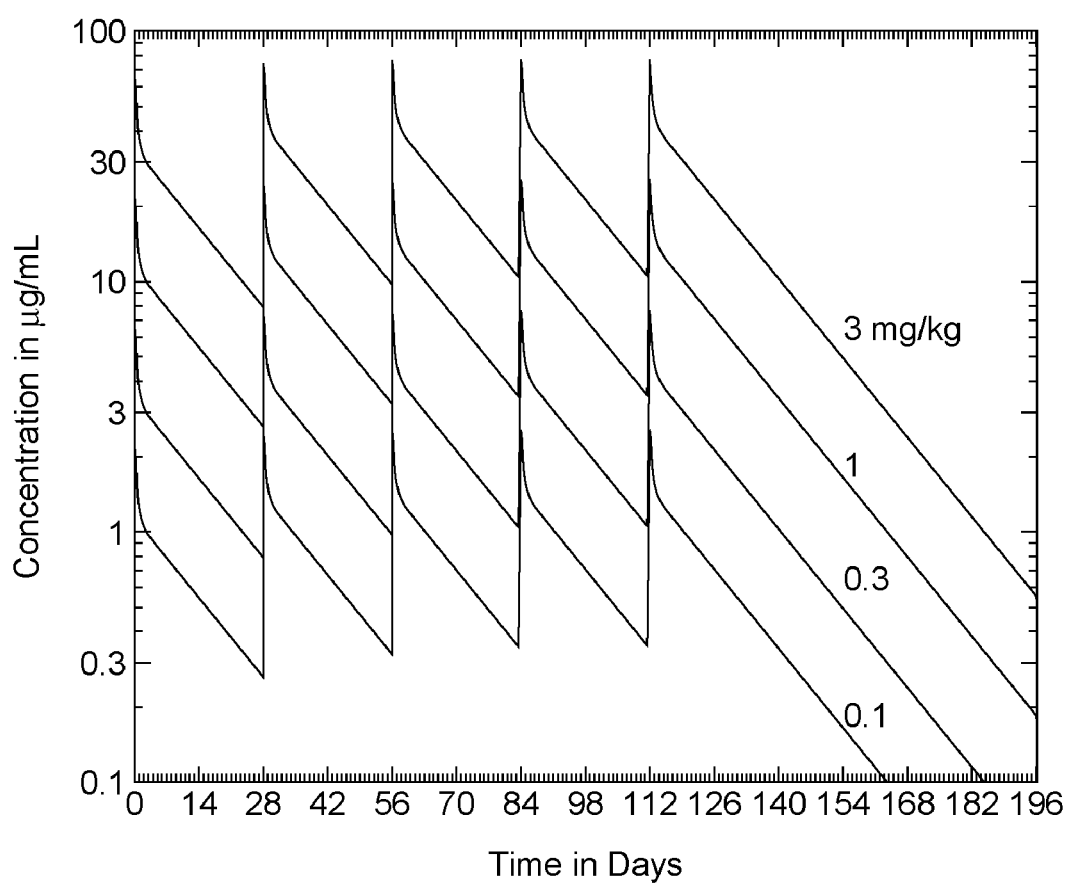
FIG. 5 is a graph modeling plasma concentration profiles of an anti-IL-1β antibody in Cynomolgus monkeys following five monthly doses of 0.1, 0.3, 1 or 3 mg/kg.

For the single dose 0.3 and 3 mg/kg groups, the serum anti-IL-1β antibody levels declined with an average alpha phase half-life of 9.40±2.00 hours, followed by a beta phase half-life of 13.3±1.0 days (FIG. 5). In cynomolgus monkeys receiving a single IV injection of 30 mg/kg, serum levels of antibody declined more rapidly, with alpha phase half life of 10.9±3.2 hours, followed by a beta phase half-life of 7.54±1.79 days. Modeling of plasma concentration-time profiles of 0.1, 0.3, 1 and 10 mg/kg doses administered at five monthly intervals also was performed and is shown in FIG. 5.

Example 5

Effect of anti-IL-1β Antibodies in a Human Islet Cell Assay System

As an in vitro model, human islet cells are isolated and then treated with high glucose levels to mimic the Type 2 diabetic environment. Anti-IL-1β antibodies may be used in the islet cell system to examine the effect on beta cell function (insulin release in response to glucose), beta cell proliferation and apoptosis.

Islets are isolated from the pancreases of multiple human organ donors with no history of diabetes or metabolic disease as described (Linetsky et al., Diabetes 46:1120-1123, 1997; Oberholzer et al., Transplantation 69:1115-1123, 2000; Ricordi et al., Diabetes 37:413-420, 1988, Maedler et al., Proc. Natl. Acad. Sci. USA 101:8138-8143, 2004; WO 2004/0002512). The islets are then cultured on extracellular matrix-coated plates derived from bovine corneal endothelial cells (Novamed Ltd, Jerusalem), allowing the cells to attach to the plates and preserving their functional integrity. The islets are cultured in CMRL 1066 medium containing 100 U/mL penicillin, 100 ug/mL streptomycin and 10% fetal bovine serum (GIBCO, Gaithersburg, Md.). To stimulate insulin secretion, the culture medium is replaced with culture medium further supplemented with 5, 11 or 33 mM glucose, with or without addition of fatty acid.

To measure insulin release in response glucose, islet cells are washed and pre-incubated for 30 minutes in Krebs-Ringer bicarbonate buffer (KRB) containing 3.3 mM glucose and 0.5% BSA. KRB is then replaced by KRB 3.3 mM glucose for 1 hr. which is then followed by an additional 1 hr in KRB 16.7 mM glucose. Islet cells are extracted with 0.18 M HCl in 70% ethanol for determination of insulin content using a human insulin RIA kit (CIS Biointernational, Gif-sur-Yvette, France). Beta cell apoptosis may be measured by a variety of methods. For example, cells are double stained by the standard terminal deoxynucleotidyl transferase-mediated dUTP nic-end labeling (TUNEL) technique and also for insulin. In parallel, apoptosis also is confirmed by detection of caspase 3 activation or Fas expression as described (see for example, WO 2004/002512; Maedler et al., 2004, ibid).

Example 6

Effect of Anti-IL-1β Antibodies in a Rat Pseudo Islet Cell Assay System

Alternatively or in addition to the human islet cell model, rat pseudo islet cells may be used as an in vitro model to evaluate the effects of anti-IL-1β antibodies. For example, pseudo islets may be prepared and tested as described in US 20060094714. Pancreata from four Sprague Dawley rats are divided into small pieces, rinsed three times with Hanks-Hepes buffer, and digested with collagenase (Liberase, 0.25 mg/ml, Roche Diagnostic Corp., Indianapolis, Ind., USA) at 37° C. in a water bath shaker for 10 minutes. The digested pancreata tissue is then rinsed three times with 50 ml of Hanks-Hepes buffer to remove the collagenase and the tissue pellet is then filtered through a 250 micron filter. The filtrate is mixed with 16 ml of 27% Ficoll (Sigma, St. Louis, Mo., USA) w/v in Hanks-Hepes buffer and then centrifuged in a Ficoll gradient (23%, 20.5%, and 11%, respectively; 8 ml of each concentration) at 1,600 rpm for 10 minutes at room temperature. The pancreatic islets are concentrated at the interphase between 11% and 20.5%, and between 20.5% and 23% depending on the size of islets. The islets are collected from the two interphases, rinsed twice with calcium-free Hanks-Hepes buffer, and then suspended in 5 ml calcium-free Hanks-Hepes buffer containing 1 mM EDTA and incubated for 8 minutes at room temperature. Trypsin and DNAse I are added to the islet suspension for a final concentration of 25 ug/ml and 2 ug/ml, respectively, and the suspension is incubated with shaking at 30° C. for 10 minutes. The trypsin digestion is stopped by adding 40 ml RPMI 1640 (GIBCO Life Technologies, Invitrogen, Carlsbad, Calif.) with 10% FBS. The trypsin digested islet cells are then filtered through a 63 micron nylon filter (PGC Scientific, Frederick, Md.) to remove large cell clusters. The dispersed islet cells are then washed, counted, and seeded into "V-bottom" 96-well plates (2,500 cells per well). The dispersed islet cell suspension is then centrifuged at 1,000 rpm for 5 minutes. The Hanks-Hepes buffer is removed and replaced with 200 ul RPMI 1640 medium containing 10% FBS, 1% Penicillin-Streptomycin, and 2 mM L-glutamine. Next, the 96-well plates are centrifuged at 1,000 rpm for 5 minutes to collect the dispersed islet cells concentrated at the V-bottom of the plate forming pseudo islets. These pseudo islets are then cultured overnight in a cell culture incubator at 37° C. with 5% $CO_2$, and then used for assays.

Example 7

Effect of an IL-1β Antibody on Insulin Sensitivity in an Animal Model

In vivo efficacy of an IL-1β antibody as an insulin-sensitizing agent may be measured as the insulin and glucose-lowering activity of the antibody in a dietary model of insulin resistance. Male Sprague-Dawley rats are placed on a high fat, high carbohydrate diet, containing 60% fructose, 10% lard, and 0.06% magnesium at 6 weeks of age. Two days after starting the diet, the rats are randomized into different groups based on antibody dose levels (ranging from 0.1 to 5 mg/kg body weight), route of administration (subcutaneous, intravenous, or intraperitoneal routes), and frequency of administration (daily to bi-weekly). Control groups receive either buffer (vehicle) only or an irrelevant antibody. Food and fluid intakes are measured each day and a pair-feeding protocol is utilized to insure equivalent food intakes among the 3 groups. After 5 weeks, serum levels of glucose, insulin, and triglycerides are obtained in the semi-fasting state (the night before blood draw, animals are given a restricted amount of food) and blood is drawn the following morning. The protocol is continued for an additional 9 weeks at which time glucose tolerance testing (OGTT) is performed in conscious animals in the semi-fasted state by sampling blood for glucose and insulin measurements after oral administration of a glucose load (100 mg/100 gram body weight). Serum levels of glucose and triglycerides are measured by spectrophotometric methods and insulin levels are measured by radioimmunoassay (Linco, St. Louis, Mo.).

Example 8

IL-1β Antibodies for Treatment in a *Psammomys obesus* Animal Model of T2D

The therapeutic effectiveness of an IL-1β antibody for preventing the decline of β-cell mass observed in Type 2 diabetes patients is evaluated in the gerbil *Psammomys obesus*, which shows insulin resistance and develops diet-induced obesity-linked diabetes, initially associated with hyperinsulinemia, and gradually progressing to severe hyperglycemia, accompanied by a transient increase in beta-cell proliferative activity and by a prolonged increase in the rate of beta-cell death, with disruption of islet architecture (Donath et al., Diabetes 48:738-744, 1999). To determine the effect of IL-1β antibody on hyperglycemia-induced beta-cell apoptosis and impaired proliferation in pancreatic islets of *Psammomys obesus* during development of diabetes, antibody is administered to the diabetes-prone animals (switched to a high energy diet) at multiple dose levels ranging from 0.1 to 5 mg/kg body weight by the subcutaneous, intravenous, or intraperitoneal routes, with the antibody administrations repeated at intervals ranging from daily to weekly. Control groups of animals are either maintained on a low energy diet or switched to a high energy diet and treated with buffer (vehicle) only or an irrelevant antibody. Subgroups of animals are sacrificed on days 4, 7, 14, 21, and 28, whereupon blood is collected and used to determine plasma glucose, insulin and triglyerides. The pancreas is also removed, with a portion frozen at −70 C for later determination of insulin content and the remaining portion fixed in 10% phosphate buffered formalin, embedded in paraffin and sectioned for analysis of Fas, IL-1β and insulin expression, and beta-cell proliferation and apoptosis. Such analysis will allow determination of the prevention or delay in diabetes onset, protection from hyperglycemia-induced beta-cell apoptosis, impaired proliferation and decreased β-cell mass, and normalization of pancreatic insulin content.

Example 9

Use of an IL-1β Antibody in the Treatment of T2D in Humans

IL-1β antibodies or fragments described herein may be administered to a human patient in accordance with the invention for therapeutic treatment and/or prevention of Type 2 diabetes. Specifically, in one example, an IL-1β antibody having the aforementioned properties (AB7, described above) is used for the therapeutic treatment of patients displaying signs and symptoms of Type 2 diabetes. More specifically, safety and effectiveness of an IL-1β antibody for Type 2 diabetes are demonstrated in one or more human clinical studies, including for example a trial of the following design.

A double-blind, placebo controlled human clinical study is performed in Type 2 diabetes patients. Patients who meet inclusion criteria for this study according to the American Diabetes Association (ADA) diagnostic criteria for T2D:

Fasting blood glucose concentration ≧126 mg/dL (≧7.0 mmol/L) (must be measured within 28 days prior to Day 0)

OR

Symptoms of hyperglycemia (e.g., thirst, polyuria, weight loss, visual blurring) AND a casual/random plasma glucose value of ≧200 mg/dL (≧11.1 mmol/L) (must be measured within 28 days prior to Day 0), and with an HbA1c >7.5% and ≦12% (DCCT standard), are enrolled in the study sequentially by study group and within each group are randomly assigned to receive the IL-1β antibody or placebo. To minimize risk to subjects, safety and tolerability are reviewed at each dose level prior to escalating to the next dose level. The treatment groups and numbers of subjects for the study are shown in the following table:

| Group | Route | Antibody # Subjects | Antibody Dose | Placebo # Subjects |
|---|---|---|---|---|
| 1 | IV or SC | 5 | 0.01 mg/kg | 1 |
| 2 | IV or SC | 5 | 0.03 mg/kg | 1 |
| 3 | IV or SC | 5 | 0.1 mg/kg | 1 |
| 4 | IV or SC | 5 | 0.3 mg/kg | 1 |
| 5 | IV or SC | 5 | 1.0 mg/kg | 1 |
| 6 | IV or SC | 5 | 3.0 mg/kg | 1 |

On study Day 1, antibody or placebo is administered either subcutaneously or via a 30 minute constant rate intravenous infusion. Safety assessments, including the recording of adverse events, physical examinations, vital signs, clinical laboratory tests (e.g., blood chemistry, hematology, urinalysis), plasma cytokine levels, and electrocardiograms (ECGs) are conducted using standard medical practices known in the art. Blood samples are collected pre-dose administration and at multiple time periods (e.g., days) post-administration to assess HbA1c, lipid profile including free fatty acids, HDL and LDL cholesterol, IL-1β antibody levels (pharmacokinetics), anti-IL-1β antibody responses, cytokine (e.g., IL-1β, IL-6, TNFα) levels, CRP, sodium, potassium, creatinine, AST, ALT and hematogram. Assays may also be performed for other cytokines and lymphokines, such as for example, those described herein. Additional blood samples may be collected at later days than initially designed in those instances when levels of the administered IL-1β antibody have not fallen below the limit of detection. Study assessments are conducted at specified times post-treatment.

Clinical monitoring of treatment for Type 2 diabetes is performed based on a primary efficacy endpoint of improvement in hemoglobin A1c (HbA1c, see for example Reynolds et al., BMJ, 333(7568):586-589, 2006). Improvement in HbA1c level is indicative of therapeutic efficacy of the anti-IL-1b treatment and generally should result in a decrease at least about of 0.5% or more. One or more of the following secondary endpoints are also determined to assess efficacy of the treatment for Type 2 diabetes, such as for example fasting blood sugar (e.g., glucose) levels (e.g., ≦130, ≦120), 120 minute oral glucose tolerance test (OGTT), glucose/insulin C-peptide AUC (e.g., >50%, >60% increase), reduction in diabetes medication (e.g., insulin, oral hypoglycemic agent), improvement in insulin sensitivity, serum cytokine levels (e.g. normalization), CRP levels, quality of life measurements, BMI improvement (reduction 1%, 3%, 5%), pharmacokinetics, and the like (Saudek, et al., JAMA, 295:1688-97, 2006; Pfutzner et al., Diabetes Technol Ther. 8:28-36, 2006; Norberg, et al., J Intern Med. 260:263-71, 2006). Additional lipid profile analysis of samples includes the following tests performed according to standard accepted methods known in the art.

| Test | Method |
|---|---|
| Lipoprotein electrophoresis | Gel Electrophoresis |
| Serum apolipoprotein A-I (apoA-I) | Nephelometry |
| Serum apolipoprotein A-II (apo A-II) | Nephelometry |
| Serum apolipoprotein B-48 (apo B-48) | ELISA |
| Serum apolipoprotein B-100 (apo B-100) | Nephelometry |
| Serum apolipoprotein Cs (apo Cs) | Immunoturbidimetry for Apo CII and ApoCIII |
| Serum apolipoprotein E (apo E) | Nephelometry |
| Serum apolipoprotein J (apo J) | ELISA |
| Serum amyloid A | Nephelometry |
| Plasma free fatty acids (FFA) | Colorimetry |
| Plasma glycerol | Colorimetry |
| Serum LCAT | ELISA |
| Serum cholesteryl ester transfer protein (CETP) | ELISA |
| Serum hepatic lipase (HL) | Fluorometry |
| Serum paraoxonase 1 (PON1) | UV/colorimetry |

Pharmacokinetic Analysis

Figure 7:
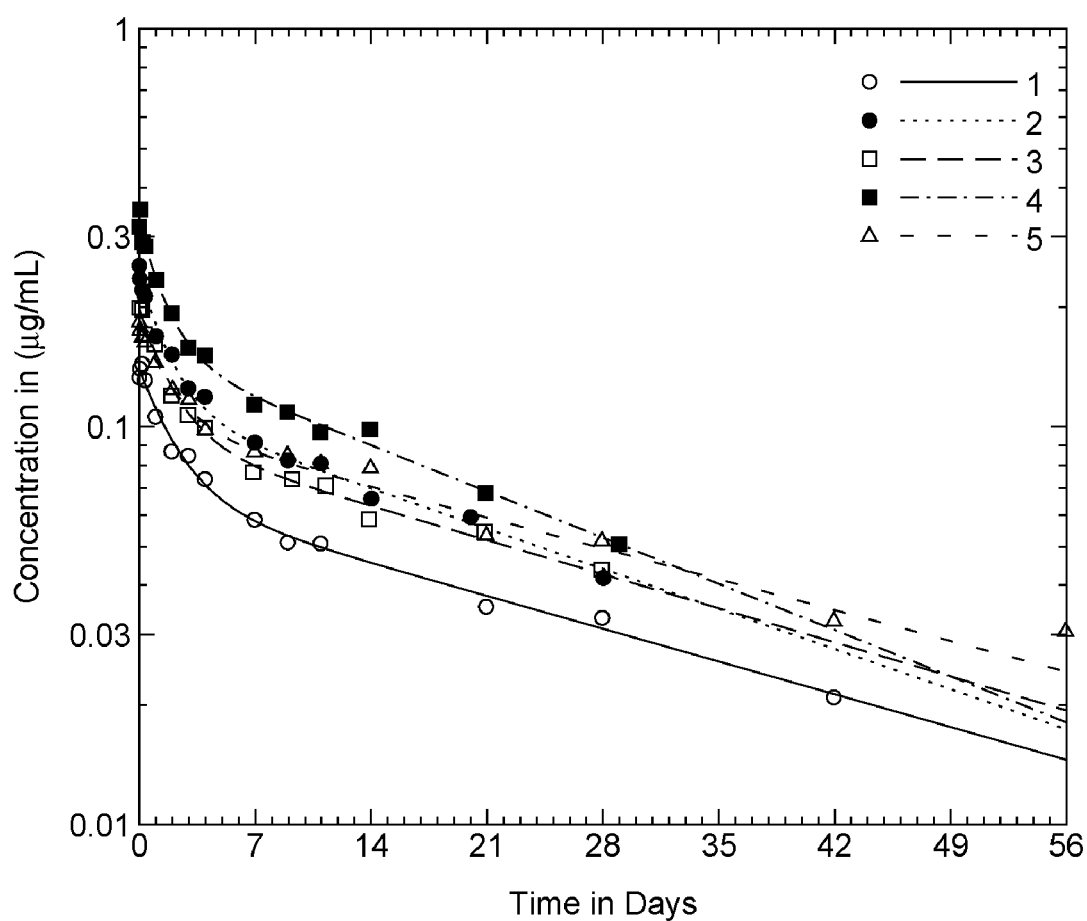
FIG. 7 is a graph showing the pharmacokinetics of AB7 in humans following administration of a dose of 0.01 mg/kg of antibody.

Samples are obtained for pharmacokinetic analysis at days 0, 1, 2, 3, 4, 7, 9±1, 11±1, 14±1, 21±2, 28±2, 42±3, and 56±3. Preliminary analysis of the pharmacokinetics of AB7 in Type 2 diabetes subjects receiving a single IV dose of 0.01 mg/kg showed serum concentration-time profiles with a terminal half-life of 22 days, clearance of 2.9 mL/day/kg and volume of distribution of the central compartment of 50 mL/kg, very similar to serum volume (FIG. 7).

Blood Glucose and HbA1c Analysis

Samples are obtained and blood glucose measured at days 0, 7, 14±1, 21±2, 28±2, 42±3, and 56±3, as well as the screening day. Assessment of these samples for a decrease in blood glucose levels is shown below for samples from the first two dose cohorts (upper data line for each subject). Samples are obtained and HbA1c measured at days 0, 28±2, 42±3, and 56±3, as well as the screening day. Assessment of these samples for a decrease in HbA1c levels is shown below for samples from the first two dose cohorts (lower data line for each subject).

| | | Cohort at 0.01 mg/kg dose | | | | | | |
|---|---|---|---|---|---|---|---|---|
| Subject | Screen | Day 0 Labs | Day 7 Labs | Day 14 Labs | Day 21 Labs | Day 28 Labs | Day 42 Labs | Day 56 Labs |
| 5 | 200.00 | 247.00 | 212.00 | 179.00 | 213.00 | 242.00 | 235.00 | 200.00 |
|   | 8.40 | 8.60 | | | | 8.50 | 7.10 | 9.30 |
| 1 | 211.00 | 232.00 | 235.00 | 236.00 | 199.00 | 221.00 | 252.00 | 204.00 |
|   | 9.30 | 9.60 | | | | 9.50 | 9.10 | 9.80 |

-continued

Cohort at 0.01 mg/kg dose

| Subject | Screen | Day 0 Labs | Day 7 Labs | Day 14 Labs | Day 21 Labs | Day 28 Labs | Day 42 Labs | Day 56 Labs |
|---|---|---|---|---|---|---|---|---|
| 2 | 229.00 | 131.00 | 160.00 | 191.00 | 193.00 | 224.00 | 204.00 | 207.00 |
|   | 9.00 | 8.80 |   |   |   | 8.40 | 8.60 | 9.00 |
| 11 | 290.00 | 283.00 | 300.00 | 177.00 | 308.00 | 278.00 | 292.00 | 302.00 |
|   | 11.80 | 11.60 |   |   |   | 11.40 | 11.20 | 11.80 |
| 3 | 175.00 | 158.00 | 175.00 | 154.00 | 154.00 | 162.00 | 183.00 | 170.00 |
|   | 8.20 | 8.20 |   |   |   | 7.70 | 7.80 | 8.10 |
| 4 | 238.00 | 255.00 | 270.00 | 275.00 | 289.00 | 278.00 | 255.00 | 245.00 |
|   | 8.50 | 9.40 |   |   |   | 10.50 | 10.60 | 10.40 |

Cohort at 0.03 mg/kg dose

| Subject | Screen | Day 0 Labs | Day 7 Labs | Day 14 Labs | Day 21 Labs | Day 28 Labs | Day 42 Labs | Day 56 Labs |
|---|---|---|---|---|---|---|---|---|
| 6 | 222.00 | 164.00 | 148.00 | 166.00 | 162.00 | 145.00 | 207.00 |   |
|   | 8.40 | 8.40 |   |   |   | 8.20 | 8.40 |   |
| 7 | 208.00 | 109.00 | 101.00 | 120.00 | 81.00 | 108.00 | 113.00 |   |
|   | 8.00 | 7.50 |   |   |   | 6.70 | 6.40 |   |
| 8 | 364.00 | 287.00 | 289.00 | 260.00 | 237.00 |   |   |   |
|   | 12.40 | 12.00 |   |   |   |   |   |   |
| 9 | 204.00 | 128.00 | 124.00 | 117.00 | 112.00 | 113.00 |   |   |
|   | 7.90 | 7.50 |   |   |   | 7.10 |   |   |
| 12 | 275.00 | 235.00 | 250.00 | 126.00 | 168.00 |   |   |   |
|   | 9.90 | 10.30 |   |   |   |   |   |   |
| 10 | 332.00 | 398.00 | 243.00 | 187.00 | 220.00 |   |   |   |
|   | 11.50 | 11.50 |   |   |   |   |   |   |

These data indicate the lower boundaries of a dose of IL-1β antibody as provided herein, useful to achieve a therapeutic effect (e.g., decrease in glucose and/or HbA1c levels) in a subject following a single administration of antibody.

C-Reactive Protein Analysis

Figure 8:
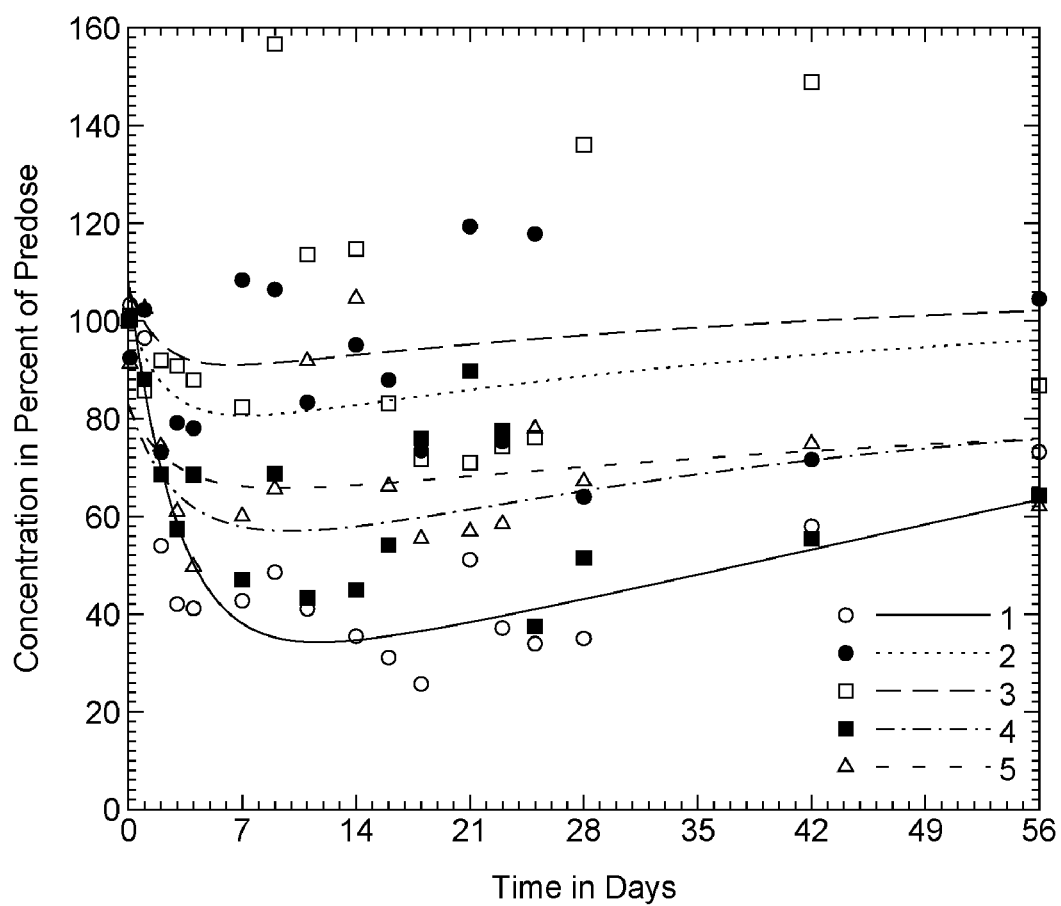
FIG. 8 is a graph showing the effect on reducing CRP levels in humans following administration of a 0.01 mg/kg dose of AB7.
Figure 9:
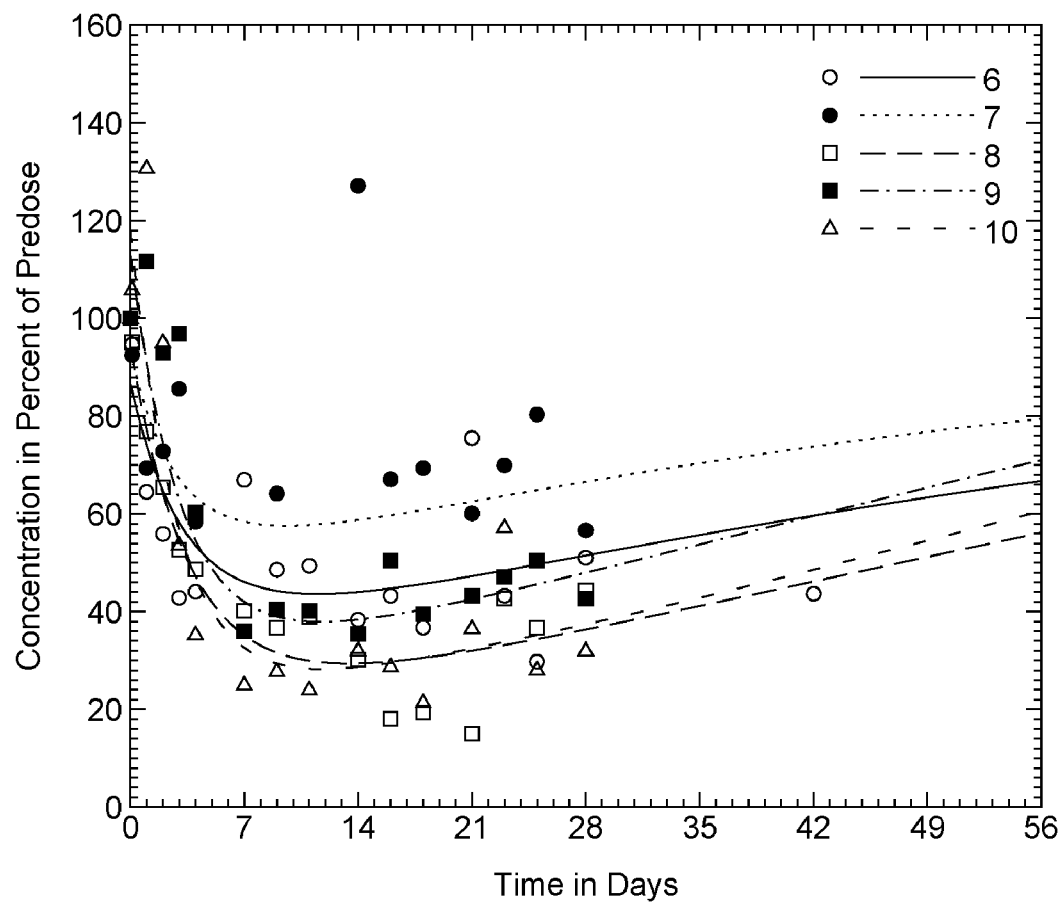
FIG. 9 is a graph showing the effect on reducing CRP levels in humans following administration of a 0.03 mg/kg dose of AB7.
Figure 10:
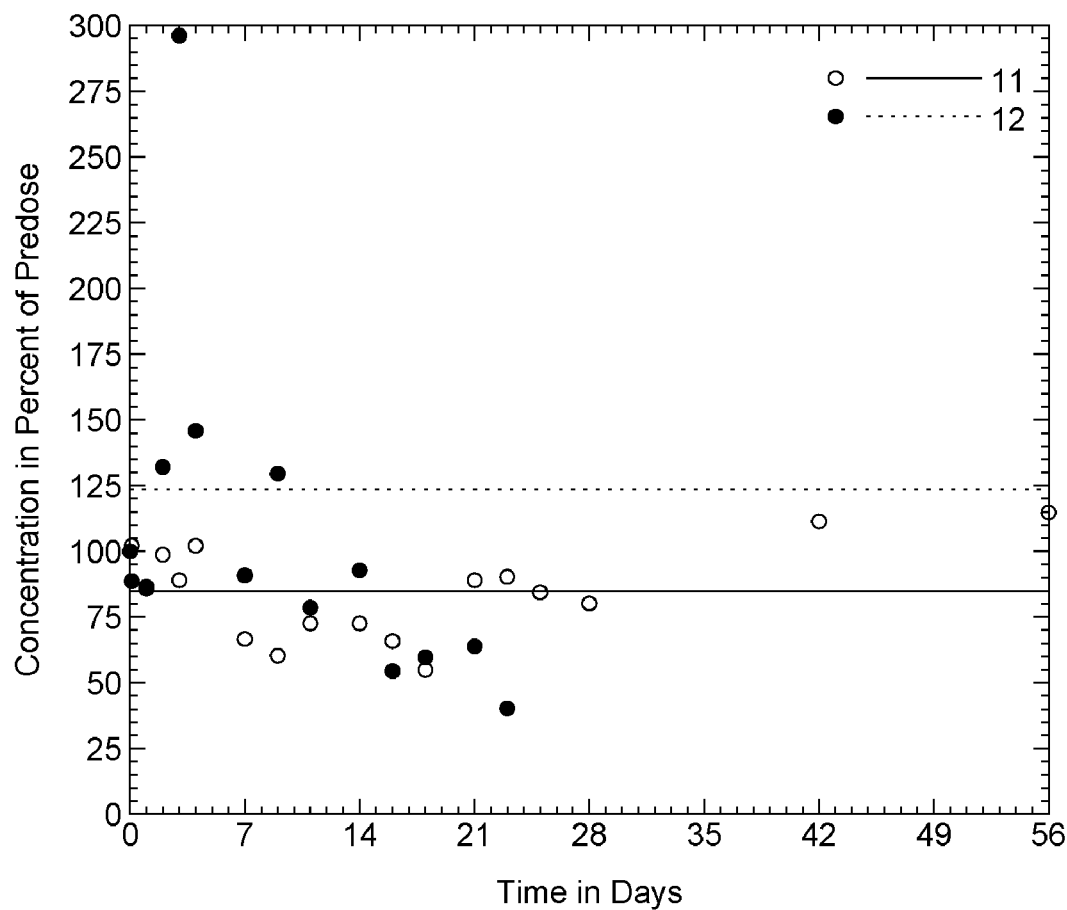
FIG. 10 is a graph showing CRP levels in placebo controls from the 0.01 and 0.03 mg/kg dose cohorts
Figure 11:
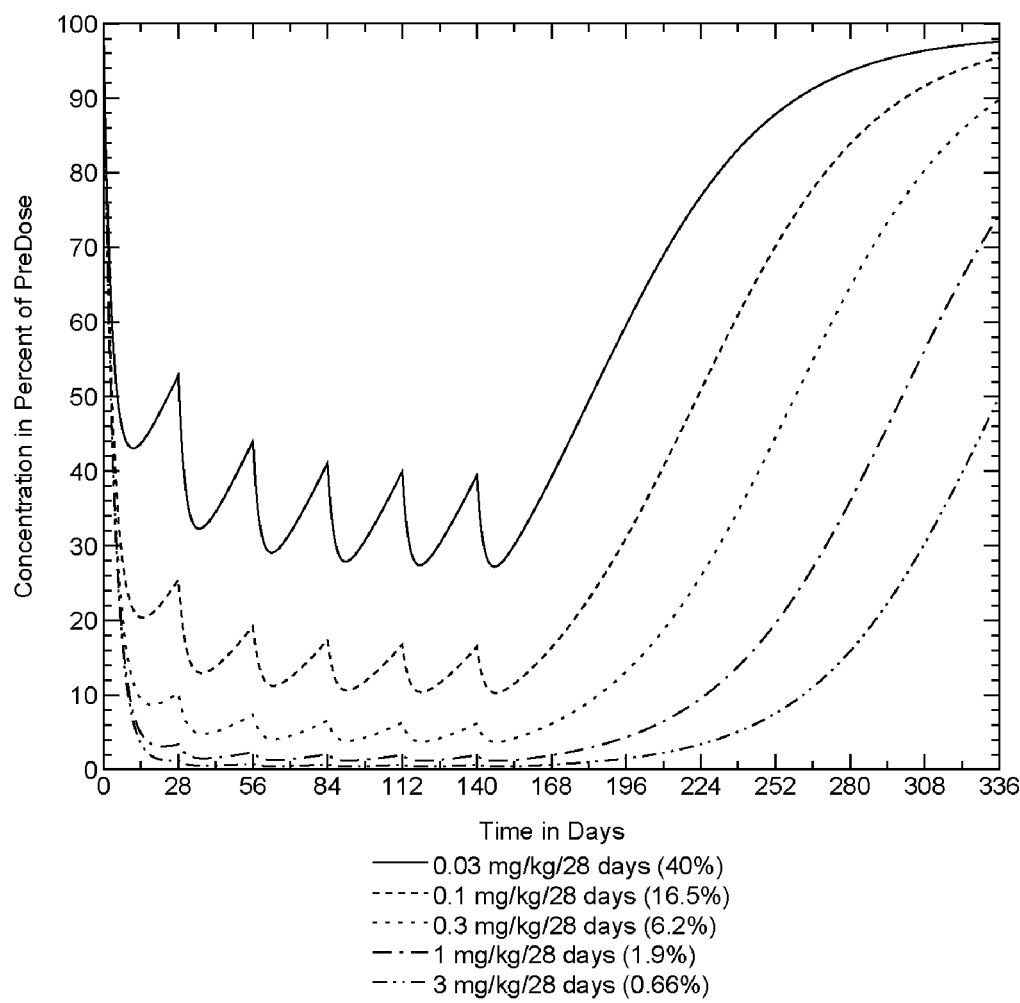
FIG. 11 is a graph modeling the effect on CRP levels in humans following administration of various doses of an antibody with properties similar to AB7 at 28 day intervals.

C-reactive protein (CRP), which is released by the liver in response to various stress triggers, including IL-6, produced in response to IL-1, was also measured in serum at the same time points as the PK samples. A PK/PD model was developed that incorporated a two compartment model for serum antibody level, and a concentration-dependent indirect response of antibody on the rate of CRP production, with a linear rate of elimination of CRP. After a single IV dose of 0.01 mg/kg antibody in Type 2 diabetes subjects, CRP declined within 7-10 days to 66±22% relative to 100% pre-dose, based on the model fits (FIG. 8). After a single IV dose of 0.03 mg/kg antibody in Type 2 diabetes subjects, CRP declined within 7-10 days to 40±12% relative to 100% pre-dose (FIG. 9). Data for the placebo controls are shown in FIG. 10. Based on these data and on the model projections, the anticipated maintained CRP levels following monthly injections of antibody are approximated to be 40% at 0.03 mg/kg, 16.5% at 0.1 mg/kg, 6.2% at 0.3 mg/kg, 1.9% at 1 mg/kg, and 0.66% at 3 mg/kg per month (FIG. 11). These data indicate that an IL-1β antibody as provided herein may be administered as infrequently as one month or longer to achieve a therapeutic effect (e.g., decrease in CRP levels) in a subject following a single administration of antibody.

Based on results obtained from the first clinical study, additional clinical trials are performed. Such trials may include one or more of the above dosages, as well as or alternatively one or more other dosages of IL-1β antibody, longer treatment and/or observation periods and greater numbers of patients per group (at least about 10, 50, 100, 200, 300, 400, 500, 750, 1000), in accordance with the invention. In addition, these and other studies also may be used to determine the period of time required to reach a desired therapeutic benefit based on change of a specific parameter (e.g., decrease in blood sugar, decrease in HbA1c, decrease in CRP), as well as the duration of the desired therapeutic benefit based on change of a specific parameter (e.g., decrease in blood sugar, decrease in HbA1c, decrease in CRP), before additional dosages are administered.

Example 10

Effect of IL-1β Antibody on Adipocyte Function and Insulin Resistance

An in vitro assay using cultured adipocytes may be used to demonstrate a reduction (e.g., blocking) of IL-1β-induced insulin resistance by using anti-IL-1β antibodies. The 3T3-L1 preadipocyte cell line obtained from ATCC (# CL-173) is grown at 7% $CO_2$ and 37° C. in DMEM, 25 mM glucose, and 10% calf serum and induced to differentiate in adipocytes. Briefly, 2 days after confluence, medium is exchanged for DMEM, 25 mM glucose, and 10% FCS supplemented with isobutylmethylxanthine (0.25 mM), dexamethasone (0.25 µM), insulin (5 µg/ml), and pioglitazone (10 µM). The medium is removed after 2 days and replaced with DMEM, 25 mM glucose, and 10% FCS supplemented with insulin (5 µg/ml) and pioglitazone (10 µM) for 2 days. Then the cells are fed every 2 days with DMEM, 25 mM glucose, and 10% FCS. 3T3-L1 adipocytes are used 8-15 days after the beginning of the differentiation protocol.

Human preadipocytes (Biopredic International, Rennes, France) are grown at 5% $CO_2$ and 37° C. in DMEM Ham's F12 containing 15 mM HEPES, 2 mM L-glutamine, 5% FCS, 1% antimycotic solution, ECGS/H-2, hEGF-5, and HC-500 from supplement pack preadipocyte growth medium (Promocell, Heidelberg, Germany). Differentiation into adipocytes is induced after confluence by exchanging the medium for DMEM Ham's F12 15 mM HEPES, 2 mM L-glutamine, and 3% FCS supplemented with biotin (33 µM), insulin (100 nM), pantothenate (17 µM), isobutylmethylxanthine (0.2 mM), dexamethasone (1 µM), and rosiglitazone (10 µM). The medium is removed after 3 days and replaced with Ham's F12 containing 15 mM HEPES, 2 mM L-glutamine, and 10% FCS supplemented with biotin (33 µM), insulin (100 nM), pantothenate (17 µM), and dexamethasone (1 µM). Then the cells are fed every 2 days with the same medium. Human adipocytes are used 15 days after the beginning of the differentiation protocol. Human preadipocytes also may be obtained from alternative sources, such as for example cell lines XA15A1 and XM18B1 (Lonza, Allendale, N.J.).

The role of IL-1β in inducing insulin resistance (decrease insulin sensitivity) in cultured adipocytes is shown by incubating adipocytes with IL-1β (e.g., 20 ng/mL, 48 hrs) and then incubating with different concentrations of insulin (e.g., 0.5 nM, 100 nM; 20 min), followed by measurement of glucose transport after the addition of 2-[$^3$H]deoxyglucose. Insulin resistance is determined as a reduction in glucose uptake, and the effect of an anti-IL-1β antibody at reducing (e.g., blocking) insulin resistance is readily measured in this adipocyte cell culture system.

The role of IL-1β in directly stimulating the production of adipokines and cytokines by adipoyctes (e.g., leptin, resistin, visfatin, IL-6, MCP-1 (CCL2), RANTES, PAI-1, Acylation-stimulating protein, SAA3, Pentraxin-3, macrophage migration inhibition factor, IL-1RA, IL-12, IL-8, IL-6, TNF-α) is determined by culturing adipoyctes in the absence or presence of different concentrations of IL-1β for different lengths of time as described above, and measuring levels of adipocytes and cytokines in the culture-conditioned medium, usually via ELISA or other commonly used methods. In addition, the effects of treating IL-1β-stimulated adipocyte cultures with an anti-IL-1β neutralizing antibody on the induction of adipokine and/or cytokine secretion related to insulin resistance are measured. Similarly, the effects of treating with an anti-IL-1β antibody on suppressing the insulin-sensitizing adipokine, adiponectin, are measured. To address whether anti-IL-1β antibody treatment neutralizes the effects of endogenously-produced IL-1 derived from immune/inflammatory cells (e.g., macrophages) during adipose tissue inflammation, different numbers of human macrophages (monocyte-derived or various monocytic cell lines) are cultured with the adipocyte cultures described above in the absence or presence of anti-IL-1β antibody and modulation of adipokines and cytokines are measured. In addition, the modulating effects on adipokine and cytokine secretion after in vivo treatment of a subject with an anti-IL-1β antibody are measured in the circulation (e.g., serum, plasma), as a means to demonstrate efficacy.

Example 11

Inhibition of Cytokine Production in Human Whole Blood by an IL-1β Antibody

Measuring cytokines in blood during a disease or the treatment of a disease can be useful for determining disease severity or response to a therapy. Usually, cytokine levels are measured in serum, but this method does not necessarily measure total cytokines. Many cytokines can be inside cells (intracellular). In addition, the ability for a cell to produce a cytokine may be more useful information than the level of circulating cytokine.

A method of stimulating whole blood was used to determine cytokine production and the effect of treating with an anti-IL-1β antibody. Blood was drawn from patients into sterile heparinized tubes and then 250 ul of the whole blood was added to each 4 mL orange top Corning sterile cryotube set up as follows:

Control Series

All tubes were pre-filled with 550 ul of RPMI. To tube 1 (control), 200 ul RPMI was added and to tubes 2-10, 100 ul additional RPMI was added. To each of tubes 2-10, 100 ul of dilutions of an anti-IL-1β antibody (AB7) was added.

Test Series

A similar series of antibody dilutions was set up as detailed above.

All tubes were mixed well using a 10 second vortex. Control series tubes A1-10 then received an additional 100 ul of RPMI, were vortexed 10 seconds, the screw cap tightly fixed and the tubes placed in incubator. To Test series tubes B1-10, 100 ul of heat-killed *Staphylococcus epidermidis* (final concentration of 1:1000 of stock resulting in a bacterium:white blood cell ration of 10:1) was added, the tubes were then vortexed for 10 seconds, capped and placed in 37° C. incubator. After 24 hours incubation, the cultures were all lysed with Triton X (0.5% final) to release the cell contents and the lysates were frozen. After lysis of the whole blood cultures, the tubes subjected to freeze thaw cycles and cytokine levels are measured by standard cytokine ELISA assays for human TNFα, IL-6, IFNγ, IL-8, IL-1α, IL-1Ra and IL-1β (R&D Systems, Minneapolis, Minn.).

Cytokines measured in the control series tubes, which contain only sterile culture medium and antibody (where indicated), reflect the spontaneous level of stimulation. In healthy subjects, very low levels of the various cytokines are found when measured after 24 hours of incubation. In patients with untreated diseases, the levels may be higher. The Test series of tubes additionally contained a defined amount of heat-killed *Staphylococcus epidermidis*, which stimulates production of a number of cytokines. If the anti-IL-1β antibody treatment is efficacious, this will be reflected by reduces cytokine production.

As shown in FIG. 6, the high affinity anti-IL-1β antibody AB7 was very effective at inhibiting the production of IL-1β in human blood. In an average of three human samples, the antibody inhibited the production of IL-1β induced by *Staphylococcus epidermidis* by 50% at 0.1 pM and by 75% at 3 pM. At 100 pM, inhibition was 100%. Interferon gamma (IFNγ) was induced by *Staphylococcus epidermidis* and AB7 reduced IFNγ induced by *Staphylococcus epidermidis* by 75% at 100 pM.

Example 12

Effect of Anti-IL-1β Antibody on Diabetes in the Non-Obese Diabetic (NOD) Mouse

To demonstrate efficacy of an anti-IL-1β antibody in a mouse diabetes model, female 3- to 4-week-old NOD mice (Jackson Laboratories, Bar Harbor, Me.) are obtained and housed in a vivarium under pathogen-free conditions. Various doses of anti-IL-1β antibody (e.g., 3 to 600 µg) are diluted in a suitable vehicle (e.g., PBS) and administered in prediabetic female NOD mice starting no later than 6 weeks of age, using different routes (e.g., intraperitoneally, subcutaneously, intravenously) at defined intervals (e.g., weekly, biweekly, monthly). Blood glucose is monitored using a glucometer (Encore Glucometer; Bayer, Elkhart, Ind.) at weekly intervals, beginning at 10 weeks of age. Mice with blood glucose levels 200 mg/dl on two consecutive occasions are considered diabetic (diabetes onset is usually observed around 15 to 20 weeks of age and the incidence usually achieves a maximum around 90% by 30 weeks of age). The data are calculated as the percentage of animals remaining diabetes-free over the course of the experiment. The differences between curves are tested using the log-rank test, which compares the distributions over the entire observation period.

In another NOD mouse model, efficacy of the anti-IL-1b antibody is demonstrated in a cyclophosphamide (CY)-accelerated disease model (Reddy et al., Histochem J. 33:317-327, 2001; Cailleau et al., Diabetes 46:937-940, 1997; Reddy et al., Histochem J., 34:1-12, 2002; Harada et al., Diabetologia 27:604-606, 1984; Nicoletti, et al., Eur J Immunol 24:1843-7, 1994). Non-diabetic 4- to 8-week old male (or female) NOD mice are obtained (Jackson Laboratories, Bar Harbor, Me.) and housed in a vivarium under pathogen-free conditions. Mice are injected with a single dose of CY (Sigma) at 200 mg/Kg and are treated at various accelerated intervals due to the accelerated nature of the model (e.g., once per week, twice per week) for two to three weeks with or without various doses of anti-IL-1β (e.g., 3 ug, 30 ug, 150 ug, 600 μg) or isotype control antibodies diluted in a suitable vehicle (e.g., PBS) using different routes of administration (e.g., intraperitoneally, subcutaneously, intravenously). Urine glucose (glycosuria) levels are monitored three times a week and blood glucose levels are monitored once per week using a glucometer beginning the day before CY injection. Urine glucose levels >20 mmol/L on two consecutive occasions are considered diabetic and reduction of urine glucose levels by an anti-IL-1β antibody are a measure of efficacy.

In another model, the efficacy of an anti-IL-1β antibody is evaluated in a diabetes-recurrence model of pancreatic islet transplantation (not transplant rejection) (Mellgren et al., Diabetologia 29:670-2, 1986; Sandberg, et al., Clin Exp Immunol 108:314-7, 1997). Non-diabetic 4- to 8-week old female NOD mice are obtained (Jackson Laboratories, Bar Harbor, Me.) and housed in a vivarium under pathogen-free conditions. Pancreatic islets are prepared from 5-6 week-old non-diabetic male and female NOD mice before marked leukocytic infiltration and transplanted under the kidney capsule of spontaneous diabetic (15 to 20 week-old) female NOD mice (400 to 450 islets/mouse). Transient normoglycemia occurs shortly after transplantation and hyperglycemia usually re-appears approximately 6 days after transplantation. Mice are treated with or without various doses of anti-IL-1β (e.g., 3 ug, 30 ug, 150 ug, 600 μg) or isotype control antibodies diluted in a suitable vehicle (e.g., PBS) using different routes of administration (e.g., intraperitoneally, subcutaneously, intravenously). Blood glucose levels are monitored before and after transplantation once or twice per week using a glucometer and mice with levels >200 mg/dl on two consecutive occasions are considered diabetic and reduction of blood glucose levels by an anti-IL-1β antibody are a measure of efficacy.

Example 13

Treatment of Low-dose Streptozotocin-induced Diabetes Model in C57BL/K Mice

To demonstrate efficacy of an anti-IL-1β antibody in a multiple low-dose streptozotocin (STZ)-induced hyperglycemia and insulitis diabetes model (Sandberg, et al., Biochem Biophys Res Commun 202:543-548, 1994; Reddy, et al., Ann N Y Acad Sci 1079:109-113, 2006), 4- to 8-week old C57BL/K mice are obtained (Jackson Laboratories, Bar Harbor, Me.) and housed in a vivarium under pathogen-free conditions. Mice receive five daily injections of STZ (40 mg/kg) in this accelerated model and are subjected to accelerated treatment (starting one day before STZ injection) at various intervals (e.g., once, twice, or three times a week) for one to three weeks with or without various doses of anti-IL-1β (e.g., 3 ug, 30 ug, 150 ug, 600 ug) or isotype control antibodies diluted in a suitable vehicle (e.g., PBS) using different routes of administration (e.g., intraperitoneally, subcutaneously, intravenously). Blood glucose levels are monitored once per week using a glucometer beginning one day before STZ injection. Blood glucose levels >200 mg/dl on two consecutive occasions are considered diabetic and reduction of blood glucose levels by an anti-IL-1β antibody are a measure of efficacy.

Example 14

Treatment in the Diet-Induced Obesity Model of Type 2 Diabetes

Figure 12:
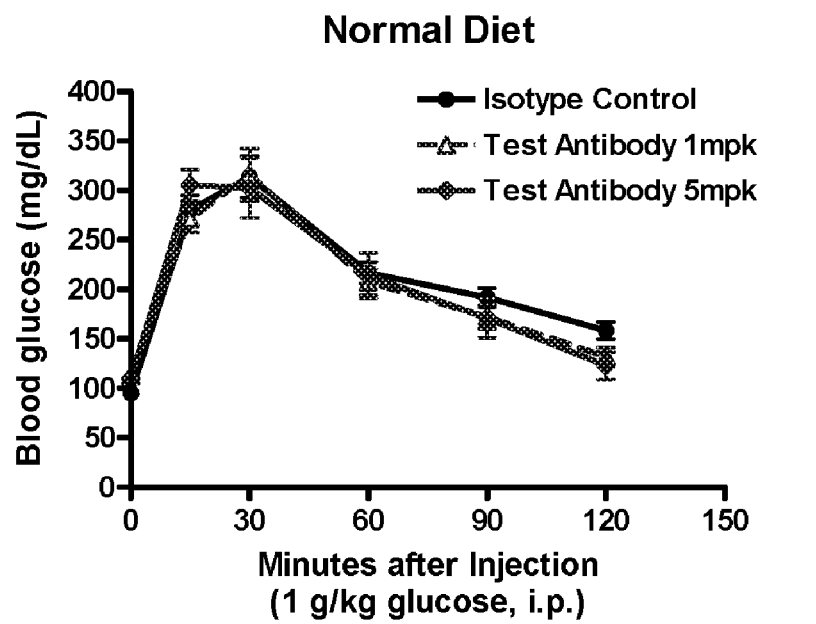
FIG. 12 is graphs showing the effect of AB7 in a diet-induced obesity mouse model of Type 2 diabetes.
Figure 12:
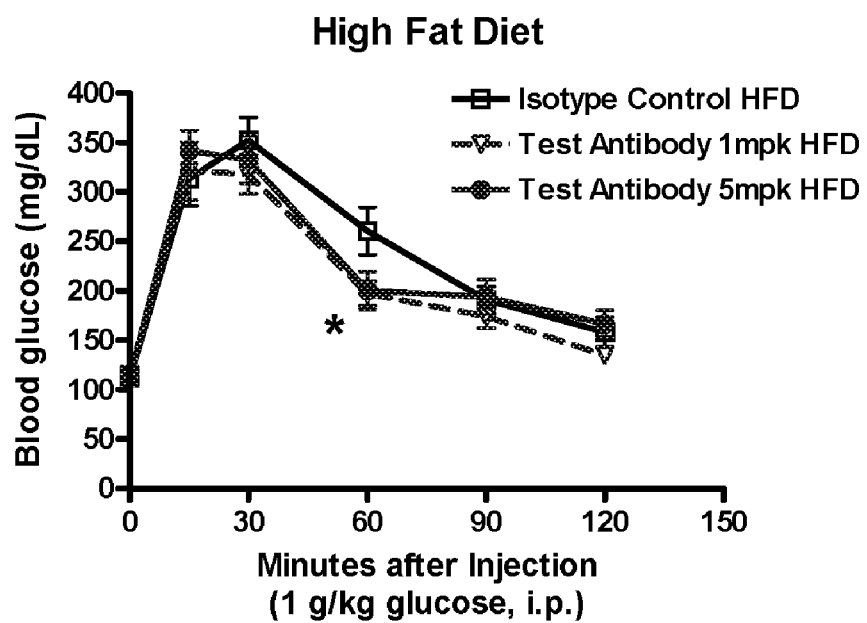

The efficacy of an anti-IL-1β antibody was tested in the diet-induced obesity (DIO) model of Type 2 diabetes. In this model, mice fed a diet with high fat content become obese over a period of several weeks, and they exhibit impaired glucose tolerance and impaired insulin secretion when challenged with a bolus injection of glucose. C57BL/6 male mice, 6 weeks of age, were fed normal diet (ND, Teklad, 5 kcal % fat) or Surwit's high fat, high sucrose diet (HFD, Research Diets #D12331, 58 kcal % fat). Antibody dosing was initiated the day before. The anti-IL-1β test antibody (AB7) and isotype control human IgG2 antibody were administered by intraperitoneal (i.p.) injection. Antibodies were dosed twice a week for 4 weeks. Body weight was also recorded twice a week. After 4 weeks, mice were subjected to a glucose tolerance test (GTT). In the GTT, mice are fasted overnight, and then injected i.p. with 1 g/kg of glucose. Blood glucose is measured from tail nicks at 0, 15, 30, 60, 90, and 120 minutes after the injection, using a FreeStyle glucometer. FIG. 12 shows that mice fed a high fat diet for 4 weeks had impaired glucose tolerance compared to mice on the normal diet (FIG. 1). Administration of an IL-1β test antibody protected HFD mice from impaired glucose tolerance. At 60 minutes during the GTT, performance of mice dosed with 1 mg/kg of IL-1β antibody were significantly better than mice that had received IgG2 control antibody (*, $p<0.05$). Notably, the positive results in this mouse model were observed even though the AB7 antibody has a much lower affinity (~10,000 fold) and in vitro potency for mouse IL-1β, as compared to human IL-1β, as described in Example 2 above.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element of the invention, it is specifically contemplated that a closed-ended term can be used in place of the open-ended term without departing from the spirit and scope of the invention. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those working in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating Type 2 diabetes in a human, the method comprising administering an anti-IL-1β antibody or fragment thereof to the human, wherein the antibody or antibody fragment binds to human IL-1β with a dissociation constant of about 250 pM or less.

2. The method of claim 1, wherein administration of an initial dose of the antibody or antibody fragment is followed by the administration of one or more subsequent doses.

3. The method of claim 1, wherein administration of an initial dose of the antibody or antibody fragment is followed by the administration of one or more subsequent doses, and wherein said one or more subsequent doses are in an amount that is approximately the same or less than the initial dose.

4. The method of claim 1, wherein administration of an initial dose of the antibody or antibody fragment is followed by the administration of one or more subsequent doses, and wherein at least one of the subsequent doses is in an amount that is more than the initial dose.

5. The method of any one of claims 1, 2, 3, 4, wherein the antibody or antibody fragment binds to human IL-1β with a dissociation constant of about 50 pM or less.

6. The method of any one of claims 1, 2, 3, 4, wherein the antibody or antibody fragment binds to human IL-1β with a dissociation constant of about 10 pM or less.

7. The method of any one of claims 1, 2, 3, 4, wherein the antibody or antibody fragment binds to human IL-1β with a dissociation constant of about 1 pM or less.

8. The method of any one of claims 1, 2, 3, 4, wherein the antibody or antibody fragment binds to human IL-1β with a dissociation constant of about 0.5 pM or less.

9. The method of any one of claims 2, 3, 4, wherein the initial dose and each one or more subsequent doses are separated from each other by an interval of at least about 2 weeks.

10. The method of any one of claims 2, 3, 4, wherein the initial dose and each one or more subsequent doses are separated from each other by an interval of at least about 1 month.

11. The method of any one of claims 2, 3, 4, wherein the initial dose and each one or more subsequent doses are separated from each other by an interval of at least about 3 months.

12. The method of any one of claims 2, 3, 4, wherein the initial dose and each one or more subsequent doses are separated from each other by an interval of at least about 6 months.

13. The method of claim 1, wherein the antibody or antibody fragment is administered in one or more doses of 3 mg/kg or less of antibody or fragment.

14. The method of claim 1, wherein the antibody or antibody fragment is administered in one or more doses of 1 mg/kg or less of antibody or fragment.

15. The method of claim 1, wherein the antibody or antibody fragment is administered in one or more doses of 0.3 mg/kg or less of antibody or fragment.

16. The method of claim 1, wherein the antibody or antibody fragment is administered in one or more doses of 0.1 mg/kg or less of antibody or fragment.

17. The method of claim 1, wherein the antibody or antibody fragment is administered in one or more doses of 0.03 mg/kg or less of antibody or fragment.

18. The method of claim 1, wherein the antibody or antibody fragment is administered in one or more doses of 0.01 mg/kg or less of antibody or fragment.

19. The method of any one of claims 13-18, wherein the one or more doses are at least 0.01 mg/kg of antibody or fragment.

20. The method of any one of claims 1, 2, 3, 4, wherein the anti-IL-1β antibody or antibody fragment is a neutralizing antibody.

21. The method of any one of claims 1, 2, 3, 4, wherein the anti-IL-1β antibody or antibody fragment binds to an IL-1β epitope such that the bound antibody or fragment substantially permits the binding of IL-1β to IL-1 receptor I (IL-1RI).

22. The method of any one of claims 1, 2, 3, 4, wherein the antibody or antibody fragment does not detectably bind to IL-1α, IL-1R or IL-1Ra.

23. The method of anyone of claims 1, 2, 3, 4, wherein the antibody or antibody fragment binds to an epitope contained in the sequence ESVDPKNYPKKKMEKRFVFNKIE (SEQ ID NO: 1).

24. The method of any one of claims 1, 2, 3, 4, wherein the antibody or antibody fragment binds to an epitope incorporating Glu64 of IL-1β.

25. The method of any one of claims 1, 2, 3, 4, wherein the antibody or antibody fragment binds to amino acids 1-34 of the N terminus of IL-1β.

26. The method of any one of claims 1, 2, 3, 4, wherein the antibody or antibody fragment is human engineered or humanized.

27. The method of any one of claims 1, 2, 3, 4, wherein the antibody or antibody fragment is human.

28. The method of any one of claims 1, 2, 3, 4, wherein the anti-IL-1β antibody or fragment is administered by subcutaneous, intravenous or intramuscular injection.

29. The method of any one of claims 1, 2, 3, 4, wherein the antibody or fragment is administered as a fixed dose, independent of a dose per subject weight ratio.

30. The method of claim 29, wherein the antibody or fragment is administered in one or more doses of 500 mg or less of antibody or fragment.

31. The method of claim 29, wherein the antibody or fragment is administered in one or more doses of 250 mg or less of antibody or fragment.

32. The method of claim 29, wherein the antibody or fragment is administered in one or more doses of 100 mg or less of antibody or fragment.

33. The method of claim 29, wherein the antibody or fragment is administered in one or more doses of at least 10 mg of antibody or fragment.

34. The method of anyone of claims 1, 2, 3, 4, wherein a dose of the antibody or fragment is sufficient to achieve at least a 0.5 percentage point improvement in hemoglobin A1c.

35. The method of any one of claims 1, 2, 3, 4, wherein the dose of the antibody or fragment is sufficient to achieve at least a 1 percentage point improvement in hemoglobin A1c.

36. The method of any one of claims 1, 2, 3, 4, wherein said method is sufficient to achieve at least one of the following modifications: reduction in fasting blood sugar level, decrease in insulin resistance, reduction of hyperinsulinemia, improvement in glucose tolerance, improvement in CRP levels, reduction of hyperglycemia, reduction in the need for diabetes medication, reduction in BMI, change in glucose/insulin C-peptide AUC, decrease in triglyceride level, or decrease in the level of free fatty acids.

37. The method of any one of claims 1, 2, 3, 4, wherein said method reduces or prevents a complication or condition associated with Type 2 diabetes selected from the group consisting of retinopathy, renal failure, cardiovascular disease, and wound healing, the method comprising administering an anti-IL-1β antibody or fragment thereof to the human.

38. The method of claim 37, wherein the complication or condition is cardiovascular disease, and wherein said cardiovascular disease is atherosclerosis or peripheral vascular disease.

39. The method of claim 37, wherein the complication or condition is wound healing, and wherein said wound healing condition is diabetic ulcer.

40. The method of claim 1, wherein said method is in conjunction with at least one additional treatment method, said additional treatment method comprising administering at least one pharmaceutical composition comprising an active agent other than an IL-1β antibody or fragment.

41. The method of claim 1, wherein said method prevents or delays the need for at least one additional treatment method, said additional treatment method comprising administering at least one pharmaceutical composition comprising an active agent other than an IL-1β antibody or fragment.

42. The method of claim 1, wherein said method reduces the amount, frequency or duration of at least one additional treatment method, said additional treatment method comprising administering at least one pharmaceutical composition comprising an active agent other than an IL-1β antibody or fragment.

43. The method of any one of claims 40-42, wherein said at least one pharmaceutical composition comprising an active agent other than an IL-1β antibody or fragment is selected from the group consisting of a sulfonylurea, a meglitinide, a biguanide, an alpha-glucosidase inhibitor, a thiazolidinedione, GLP-1, and insulin.

44. The method of any one of claims 40-42, wherein said active agent is a sulfonylurea.

45. The method of any one of claims 40-42, wherein said active agent is a meglitinide.

46. The method of any one of claims 40-42, wherein said active agent is a biguanide.

47. The method of any one of claims 40-42, wherein said active agent is an aipha-glucosidase inhibitor.

48. The method of any one of claims 40-42, wherein said active agent is a thiazolidinedione.

49. The method of any one of claims 40-42, wherein said active agent is GLP-1.

50. The method of any one of claims 40-42, wherein said active agent is insulin.

51. The method of claim 1, wherein the antibody or antibody fragment is administered in one or more doses from about 0.1 mg/kg to about 1 mg/kg of antibody or fragment.

52. The method of claim 1, wherein the antibody or fragment is administered as a fixed dose, independent of a dose per subject weight ratio, and wherein the fixed dose is from about 1 mg to about 25 mg.

53. The method of any one of claims 40-42, wherein said at least one pharmaceutical composition comprising an active agent other than an IL-1β antibody or fragment is metformin.

54. The method of any one of claims 40-42, wherein said at least one pharmaceutical composition comprising an active agent other than an IL-1β antibody or fragment is a DPP-IV inhibitor.

* * * * *